US008258102B2

(12) United States Patent
    Sleep

(10) Patent No.: US 8,258,102 B2
(45) Date of Patent: Sep. 4, 2012

(54) GENE AND POLYPEPTIDE SEQUENCES

(75) Inventor: Darrell Sleep, West Bridgford (GB)

(73) Assignee: Novozymes Biopharma DK A/S, Bagsvaard (DK)

( * ) Notice: Subject to any disclaimer, the term of this patent is extended or adjusted under 35 U.S.C. 154(b) by 1161 days.

(21) Appl. No.: 10/522,074

(22) PCT Filed: Jul. 23, 2003

(86) PCT No.: PCT/GB03/03273
    § 371 (c)(1),
    (2), (4) Date: Jul. 8, 2005

(87) PCT Pub. No.: WO2004/009819
    PCT Pub. Date: Jan. 29, 2004

(65) Prior Publication Data
    US 2006/0183187 A1    Aug. 17, 2006

(30) Foreign Application Priority Data

Jul. 23, 2002  (GB) .................................. 0217033.0

(51) Int. Cl.
    *A61K 38/10*    (2006.01)
    *A61K 38/40*    (2006.01)
    *A61K 49/14*    (2006.01)
    *C12P 19/34*    (2006.01)
    *C12N 15/64*    (2006.01)
(52) U.S. Cl. ...... 514/21.4; 530/326; 435/91.1; 435/91.4
(58) Field of Classification Search .................. None
    See application file for complete search history.

(56) References Cited

U.S. PATENT DOCUMENTS

| 5,639,642 | A | 6/1997 | Kjeldsen |
| 5,766,883 | A | 6/1998 | Ballance |
| 5,795,746 | A | 8/1998 | Kjeldsen |
| 5,859,195 | A | 1/1999 | Collins |
| 6,214,547 | B1 | 4/2001 | Kjeldsen |
| 2006/0241027 | A1* | 10/2006 | Hauser et al. .................. 514/12 |
| 2009/0227775 | A1* | 9/2009 | Hauser et al. ................. 530/362 |

FOREIGN PATENT DOCUMENTS

| CA | 2447212 | 10/2002 |
| EP | 322094 | 6/1989 |
| EP | 366400 | 5/1990 |
| EP | 0 399 666 | 11/1990 |
| EP | 411893 | 2/1991 |
| WO | 90/01063 | 2/1990 |
| WO | WO 93/18181 | 9/1993 |
| WO | 95/33833 | 12/1995 |
| WO | WO 96/29415 | 9/1996 |
| WO | 96/37515 | 11/1996 |
| WO | 98/16643 | 4/1998 |
| WO | 99/53051 | 10/1999 |
| WO | WO-01/64834 A2 * | 9/2001 |
| WO | 01/79258 | 10/2001 |
| WO | 01/79271 | 10/2001 |
| WO | 01/79442 | 10/2001 |
| WO | 01/79443 | 10/2001 |
| WO | 01/79444 | 10/2001 |
| WO | 01/79480 | 10/2001 |
| WO | 02/083876 | 10/2002 |
| WO | 03/066078 | 8/2003 |
| WO | 03/066085 | 8/2003 |
| WO | 03/066824 | 8/2003 |

OTHER PUBLICATIONS

Ogata, et al., Science, 2001, 293, 2093-2098.*
STN search result for Ogata, et al., Science, 2001, 293, 2093-2098, 1 page.*
Sleep, et al., 1990, Biotechnology, 8, 42-46.*
Munson, 1993, Journal of Bacteriology, 175, 6426-6432.*
Street, 1996, Biochimica et Biophysica Acta, 1305, 87-97.*
Ali et al., J. Biol. Chem., 274:24066-24073 (1999).
Database Accession No. 473511-23-8 (Information on SEQ ID No. 1025 from WO/02083876).
Genbank Accession No. CAD09246.
Harris and Aisen, "Iron Carriers and Iron Proteins", vol. 5, Physical Bioinorganic Chemistry, VCH (1991).
Hinnen et al., Proc. Natl. Acad. Sci. USA, 75:1929-1933 (1978).
Hoefs, Hepatology, 16:396-403 (1992).
Kerry-Williams et al., Yeast, 14:161-169 (1998).
Mason et al., Biochemistry, 32:5472-5479 ((1993).
Mason et al., Biochem. J., 330:35-40 (1998).
Mason et al., Protein Expr. Purif., 8:119-125 (1996).
Mason et al., Protein Expr. Purif., 2:214-220 (1991).
Mason et al., Biochemistry, 41:9448-9454 (2002).
Mead et al., Mol. Gen. Genet., 205:417-421 (1986).
Okabayshi et al., J. Biochem., 110:103-110 (1991).
Parkhill et al., Nature, 413:848-852 (2001).
Sharp and Crowe, Yeast, 7:657-678 (1991).
Shin et al., Proc. Natl. Acad. Sci USA, 92:2820 (1995).
Sleep et al., Biotechnology, 8:42-46 (1990).
Sleep et al., Biotechnology, 9:183-187 (1991).
Smith et al., Science, 229:1219-1224 (1985).
Testa, "Proteins of Iron Metabolism", CRC Press (2002).
Elliot et al, "Secretion of Glycosylated Human Erythropoietin", Gene, vol. 79, pp. 167-180 (1989).
Nothwehr S.F.et al., "Targeting of Proteins Into The Eukaryotic Secretory Pathway; Signal Peptide Structure/Function Relationships", Bioessays, vol. 12, No. 10, pp. 479-484 (1990).
Guo Meijing, "Research Progresses in The Expression of Recombinant Human Serum Albumin", Advance in Biological Engineering, vol. 20, No. 5, pp. 39-42 (2000).
Gierasch L M, "Signal Sequences" Biochemistry, vol. 28, No. 3, pp. 923-930 (1989).

(Continued)

*Primary Examiner* — Karlheinz R Skowronek
*Assistant Examiner* — Satyanarayana R Gudibande
(74) *Attorney, Agent, or Firm* — Michael W. Krenicky

(57) ABSTRACT

The present invention provides a polypeptide comprising (i) a leader sequence, the leader sequence comprising a (a) secretion pre sequence, and (b) the following motif: $-X_1-X_2-X_3-X_4-X_5-$ where $X_1$ is phenylalanine, tryptophan, or tyrosine, $X_2$ is isoleucine, leucine, valine, alanine or methionine, $X_3$ is leucine, valine, alanine or methionine, $X_4$ is serine or threonine and $X_5$ is isoleucine, valine, alanine or methionine; and (ii) a desired protein heterologous to the leader sequence. A polypeptide of the invention may additionally comprise, as part of the leader sequence, a secretion pro sequence. The invention also provides a polynucleotide comprising a sequence that encodes a polypeptide of the invention and a cell, preferably a yeast cell, comprising said polynucleotide.

75 Claims, 22 Drawing Sheets

OTHER PUBLICATIONS

Dayhoff, "A Model of Evolutionary Change in Proteins", Atlas of Protein Sequence and Structure, vol. 5, ch. 9, pp. 89-99 (1972).

French et al., "What is a Conservative Substitution?", Journal of Molecular Evolution, vol. 19, pp. 171-175 (1983).

Adelman et al., "Calcium activated potassium channels expressed from cloned complementary DNAs", Neuron, vol. 9, pp. 209-216 (1992).

Chung et al., "The use of inulinase pre-pro leader peptide for secretion of heterologous proteins in *Saccharoymces cerevisiae*", Biotechnology Letters, vol. 18, No. 6, pp. 627-632 (1996).

Database Accession No. AAE02154, Seq. No. 2 from US Patent No. 5,859,195 (1999).

Dugiaczyk et al., "Nucleotide sequence and the encoded amino acids of human serum albumin mRNA", Proc Natl Acad Sci, USA, vol. 79, pp. 71-75 (1982).

Kaiser et al., "Many random sequences functionally replace the secretion signal sequence of yeast invertase", Science, vol. 235, pp. 312-317 (1987).

Lin et al., "Heterlogous protein expression in the methylotrophic yeast *Pichia pastoris*", FEMS Microbiology Reviews, vol. 24, pp. 45-66 (2000).

Ogata et al., "Mechanisms of Evolution in *Rickettsia conorii* and *R. prowazekii*", Science 293, pp. 2093-2098 (2001).

Sjimons et al., "Production of correctly processed human serum albumin in transgenic plants", Biotechnology, vol. 8, pp. 217-221 (1990).

Voet et al., "Signal peptides are removed from nascent proteins by a signal peptidase", Biochemistry, vol. 2, pp. 1008-1009 (1995).

Zhang et al., Database Accession No. AAX82486, Nucleotide Seq. No. 607 (2005).

* cited by examiner

Fig.1

```
        |---------------------------pre-albumin---------------------------||---------pro region---------|
Pre  Pro
HSA  HSA   Met Lys Trp Val Thr Phe Ile Ser Leu Leu Phe Leu Phe Ser Ser Ala Tyr Ser Arg Gly Val Phe Arg Arg
HSA  MFα-1 Met Lys Trp Val Thr Phe Ile Ser Leu Leu Phe Leu Phe Ser Ser Ala Tyr Ser Arg Ser Leu Asp Lys Arg
           -24 -23 -22 -21 -20 -19 -18 -17 -16 -15 -14 -13 -12 -11 -10 -9  -8  -7  -6  -5  -4  -3  -2  -1

Preferred mutations
of the invention:          Phe Ile Val     Ile
```

Fig.2

Standard genetic code

|   | T | C | A | G |
|---|---|---|---|---|
| T | TTT Phe (F)<br>TTC Phe (F)<br>TTA Leu (L)<br>TTG Leu (L) | TCT Ser (S)<br>TCC Ser (S)<br>TCA Ser (S)<br>TCG Ser (S) | TAT Tyr (Y)<br>TAC Tyr (Y)<br>TAA Ter<br>TAG Ter | TGT Cys (C)<br>TGC Cys (C)<br>TGA Ter<br>TGG Trp (W) |
| C | CTT Leu (L)<br>CTC Leu (L)<br>CTA Leu (L)<br>CTG Leu (L) | CCT Pro (P)<br>CCC Pro (P)<br>CCA Pro (P)<br>CCG Pro (P) | CAT His (H)<br>CAC His (H)<br>CAA Gln (Q)<br>CAG Gln (Q) | CGT Arg (R)<br>CGC Arg (R)<br>CGA Arg (R)<br>CGG Arg (R) |
| A | ATT Ile (I)<br>ATC Ile (I)<br>ATA Ile (I)<br>ATG Met (M) | ACT Thr (T)<br>ACC Thr (T)<br>ACA Thr (T)<br>ACG Thr (T) | AAT Asn (N)<br>AAC Asn (N)<br>AAA Lys (K)<br>AAG Lys (K) | AGT Ser (S)<br>AGC Ser (S)<br>AGA Arg (R)<br>AGG Arg (R) |
| G | GTT Val (V)<br>GTC Val (V)<br>GTA Val (V)<br>GTG Val (V) | GCT Ala (A)<br>GCC Ala (A)<br>GCA Ala (A)<br>GCG Ala (A) | GAT Asp (D)<br>GAC Asp (D)<br>GAA Glu (E)<br>GAG Glu (E) | GGT Gly (G)<br>GGC Gly (G)<br>GGA Gly (G)<br>GGG Gly (G) |

Single letter code:

A = adenosine

C = cytidine

G = guanosine

T = thymidine

Modified list of preferred yeast codons

|   | T | C | A | G |
|---|---|---|---|---|
| T | TTC Phe (F)<br>TTG Leu (L) | TCT Ser (S)<br>TCC Ser (S) | TAC Tyr (Y)<br>TAA Ter | TGT Cys (C)<br>TGG Trp (W) |
| C |   | CCA Pro (P) | CAT His (H)<br>CAA Gln (Q) |   |
| A | ATT Ile (I)<br>ATC Ile (I)<br>ATG Met (M) | ACT Thr (T)<br>ACC Thr (T) | AAC Asn (N)<br>AAG Lys (K) | AGA Arg (R) |
| G | GTT Val (V)<br>GTC Val (V) | GCT Ala (A) | GAT Asp (D)<br>GAC Asp (D)<br>GAA Glu (E) | GGT Gly (G) |

Fig.15
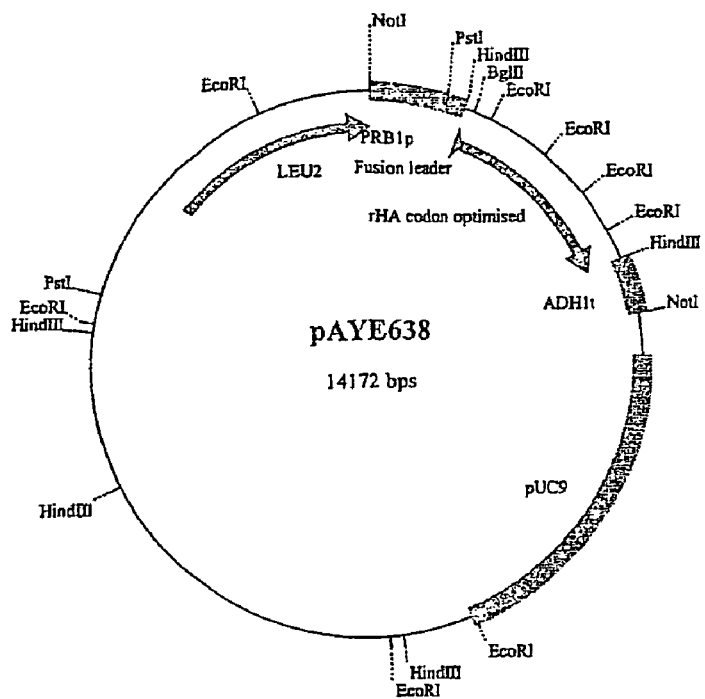
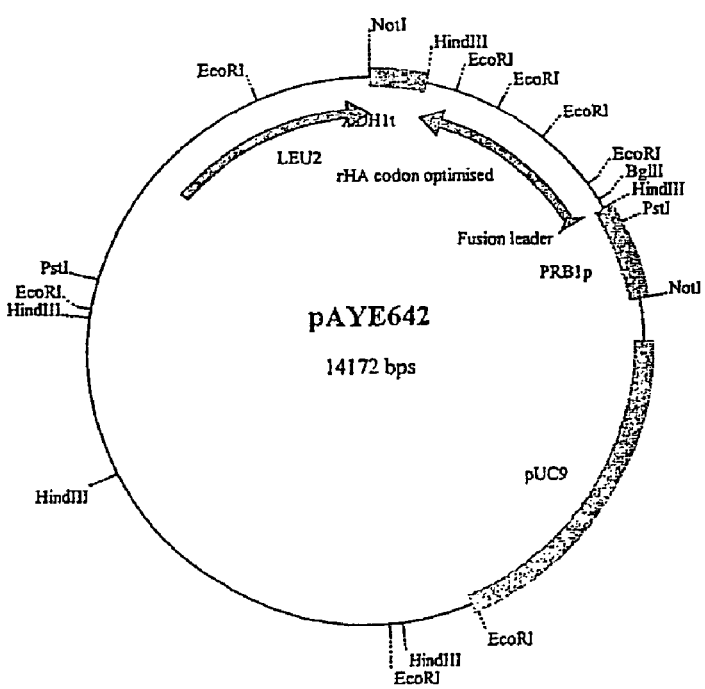

Fig.21

| Strain | Plasmid | Yx/s (g/g) | Yp/s (mg/g) | rHA (g/L) |
|---|---|---|---|---|
| C | pAYE443 (1st feeds) | 0.33 | 10.4 | 2.9 |
|   | (fill and draw) | 0.34 | 11.5 | 3.2 |
|   | pAYE638 (1st feeds) | 0.36 | * | * |
|   | (fill and draw) | 0.36 | 2.4 | 0.7 |
|   | pAYE646 (1st feeds) | 0.33 | 11.6 | 3.2 |
|   | (fill and draw) | 0.35 | 12.2 | 3.5 |
|   | pAYE655 (1st feeds) | 0.37 | 12.1 | 3.4 |
|   | (fill and draw) | 0.35 | 13.0 | 3.7 |
| B | pAYE443 (1st feeds) | 0.35 | 10.5 | 2.8 |
|   | pAYE646 (1st feeds) | 0.35 | 13.0 | 3.5 |
|   | (fill and draw) | 0.33 | 12.8 | 3.6 |

Fig. 22

| Plasmid designation | Leader | Desired Protein |
|---|---|---|
| pAYE443<br>pAYE467 | HSA/MFα-1<br>natural codon bias | HSA<br>natural codon bias |
| pAYE655<br>pAYE643 | modified HSA/MFα-1<br>FIVSI fully codon biased the rest has natural codon bias | HSA<br>natural codon bias |
| pAYE638<br>PAYE639<br>pAYE640<br>pAYE642 | HSA/MFα-1<br>all fully codon biased | HSA<br>fully codon biased |
| pAYE645<br>pAYE646<br>pAYE647 | modified HSA/MFα-1<br>all fully codon biased | HSA<br>fully codon biased |

SEQUENCE LISTING

<160> NUMBER OF SEQ ID NOS: 40

<210> SEQ ID NO 1
<211> LENGTH: 5
<212> TYPE: PRT
<213> ORGANISM: Artificial Sequence
<220> FEATURE:
<223> OTHER INFORMATION: Synthetic polypeptide leader sequence
<220> FEATURE:
<221> NAME/KEY: MISC_FEATURE

```
<222> LOCATION: (1)..(1)
<223> OTHER INFORMATION: CAN BE EITHER Phe OR Trp OR Tyr
<220> FEATURE:
<221> NAME/KEY: MISC_FEATURE
<222> LOCATION: (2)..(2)
<223> OTHER INFORMATION: CAN BE EITHER Ile OR Leu OR Val OR Ala OR Met
<220> FEATURE:
<221> NAME/KEY: MISC_FEATURE
<222> LOCATION: (3)..(3)
<223> OTHER INFORMATION: CAN BE EITHER Leu OR Val or ALA or Met
<220> FEATURE:
<221> NAME/KEY: MISC_FEATURE
<222> LOCATION: (4)..(4)
<223> OTHER INFORMATION: CAN BE EITHER Ser OR Thr
<220> FEATURE:
<221> NAME/KEY: MISC_FEATURE
<222> LOCATION: (5)..(5)
<223> OTHER INFORMATION: CAN BE EITHER Ile OR Val OR Ala OR Met

<400> SEQUENCE: 1

Xaa Xaa Xaa Xaa Xaa
1

```
<210> SEQ ID NO 4
<211> LENGTH: 5
<212> TYPE: PRT
<213> ORGANISM: Artificial Sequence
<220> FEATURE:
<223> OTHER INFORMATION: Synthetic polypeptide leader sequence
<220> FEATURE:
<221> NAME/KEY: MISC_FEATURE
<222> LOCATION: (1)..(1)
<223> OTHER INFORMATION: CAN BE EITHER Phe OR Trp OR Tyr
<220> FEATURE:
<221> NAME/KEY: MISC_FEATURE
<222> LOCATION: (2)..(2)
<223> OTHER INFORMATION: CAN BE EITHER Ile OR Leu OR Val OR Ala OR Met
<220> FEATURE:
<221> NAME/KEY: MISC_FEATURE
<222> LOCATION: (4)..(4)
<223> OTHER INFORMATION: CAN BE EITHER Ser OR Thr
<220> FEATURE:
<221> NAME/KEY: MISC_FEATURE
<222> LOCATION: (5)..(5)
<223> OTHER INFORMATION: CAN BE EITHER Ile OR Val OR Ala OR Met

<400> SEQUENCE: 4

Xaa Xaa Val Xaa Xaa
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic polypeptide leader sequence
<220> FEATURE:
<221> NAME/KEY: MISC_FEATURE
<222> LOCATION: (1)..(1)
<223> OTHER INFORMATION: CAN BE EITHER Phe OR Trp OR Tyr
<220> FEATURE:
<221> NAME/KEY: MISC_FEATURE
<222> LOCATION: (2)..(2)
<223> OTHER INFORMATION: CAN BE EITHER Ile OR Leu OR Val OR Ala OR Met
<220> FEATURE:
<221> NAME/KEY: MISC_FEATURE
<222> LOCATION: (3)..(3)
<223> OTHER INFORMATION: CAN BE EITHER Leu OR Val OR Ala OR Met
<220> FEATURE:
<221> NAME/KEY: MISC_FEATURE
<222> LOCATION: (5)..(5)
<223> OTHER INFORMATION: CAN BE EITHER Ile OR Val OR Ala OR Met

<400> SEQUENCE: 5

Xaa Xaa Xaa Ser Xaa
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic polypeptide leader sequence
<220> FEATURE:
<221> NAME/KEY: MISC_FEATURE
<222> LOCATION: (1)..(1)
<223> OTHER INFORMATION: CAN BE EITHER Phe OR Trp OR Tyr
<220> FEATURE:
<221> NAME/KEY: MISC_FEATURE
<222> LOCATION: (2)..(2)
<223> OTHER INFORMATION: CAN BE EITHER Ile OR Leu OR Val OR Ala OR Met
<220> FEATURE:
<221> NAME/KEY: MISC_FEATURE
<222> LOCATION: (3)..(3)
<223> OTHER INFORMATION: CAN BE EITHER Leu OR Val OR Ala OR Met
<220> FEATURE:
```

```
<221> NAME/KEY: MISC_FEATURE
<222> LOCATION: (4)..(4)
<223> OTHER INFORMATION: CAN BE EITHER Ser OR Thr

<400> SEQUENCE: 6

Xaa Xaa Xaa Xaa Ile
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic polypeptide leader sequence

<400> SEQUENCE: 7

Phe Ile Val Ser Ile
1               5

<210> SEQ ID NO 8
<211> LENGTH: 4
<212> TYPE: PRT
<213> ORGANISM: Artificial Sequence
<220> FEATURE:
<223> OTHER INFORMATION: Synthetic polypeptide secretion pre-sequence

<400> SEQUENCE: 8

Met Lys Trp Val
1

<210> SEQ ID NO 9
<211> LENGTH: 9
<212> TYPE: PRT
<213> ORGANISM: Artificial Sequence
<220> FEATURE:
<223> OTHER INFORMATION: Synthetic polypeptide secretion pre-sequence

<400> SEQUENCE: 9

Leu Phe Leu Phe Ser Ser Ala Tyr Ser
1               5

<210> SEQ ID NO 10
<211> LENGTH: 10
<212> TYPE: PRT
<213> ORGANISM: Artificial Sequence
<220> FEATURE:
<223> OTHER INFORMATION: Synthetic polypeptide secretion pre-sequence
<220> FEATURE:
<221> NAME/KEY: MISC_FEATURE
<222> LOCATION: (1)..(1)
<223> OTHER INFORMATION: CAN BE EITHER Ile OR Leu OR Val OR Ala OR Met
<220> FEATURE:
<221> NAME/KEY: MISC_FEATURE
<222> LOCATION: (2)..(2)
<223> OTHER INFORMATION: CAN BE EITHER Phe OR Trp OR Tyr
<220> FEATURE:
<221> NAME/KEY: MISC_FEATURE
<222> LOCATION: (3)..(3)
<223> OTHER INFORMATION: CAN BE EITHER Ile OR Leu OR Val OR Ala OR Met
<220> FEATURE:
<221> NAME/KEY: MISC_FEATURE
<222> LOCATION: (4)..(4)
<223> OTHER INFORMATION: CAN BE EITHER Phe OR Trp OR Tyr
<220> FEATURE:
<221> NAME/KEY: MISC_FEATURE
<222> LOCATION: (5)..(5)
<223> OTHER INFORMATION: CAN BE EITHER Ser OR Thr OR Gly OR Tyr OR Ala
<220> FEATURE:
<221> NAME/KEY: MISC_FEATURE
<222> LOCATION: (6)..(6)
<223> OTHER INFORMATION: CAN BE EITHER Ser OR Thr OR Gly OR Tyr OR Ala
<220> FEATURE:
```

```
<221> NAME/KEY: MISC_FEATURE
<222> LOCATION: (7)..(7)
<223> OTHER INFORMATION: CAN BE EITHER Ile OR Leu OR Val OR Ala OR Met
<220> FEATURE:
<221> NAME/KEY: MISC_FEATURE
<222> LOCATION: (8)..(8)
<223> OTHER INFORMATION: CAN BE EITHER Phe OR Trp OR Tyr
<220> FEATURE:
<221> NAME/KEY: MISC_FEATURE
<222> LOCATION: (9)..(9)
<223> OTHER INFORMATION: CAN BE EITHER Ser OR Thr OR Gly ORTyr OR Ala
<220> FEATURE:
<221> NAME/KEY: misc_feature
<222> LOCATION: (10)..(10)
<223> OTHER INFORMATION: Xaa can be any naturally occurring amino acid

<400> SEQUENCE: 10

Xaa Xaa Xaa Xaa Xaa Xaa Xaa Xaa Xaa Xaa
1               5                   10

<210> SEQ ID NO 11
<211> LENGTH: 15
<212> TYPE: PRT
<213> ORGANISM: Artificial Sequence
<220> FEATURE:
<223> OTHER INFORMATION: Synthetic polypeptide secretion pre-sequence

<400> SEQUENCE: 11

Leu Phe Leu Phe Ser Ser Ala Tyr Ser Arg Ser Leu Asp Lys Arg
1               5                   10                  15

<210> SEQ ID NO 12
<211> LENGTH: 18
<212> TYPE: PRT
<213> ORGANISM: Artificial Sequence
<220> FEATURE:
<223> OTHER INFORMATION: Synthetic polypeptide secretion pre-sequence
<220> FEATURE:
<221> NAME/KEY: MISC_FEATURE
<222> LOCATION: (5)..(5)
<223> OTHER INFORMATION: any amino acid PREFERABLY Phe
<220> FEATURE:
<221> NAME/KEY: MISC_FEATURE
<222> LOCATION: (6)..(6)
<223> OTHER INFORMATION: any amino acid PREFERABLY Ile
<220> FEATURE:
<221> NAME/KEY: MISC_FEATURE
<222> LOCATION: (7)..(7)
<223> OTHER INFORMATION: any amino acid PREFERABLY Val
<220> FEATURE:
<221> NAME/KEY: MISC_FEATURE
<222> LOCATION: (8)..(8)
<223> OTHER INFORMATION: any amino acid PREFERABLY Ser OR Thr
<220> FEATURE:
<221> NAME/KEY: MISC_FEATURE
<222> LOCATION: (9)..(9)
<223> OTHER INFORMATION: any amino acid PREFERABLY Ile

<400> SEQUENCE: 12

Met Lys Trp Val Xaa Xaa Xaa Xaa Xaa Leu Phe Leu Phe Ser Ser Ala
1               5                   10                  15

Tyr Ser

<210> SEQ ID NO 13
<211> LENGTH: 18
<212> TYPE: PRT
<213> ORGANISM: Artificial Sequence
<220> FEATURE:
<223> OTHER INFORMATION: Synthetic polypeptide secretion pre-sequence
<220> FEATURE:
<221> NAME/KEY: MISC_FEATURE
<222> LOCATION: (5)..(5)
<223> OTHER INFORMATION: any amino acid PREFERABLY Phe
```

```
<220> FEATURE:
<221> NAME/KEY: MISC_FEATURE
<222> LOCATION: (6)..(6)
<223> OTHER INFORMATION: any amino acid PREFERABLY Ile
<220> FEATURE:
<221> NAME/KEY: MISC_FEATURE
<222> LOCATION: (7)..(7)
<223> OTHER INFORMATION: any amino acid PREFERABLY Val
<220> FEATURE:
<221> NAME/KEY: MISC_FEATURE
<222> LOCATION: (8)..(8)
<223> OTHER INFORMATION: any amino acid PREFERABLY Ser OR Thr
<220> FEATURE:
<221> NAME/KEY: MISC_FEATURE
<222> LOCATION: (9)..(9)
<223> OTHER INFORMATION: any amino acid PREFERABLY Ile

<400> SEQUENCE: 13

Met Lys Trp Val Xaa Xaa Xaa Xaa Xaa Ile Phe Ile Phe Ser Ser Ile
1               5                   10                  15

Phe Ser

<210> SEQ ID NO 14
<211> LENGTH: 24
<212> TYPE: PRT
<213> ORGANISM: Artificial Sequence
<220> FEATURE:
<223> OTHER INFORMATION: Synthetic polypeptide secretion pre-sequence
<220> FEATURE:
<221> NAME/KEY: MISC_FEATURE
<222> LOCATION: (5)..(5)
<223> OTHER INFORMATION: any amino acid PREFERABLY Phe
<220> FEATURE:
<221> NAME/KEY: MISC_FEATURE
<222> LOCATION: (6)..(6)
<223> OTHER INFORMATION: any amino acid PREFERABLY Ile
<220> FEATURE:
<221> NAME/KEY: MISC_FEATURE
<222> LOCATION: (7)..(7)
<223> OTHER INFORMATION: any amino acid PREFERABLY Val
<220> FEATURE:
<221> NAME/KEY: MISC_FEATURE
<222> LOCATION: (8)..(8)
<223> OTHER INFORMATION: any amino acid PREFERABLY Ser OR Thr
<220> FEATURE:
<221> NAME/KEY: MISC_FEATURE
<222> LOCATION: (9)..(9)
<223> OTHER INFORMATION: any amino acid PREFERABLY Ile

<400> SEQUENCE: 14

Met Lys Trp Val Xaa Xaa Xaa Xaa Xaa Leu Phe Leu Phe Ser Ser Ala
1               5                   10                  15

Tyr Ser Arg Ser Leu Asp Lys Arg
            20

<210> SEQ ID NO 15
<211> LENGTH: 15
<212> TYPE: DNA
<213> ORGANISM: Artificial Sequence
<220> FEATURE:
<223> OTHER INFORMATION: Synthetic oligonucleotide leader sequence
<220> FEATURE:
<221> NAME/KEY: misc_feature
<222> LOCATION: (2)..(3)
<223> OTHER INFORMATION: CAN BE EITHER ty OR gg OR ay
<220> FEATURE:
<221> NAME/KEY: misc_feature
<222> LOCATION: (4)..(6)
<223> OTHER INFORMATION: CAN BE EITHER ath OR ttr OR cta OR ctg OR ctc
      OR ctt OR gta OR gtg OR gtc OR gtt OR gca OR gcg OR gcc OR gct OR
      atg
<220> FEATURE:
<221> NAME/KEY: misc_feature
<222> LOCATION: (7)..(9)
```

```
<223> OTHER INFORMATION: CAN BE EITHER ttr OR cta OR ctg OR ctc OR ctt
      OR gta OR gtg OR gtc OR gtt OR gca OR gcg OR gcc OR gct OR atg
<220> FEATURE:
<221> NAME/KEY: misc_feature
<222> LOCATION: (10)..(12)
<223> OTHER INFORMATION: CAN BE EITHER agy OR tca OR tcg OR tcc OR tct
      OR aca OR acg OR acc OR act
<220> FEATURE:
<221> NAME/KEY: misc_feature
<222> LOCATION: (13)..(15)
<223> OTHER INFORMATION: CAN BE EITHER ath OR cta OR ctg OR ctc OR ctt
      OR gta OR gtg OR gtc OR gtt OR gca OR gcg OR gcc OR gct OR atg

<400> SEQUENCE: 15
tnnnnnnnnn nnnnn                                                    15

<210> SEQ ID NO 16
<211> LENGTH: 15
<212> TYPE: DNA
<213> ORGANISM: Artificial Sequence
<220> FEATURE:
<223> OTHER INFORMATION: Synthetic oligonucleotide leader sequence
<220> FEATURE:
<221> NAME/KEY: misc_feature
<222> LOCATION: (9)..(9)
<223> OTHER INFORMATION: CAN BE EITHER a OR g OR c OR t
<220> FEATURE:
<221> NAME/KEY: misc_feature
<222> LOCATION: (10)..(12)
<223> OTHER INFORMATION: CAN BE EITHER tca OR tcg OR tcc OR tct OR agy

<400> SEQUENCE: 16
ttyathgtnn nnath                                                    15

<210> SEQ ID NO 17
<211> LENGTH: 15
<212> TYPE: DNA
<213> ORGANISM: Artificial Sequence
<220> FEATURE:
<223> OTHER INFORMATION: Synthetic oligonucleotide leader sequence
<220> FEATURE:
<221> NAME/KEY: misc_feature
<222> LOCATION: (2)..(3)
<223> OTHER INFORMATION: CAN BE EITHER tc OR gg OR ac
<220> FEATURE:
<221> NAME/KEY: misc_feature
<222> LOCATION: (4)..(6)
<223> OTHER INFORMATION: CAN BE EITHER aty OR ttg OR gty OR gct OR atg
<220> FEATURE:
<221> NAME/KEY: misc_feature
<222> LOCATION: (7)..(9)
<223> OTHER INFORMATION: CAN BE EITHER ttg OR gty OR gct OR atg
<220> FEATURE:
<221> NAME/KEY: misc_feature
<222> LOCATION: (10)..(10)
<223> OTHER INFORMATION: CAN BE EITHER t OR a
<220> FEATURE:
<221> NAME/KEY: misc_feature
<222> LOCATION: (11)..(15)
<223> OTHER INFORMATION: CAN BE EITHER aty OR gty OR gct OR atg

<400> SEQUENCE: 17
tnnnnnnnnn cynnn                                                    15

<210> SEQ ID NO 18
<211> LENGTH: 15
<212> TYPE: DNA
<213> ORGANISM: Artificial Sequence
<220> FEATURE:
<223> OTHER INFORMATION: Synthetic oligonucleotide leader sequence

<400> SEQUENCE: 18
ttcatygtyt cyaty                                                    15
```

<210> SEQ ID NO 19
<211> LENGTH: 1865
<212> TYPE: DNA
<213> ORGANISM: Artificial Sequence
<220> FEATURE:
<223> OTHER INFORMATION: s. cerevisiae 5'UTR and synthetic
      oligonucleotide leader sequence and mature human albumin CDS

<400> SEQUENCE: 19

```
aagcttaacc taattctaac aagcaaagat gaagtgggtt ttcatcgtct ccatttttgtt      60
cttgttctcc tctgcttact ctagatcttt ggataagaga gacgctcaca agtccgaagt     120
cgctcacaga ttcaaggact tgggtgaaga aaacttcaag gctttggtct tgatcgcttt     180
cgctcaatac ttgcaacaat gtccattcga agatcacgtc aagttggtca acgaagttac     240
cgaattcgct aagacttgtg ttgctgacga atctgctgaa aactgtgaca gtccttgca      300
caccttgttc ggtgataagt tgtgtactgt tgctaccttg agagaaacct acggtgaaat     360
ggctgactgt tgtgctaagc aagaaccaga agaaacgaa tgtttcttgc aacacaagga      420
cgacaaccca aacttgccaa gattggttag accagaagtt gacgtcatgt gtactgcttt     480
ccacgacaac gaagaaacct tcttgaagaa gtacttgtac gaaattgcta agacacccc      540
atacttctac gctccagaat tgttgttctt cgctaagaga tacaaggctg ctttcaccga     600
atgttgtcaa gctgctgata aggctgcttg tttgttgcca aagttggatg aattgagaga     660
cgaaggtaag gcttcttccg ctaagcaaag attgaagtgt gcttccttgc aaaagttcgg     720
tgaaagagct ttcaaggctt gggctgtcgc tagattgtct caaagattcc caaaggctga     780
attcgctgaa gtttctaagt tggttactga cttgactaag gttcacactg aatgttgtca     840
cggtgacttg ttggaatgtg ctgatgacag agctgacttg gctaagtaca tctgtgaaaa     900
ccaagactct atctcttcca gttgaagga atgttgtgaa aagccattgt tggaaaagtc      960
tcactgtatt gctgaagttg aaaacgatga aatgccagct gacttgccat cttttggctgc  1020
tgacttcgtt gaatctaagg acgttttgtaa gaactacgct gaagctaagg acgtcttctt    1080
gggtatgttc ttgtacgaat acgctagaag acacccagac tactccgttg tcttgttgt     1140
gagattggct aagacctacg aaactacctt ggaaaagtgt tgtgctgctg ctgacccaca    1200
cgaatgttac gctaaggttt tcgatgaatt caagccattg gtcgaagaac acaaaaactt    1260
gatcaagcaa aactgtgaat tgttcgaaca attgggtgaa tacaagttcc aaaacgcttt    1320
gttggttaga tacactaaga aggtcccaca agtctccacc ccaactttgg ttgaagtctc    1380
tagaaacttg ggtaaggtcg gttctaagtg ttgtaagcac ccagaagcta agagaatgcc    1440
atgtgctgaa gattacttgt ccgtcgtttt gaaccaattg tgtgttttgc acgaaaagac    1500
cccagtctct gatagagtca ccaagtgttg tactgaatct ttggttaaca aagaccatg     1560
tttctctgct ttggaagtcg acgaaactta cgttccaaag gaattcaacg ctgaaactttt   1620
caccttccac gctgatatct gtaccttgtc cgaaaaggaa agacaaatta agaagcaaac    1680
tgctttggtt gaattggtca agcacaagcc aaaggctact aaggaacaat gaaggctgt     1740
catggatgat ttcgctgctt cgttgaaaaa gtgttgtaag gctgatgata ggaaacttg     1800
tttcgctgaa gaaggtaaga agttggtcgc tgcttcccaa gctgctttgg gtttgtaata   1860
agctt                                                                1865
```

<210> SEQ ID NO 20
<211> LENGTH: 1773
<212> TYPE: DNA

<213> ORGANISM: Artificial Sequence
<220> FEATURE:
<223> OTHER INFORMATION: A mature human albumin coding region

<400> SEQUENCE: 20

| | | | | | |
|---|---|---|---|---|---|
| agatctttgg | ataagagaga | cgctcacaag | tccgaagtcg | ctcacagatt | caaggacttg | 60 |
| ggtgaagaaa | acttcaaggc | tttggtcttg | atcgctttcg | ctcaatactt | gcaacaatgt | 120 |
| ccattcgaag | atcacgtcaa | gttggtcaac | gaagttaccg | aattcgctaa | gacttgtgtt | 180 |
| gctgacgaat | ctgctgaaaa | ctgtgacaag | tccttgcaca | ccttgttcgg | tgataagttg | 240 |
| tgtactgttg | ctaccttgag | agaaacctac | ggtgaaatgg | ctgactgttg | tgctaagcaa | 300 |
| gaaccagaaa | gaaacgaatg | tttcttgcaa | cacaaggacg | acaacccaaa | cttgccaaga | 360 |
| ttggttagac | agaagttgac | cgtcatgtgt | actgctttcc | acgacaacga | agaaaccttc | 420 |
| ttgaagaagt | acttgtacga | aattgctaga | agacacccat | acttctacgc | tccagaattg | 480 |
| ttgttcttcg | ctaagagata | caaggctgct | ttcaccgaat | gttgtcaagc | tgctgataag | 540 |
| gctgcttgtt | tgttgccaaa | gttggatgaa | ttgagagacg | aaggtaaggc | ttcttccgct | 600 |
| aagcaaagat | tgaagtgtgc | ttccttgcaa | aagttcggtg | aaagagcttt | caaggcttgg | 660 |
| gctgtcgcta | gattgtctca | aagattccca | aaggctgaat | cgctgaagt | ttctaagttg | 720 |
| gttactgact | tgactaaggt | tcacactgaa | tgttgtcacg | gtgacttgtt | ggaatgtgct | 780 |
| gatgacagag | ctgacttggc | taagtacatc | tgtgaaaacc | aagactctat | ctcttccaag | 840 |
| ttgaaggaat | gttgtgaaaa | gccattgttg | gaaaagtctc | actgtattgc | tgaagttgaa | 900 |
| aacgatgaaa | tgccagctga | cttgccatct | ttggctgctg | acttcgttga | atctaaggac | 960 |
| gtttgtaaga | actacgctga | agctaaggac | gtcttcttgg | gtatgttctt | gtacgaatac | 1020 |
| gctagaagac | acccagacta | ctccgttgtc | ttgttgttga | gattggctaa | gacctacgaa | 1080 |
| actaccttgg | aaaagtgttg | tgctgctgct | gacccacacg | aatgttacgc | taaggttttc | 1140 |
| gatgaattca | agccattggt | cgaagaacca | caaaacttga | tcaagcaaaa | ctgtgaattg | 1200 |
| ttcgaacaat | tgggtgaata | caagttccaa | aacgctttgt | tggttagata | cactaagaag | 1260 |
| gtcccacaag | tctccacccc | aactttggtt | gaagtctcta | gaaacttggg | taaggtcggt | 1320 |
| tctaagtgtt | gtaagcaccc | agaagctaag | agaatgccat | gtgctgaaga | ttacttgtcc | 1380 |
| gtcgtttga | accaattgtg | tgttttgcac | gaaaagaccc | cagtctctga | tagagtcacc | 1440 |
| aagtgttgta | ctgaatcttt | ggttaacaga | agaccatgtt | tctctgcttt | ggaagtcgac | 1500 |
| gaaacttacg | ttccaaagga | attcaacgct | gaaactttca | ccttccacgc | tgatatctgt | 1560 |
| accttgtccg | aaaaggaaag | acaaattaag | aagcaaactg | ctttggttga | attggtcaag | 1620 |
| cacaagccaa | aggctactaa | ggaacaattg | aaggctgtca | tggatgattt | cgctgctttc | 1680 |
| gttgaaaagt | gttgtaaggc | tgatgataag | gaaacttgtt | tcgctgaaga | aggtaagaag | 1740 |
| ttggtcgctg | cttcccaagc | tgctttgggt | ttg | | | 1773 |

<210> SEQ ID NO 21
<211> LENGTH: 1827
<212> TYPE: DNA
<213> ORGANISM: Artificial Sequence
<220> FEATURE:
<223> OTHER INFORMATION: Synthetic oligonucleotide leader sequence and protein coding region

<400> SEQUENCE: 21

| | | | | | |
|---|---|---|---|---|---|
| atgaagtggg | ttttcatcgt | ctccattttg | ttcttgttct | cctctgctta | ctctagatct | 60 |
| ttggataaga | gagacgctca | caagtccgaa | gtcgctcaca | gattcaagga | cttgggtgaa | 120 |

```
gaaaacttca aggctttggt cttgatcgct ttcgctcaat acttgcaaca atgtccattc    180
gaagatcacg tcaagttggt caacgaagtt accgaattcg ctaagacttg tgttgctgac    240
gaatctgctg aaaactgtga caagtccttg cacaccttgt tcggtgataa gttgtgtact    300
gttgctacct tgagagaaac ctacggtgaa atggctgact gttgtgctaa gcaagaacca    360
gaaagaaacg aatgtttctt gcaacacaag gacgacaacc caaacttgcc aagattggtt    420
agaccagaag ttgacgtcat gtgtactgct ttccacgaca acgaagaaac cttcttgaag    480
aagtacttgt acgaaattgc tagaagacac ccatacttct acgctccaga attgttgttc    540
ttcgctaaga gatacaaggc tgctttcacc gaatgttgtc aagctgctga taaggctgct    600
tgtttgttgc caaagttgga tgaattgaga gacgaaggta aggcttcttc cgctaagcaa    660
agattgaagt gtgcttcctt gcaaaagttc ggtgaaagag ctttcaaggc ttgggctgtc    720
gctagattgt ctcaaagatt cccaaaggct gaattcgctg aagtttctaa gttggttact    780
gacttgacta aggttcacac tgaatgttgt cacggtgact gttggaaatg tgctgatgac    840
agagctgact ggctaagta catctgtgaa aaccaagact ctatctcttc caagttgaag    900
gaatgttgtg aaaagccatt gttggaaaag tctcactgta ttgctgaagt tgaaaacgat    960
gaaatgccag ctgacttgcc atcttttggct gctgacttcg ttgaatctaa ggacgtttgt   1020
aagaactacg ctgaagctaa ggacgtcttc ttgggtatgt tcttgtacga atacgctaga   1080
agacacccag actactccgt tgtcttgttg ttgagattgg ctaagaccta cgaaactacc   1140
ttggaaaagt gttgtgctgc tgctgaccca cacgaatgtt acgctaaggt tttcgatgaa   1200
ttcaagccat tggtcgaaga accacaaaac ttgatcaagc aaaactgtga attgttcgaa   1260
caattgggtg aatacaagtt ccaaaacgct tgttggtta gatacactaa gaaggtccca   1320
caagtctcca ccccaacttt ggttgaagtc tctagaaact tgggtaaggt cggttctaag   1380
tgttgtaagc acccagaagc taagagaatg ccatgtgctg aagattactt gtccgtcgtt   1440
ttgaaccaat gtgtgttttt gcacgaaaag acccccagtct ctgatagagt caccaagtgt   1500
tgtactgaat ctttggttaa cagaagacca tgtttctctg ctttggaagt cgacgaaact   1560
tacgttccaa aggaattcaa cgctgaaact ttcaccttcc acgctgatat ctgtaccttg   1620
tccgaaaagg aaagacaaat taagaagcaa actgctttgg ttgaattggt caagcacaag   1680
ccaaaggcta ctaaggaaca attgaaggct gtcatggatg atttcgctgc tttcgttgaa   1740
aagtgttgta aggctgatga taaggaaact tgtttcgctg aagaaggtaa gaagttggtc   1800
gctgcttccc aagctgcttt gggtttg                                       1827
```

<210> SEQ ID NO 22
<211> LENGTH: 1827
<212> TYPE: DNA
<213> ORGANISM: Artificial Sequence
<220> FEATURE:
<223> OTHER INFORMATION: Synthetic oligonucleotide leader sequence and the mature human albumin coding region

<400> SEQUENCE: 22

```
atgaagtggg taagctttat ttcccttctt tttctcttta gctcggctta ttccaggagc     60
ttggataaaa gagatgcaca caagagtgag gttgctcatc ggtttaaaga tttgggagaa    120
gaaaatttca agccttggt gttgattgcc tttgctcagt atcttcagca gtgtccattt     180
gaagatcatg taaaattagt gaatgaagta actgaatttg caaaaacatg tgttgctgat    240
gagtcagctg aaaattgtga caaatcactt catacccttt ttggagacaa attatgcaca    300
```

| | |
|---|---|
| gttgcaactc ttcgtgaaac ctatggtgaa atggctgact gctgtgcaaa acaagaacct | 360 |
| gagagaaatg aatgcttctt gcaacacaaa gatgacaacc caaacctccc ccgattggtg | 420 |
| agaccagagg ttgatgtgat gtgcactgct tttcatgaca atgaagagac atttttgaaa | 480 |
| aaatacttat atgaaattgc cagaagacat ccttactttt atgccccgga actccttttc | 540 |
| tttgctaaaa ggtataaagc tgcttttaca gaatgttgcc aagctgctga taaagctgcc | 600 |
| tgcctgttgc aaagctcga tgaacttcgg gatgaaggga aggcttcgtc tgccaaacag | 660 |
| agactcaagt gtgccagtct ccaaaaattt ggagaaagag ctttcaaagc atgggcagta | 720 |
| gctcgcctga ccagagatt tcccaaagct gagtttgcag aagtttccaa gttagtgaca | 780 |
| gatcttacca aagtccacac ggaatgctgc catggagatc tgcttgaatg tgctgatgac | 840 |
| agggcggacc ttgccaagta tatctgtgaa aatcaagatt cgatctccag taaactgaag | 900 |
| gaatgctgtg aaaaacctct gttggaaaaa tcccactgca ttgccgaagt ggaaaatgat | 960 |
| gagatgcctg ctgacttgcc ttcattagct gctgattttg ttgaaagtaa ggatgtttgc | 1020 |
| aaaaactatg ctgaggcaaa ggatgtcttc ctgggcatgt ttttgtatga atatgcaaga | 1080 |
| aggcatcctg attactctgt cgtgctgctg ctgagacttg ccaagacata tgaaaccact | 1140 |
| ctagagaagt gctgtgccgc tgcagatcct catgaatgct atgccaaagt gttcgatgaa | 1200 |
| tttaaacctc ttgtggaaga gcctcagaat ttaatcaaac aaaattgtga gcttttttgag | 1260 |
| cagcttggag agtacaaatt ccagaatgcg ctattagttc gttacaccaa gaaagtaccc | 1320 |
| caagtgtcaa ctccaactct tgtagaggtc tcaagaaacc taggaaaagt gggcagcaaa | 1380 |
| tgttgtaaac atcctgaagc aaaaagaatg ccctgtgcag aagactatct atccgtggtc | 1440 |
| ctgaaccagt tatgtgtgtt gcatgagaaa acgccagtaa gtgacagagt caccaaaatgc | 1500 |
| tgcacagaat ccttggtgaa caggcgacca tgcttttcag ctctggaagt cgatgaaaca | 1560 |
| tacgttccca agagtttaa tgctgaaaca ttcaccttcc atgcagatat atgcacactt | 1620 |
| tctgagaagg agagacaaat caagaaacaa actgcacttg ttgagctcgt gaaacacaag | 1680 |
| cccaaggcaa caaaagagca actgaaagct gttatggatg atttcgcagc ttttgtagag | 1740 |
| aagtgctgca aggctgacga taaggagacc tgctttgccg aggagggtaa aaaacttgtt | 1800 |
| gctgcaagtc aagctgcctt aggctta | 1827 |

```
<210> SEQ ID NO 23
<211> LENGTH: 47
<212> TYPE: DNA
<213> ORGANISM: Artificial Sequence
<220> FEATURE:
<223> OTHER INFORMATION: Synthetic oligonucleotide leader sequence

<400> SEQUENCE: 23
```

| | |
|---|---|
| ctaaagagaa aaagaatgga gacgatgaat acccacttca tctttgc | 47 |

```
<210> SEQ ID NO 24
<211> LENGTH: 72
<212> TYPE: DNA
<213> ORGANISM: Artificial Sequence
<220> FEATURE:
<223> OTHER INFORMATION: Synthetic oligonucleotide leader sequence

<400> SEQUENCE: 24
```

| | |
|---|---|
| atgaagtggg tattcatcgt ctccattctt tttctcttta gctcggctta ttccaggagc | 60 |
| ttggataaaa ga | 72 |

```
<210> SEQ ID NO 25
```

<211> LENGTH: 1827
<212> TYPE: DNA
<213> ORGANISM: Artificial Sequence
<220> FEATURE:
<223> OTHER INFORMATION: Synthetic oligonucleotide leader sequence and mature human albumin coding region

<400> SEQUENCE: 25

| | | | | | |
|---|---|---|---|---|---|
| atgaagtggg | tattcatcgt | ctccattctt | tttctcttta | gctcggctta | ttccaggagc | 60 |
| ttggataaaa | gagatgcaca | caagagtgag | gttgctcatc | ggtttaaaga | tttgggagaa | 120 |
| gaaaatttca | aagccttggt | gttgattgcc | tttgctcagt | atcttcagca | gtgtccattt | 180 |
| gaagatcatg | taaaattagt | gaatgaagta | actgaatttg | caaaaacatg | tgttgctgat | 240 |
| gagtcagctg | aaaattgtga | caaatcactt | catacccttt | ttggagacaa | attatgcaca | 300 |
| gttgcaactc | ttcgtgaaac | ctatggtgaa | atggctgact | gctgtgcaaa | acaagaacct | 360 |
| gagagaaatg | aatgcttctt | gcaacacaaa | gatgacaacc | caaacctccc | ccgattggtg | 420 |
| agaccagagg | ttgatgtgat | gtgcactgct | tttcatgaca | atgaagagac | attttttgaa | 480 |
| aaatacttat | atgaaattgc | cagaagacat | ccttactttt | atgccccgga | actccttttc | 540 |
| tttgctaaaa | ggtataaagc | tgcttttaca | gaatgttgcc | aagctgctga | taaagctgcc | 600 |
| tgcctgttgc | caaagctcga | tgaacttcgg | gatgaaggga | aggcttcgtc | tgccaaacag | 660 |
| agactcaagt | gtgccagtct | ccaaaaattt | ggagaaagag | ctttcaaagc | atgggcagta | 720 |
| gctcgcctga | gccagagatt | tcccaaagct | gagtttgcag | aagtttccaa | gttagtgaca | 780 |
| gatcttacca | aagtccacac | ggaatgctgc | catggagatc | tgcttgaatg | tgctgatgac | 840 |
| agggcggacc | ttgccaagta | tatctgtgaa | aatcaagatt | cgatctccag | taaactgaag | 900 |
| gaatgctgtg | aaaaacctct | gttggaaaaa | tcccactgca | ttgccgaagt | ggaaaatgat | 960 |
| gagatgcctg | ctgacttgcc | ttcattagct | gctgattttg | ttgaaagtaa | ggatgtttgc | 1020 |
| aaaaactatg | ctgaggcaaa | ggatgtcttc | ctgggcatgt | ttttgtatga | atatgcaaga | 1080 |
| aggcatcctg | attactctgt | cgtgctgctg | ctgagacttg | ccaagacata | tgaaaccact | 1140 |
| ctagagaagt | gctgtgccgc | tgcagatcct | catgaatgct | atgccaaagt | gttcgatgaa | 1200 |
| tttaaacctc | ttgtggaaga | gcctcagaat | ttaatcaaac | aaaattgtga | gcttttttgag | 1260 |
| cagcttggag | agtacaaatt | ccagaatgcg | ctattagttc | gttacaccaa | gaaagtaccc | 1320 |
| caagtgtcaa | ctccaactct | tgtagaggtc | tcaagaaacc | taggaaaagt | gggcagcaaa | 1380 |
| tgttgtaaac | atcctgaagc | aaaaagaatg | ccctgtgcag | aagactatct | atccgtggtc | 1440 |
| ctgaaccagt | tatgtgtgtt | gcatgagaaa | acgccagtaa | gtgacagagt | caccaaatgc | 1500 |
| tgcacagaat | ccttggtgaa | caggcgacca | tgcttttcag | ctctggaagt | cgatgaaaca | 1560 |
| tacgttccca | aagagtttaa | tgctgaaaca | ttcaccttcc | atgcagatat | atgcacactt | 1620 |
| tctgagaagg | agagacaaat | caagaaacaa | actgcacttg | ttgagctcgt | gaaacacaag | 1680 |
| cccaaggcaa | caaagagagca | actgaaagct | gttatggatg | atttcgcagc | ttttgtagag | 1740 |
| aagtgctgca | aggctgacga | taaggagacc | tgctttgccg | aggagggtaa | aaaacttgtt | 1800 |
| gctgcaagtc | aagctgcctt | aggctta | | | | 1827 |

<210> SEQ ID NO 26
<211> LENGTH: 1827
<212> TYPE: DNA
<213> ORGANISM: Artificial Sequence
<220> FEATURE:
<223> OTHER INFORMATION: Synthetic oligonucleotide plasmid sequence

<400> SEQUENCE: 26

```
atgaagtggg tttctttcat ttccttgttg ttcttgttct cctctgctta ctctagatct      60
ttggataaga gagacgctca caagtccgaa gtcgctcaca gattcaagga cttgggtgaa     120
gaaaacttca aggctttggt cttgatcgct ttcgctcaat acttgcaaca atgtccattc     180
gaagatcacg tcaagttggt caacgaagtt accgaattcg ctaagacttg tgttgctgac     240
gaatctgctg aaaactgtga caagtccttg cacaccttgt tcggtgataa gttgtgtact     300
gttgctacct tgagagaaac ctacggtgaa atggctgact gttgtgctaa gcaagaacca     360
gaaagaaacg aatgtttctt gcaacacaag gacgacaacc caaacttgcc aagattggtt     420
agaccagaag ttgacgtcat gtgtactgct ttccacgaca cgaagaaac cttcttgaag      480 aagtacttgt acgaaattgc tagaagacac ccatacttct acgctccaga attgttgttc     540
ttcgctaaga gatacaaggc tgctttcacc gaatgttgtc aagctgctga taaggctgct     600
tgtttgttgc caagttgga tgaattgaga gacgaaggta aggcttcttc cgctaagcaa       660
agattgaagt gtgcttcctt gcaaaagttc ggtgaaagag ctttcaaggc ttgggctgtc     720
gctagattgt ctcaaagatt cccaaaggct gaattcgctg aagtttctaa gttggttact     780
gacttgacta aggttcacac tgaatgttgt cacggtgact gttggaatg tgctgatgac      840 agagctgact ggctaagta catctgtgaa aaccaagact ctatctcttc caagttgaag      900
gaatgttgtg aaaagccatt gttggaaaag tctcactgta ttgctgaagt tgaaaacgat     960
gaaatgccag ctgacttgcc atctttggct gctgacttcg ttgaatctaa ggacgtttgt    1020
aagaactacg ctgaagctaa ggacgtcttc ttgggtatgt tcttgtacga atacgctaga    1080
agacacccag actactccgt tgtcttgttg ttgagattgg ctaagaccta cgaaactacc    1140
ttggaaaagt gttgtgctgc tgctgaccca cacgaatgtt acgctaaggt ttcgatgaa     1200 ttcaagccat tggtcgaaga accacaaaac ttgatcaagc aaaactgtga attgttcgaa    1260
caattgggtg aatacaagtt ccaaaacgct tgttggtta gatacactaa gaaggtccca    1320
caagtctcca ccccaacttt ggttgaagtc tctagaaact tgggtaaggt cggttctaag    1380
tgttgtaagc acccagaagc taagagaatg ccatgtgctg aagattactt gtccgtcgtt    1440
ttgaaccaat tgtgtgtttt gcacgaaaag acccagtct ctgatagagt caccaagtgt    1500
tgtactgaat ctttggttaa cagaagacca tgtttctctg cttggaagt cgacgaaact    1560 tacgttccaa aggaattcaa cgctgaaact ttcaccttcc acgctgatat ctgtaccttg    1620
tccgaaaagg aaagacaaat taagaagcaa actgctttgg ttgaattggt caagcacaag    1680
ccaaaggcta ctaaggaaca attgaaggct gtcatggatg atttcgctgc tttcgttgaa    1740
aagtgttgta aggctgatga taaggaaact tgtttcgctg aagaaggtaa aagttggtc     1800 gctgcttccc aagctgcttt gggtttg                                        1827
```

<210> SEQ ID NO 27
<211> LENGTH: 72
<212> TYPE: DNA
<213> ORGANISM: Artificial Sequence
<220> FEATURE:
<223> OTHER INFORMATION: Synthetic oligonucleotide leader sequence

<400> SEQUENCE: 27

```
atgaagtggg ttttcatcgt ctccattttg ttcttgttct cctctgctta ctctagatct      60
ttggataaga ga                                                          72
```

<210> SEQ ID NO 28
<211> LENGTH: 18

```
<212> TYPE: PRT
<213> ORGANISM: Artificial Sequence
<220> FEATURE:
<223> OTHER INFORMATION: Synthetic oligonucleotide secretion
      pre-sequence

<400> SEQUENCE: 28

Met Lys Trp Val Phe Ile Val Ser Ile Leu Phe Leu Phe Ser Ser Ala
1               5                   10                  15

Tyr Ser

<210> SEQ ID NO 29
<211> LENGTH: 5
<212> TYPE: PRT
<213> ORGANISM: Artificial Sequence
<220> FEATURE:
<223> OTHER INFORMATION: Synthetic polypeptide leader sequence
<220> FEATURE:
<221> NAME/KEY: MISC_FEATURE
<222> LOCATION: (1)..(1)
<223> OTHER INFORMATION: CAN BE EITHER Phe OR Trp OR Tyr
<220> FEATURE:
<221> NAME/KEY: MISC_FEATURE
<222> LOCATION: (2)..(2)
<223> OTHER INFORMATION: CAN BE EITHER Ile OR Leu OR Val OR Ala OR Met
<220> FEATURE:
<221> NAME/KEY: MISC_FEATURE
<222> LOCATION: (3)..(3)
<223> OTHER INFORMATION: CAN BE EITHER Leu OR Val OR Ala OR Met
<220> FEATURE:
<221> NAME/KEY: MISC_FEATURE
<222> LOCATION: (5)..(5)
<223> OTHER INFORMATION: CAN BE EITHER Ile OR Val OR Ala OR Met

<400> SEQUENCE: 29

Xaa Xaa Xaa Thr Xaa
1               5

<210> SEQ ID NO 30
<211> LENGTH: 15
<212> TYPE: PRT
<213> ORGANISM: Artificial Sequence
<220> FEATURE:
<223> OTHER INFORMATION: Synthetic polypeptide secretion pre-sequence

<400> SEQUENCE: 30

Leu Phe Leu Phe Ser Ser Ala Tyr Ser Arg Gly Val Phe Arg Arg
1               5                   10                  15

<210> SEQ ID NO 31
<211> LENGTH: 24
<212> TYPE: PRT
<213> ORGANISM: Artificial Sequence
<220> FEATURE:
<223> OTHER INFORMATION: Synthetic polypeptide secretion pre-sequence
<220> FEATURE:
<221> NAME/KEY: MISC_FEATURE
<222> LOCATION: (5)..(5)
<223> OTHER INFORMATION: any amino acid PREFERABLY Phe
<220> FEATURE:
<221> NAME/KEY: MISC_FEATURE
<222> LOCATION: (6)..(6)
<223> OTHER INFORMATION: any amino acid PREFERABLY Ile
<220> FEATURE:
<221> NAME/KEY: MISC_FEATURE
<222> LOCATION: (7)..(7)
<223> OTHER INFORMATION: any amino acid PREFERABLY Val
<220> FEATURE:
<221> NAME/KEY: MISC_FEATURE
<222> LOCATION: (8)..(8)
<223> OTHER INFORMATION: any amino acid PREFERABLY Ser OR Thr
<220> FEATURE:
<221> NAME/KEY: MISC_FEATURE
```

```
<222> LOCATION: (9)..(9)
<223> OTHER INFORMATION: any amino acid PREFERABLY Ile

<400> SEQUENCE: 31

Met Lys Trp Val Xaa Xaa Xaa Xaa Xaa Leu Phe Leu Phe Ser Ser Ala
1               5                   10                  15

Tyr Ser Arg Gly Val Phe Arg Arg
            20

<210> SEQ ID NO 32
<211> LENGTH: 24
<212> TYPE: PRT
<213> ORGANISM: Artificial Sequence
<220> FEATURE:
<223> OTHER INFORMATION: Synthetic polypeptide secretion pre-pro
      sequence

<400> SEQUENCE: 32

Met Lys Trp Val Phe Ile Val Ser Ile Leu Phe Leu Phe Ser Ser Ala
1               5                   10                  15

Tyr Ser Arg Ser Leu Asp Lys Arg
            20

<210> SEQ ID NO 33
<211> LENGTH: 4
<212> TYPE: PRT
<213> ORGANISM: Artificial Sequence
<220> FEATURE:
<223> OTHER INFORMATION: Synthetic polypeptide secretion pre-sequence
<220> FEATURE:
<221> NAME/KEY: MISC_FEATURE
<222> LOCATION: (2)..(2)
<223> OTHER INFORMATION: CAN BE EITHER Lys OR Arg OR His
<220> FEATURE:
<221> NAME/KEY: MISC_FEATURE
<222> LOCATION: (3)..(3)
<223> OTHER INFORMATION: CAN BE EITHER Phe OR Trp OR Tyr
<220> FEATURE:
<221> NAME/KEY: MISC_FEATURE
<222> LOCATION: (4)..(4)
<223> OTHER INFORMATION: CAN BE EITHER Ile OR Leu OR Val OR Ala OR Met

<400> SEQUENCE: 33

Met Xaa Xaa Xaa
1

<210> SEQ ID NO 34
<211> LENGTH: 15
<212> TYPE: DNA
<213> ORGANISM: Artificial Sequence
<220> FEATURE:
<223> OTHER INFORMATION: Synthetic oligonucleotide leader sequence

<400> SEQUENCE: 34
ttcatcgtct ccatt                                                   15

<210> SEQ ID NO 35
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 35
gcatgcggcc gcccgtaatg cggtatcgtg aaagcg                            36

<210> SEQ ID NO 36
<211> LENGTH: 35
```

```
<212> TYPE: DNA
<213> ORGANISM: Artificial Sequence
<220> FEATURE:
<223> OTHER INFORMATION: Synthetic oligonucleotide primer

<400> SEQUENCE: 36
gcataagctt acccacttca tctttgcttg tttag                              35

<210> SEQ ID NO 37
<211> LENGTH: 11
<212> TYPE: DNA
<213> ORGANISM: Artificial Sequence
<220> FEATURE:
<223> OTHER INFORMATION: Synthetic oligonucleotide linker

<400> SEQUENCE: 37
ttaggcttat a                                                        11

<210> SEQ ID NO 38
<211> LENGTH: 12
<212> TYPE: DNA
<213> ORGANISM: Artificial Sequence
<220> FEATURE:
<223> OTHER INFORMATION: Synthetic oligonucleotide linker

<400> SEQUENCE: 38
ccgaatattc ga                                                       12

<210> SEQ ID NO 39
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 39
gttagaatta ggttaagctt gttttttat tggcgatgaa                          40

<210> SEQ ID NO 40
<211> LENGTH: 1865
<212> TYPE: DNA
<213> ORGANISM: Artificial Sequence
<220> FEATURE:
<223> OTHER INFORMATION: s. cerevisiae 5'UTR and synthetic
      oligonucleotide leader sequence and mature human albumin CDS

<400> SEQUENCE: 40
aagcttaacc taattctaac aagcaaagat gaagtgggtt tctttcattt ccttgttgtt    60
cttgttctcc tctgcttact ctagatcttt ggataagaga gacgctcaca agtccgaagt   120
cgctcacaga ttcaaggact gggtgaaga aaacttcaag gctttggtct tgatcgcttt    180
cgctcaatac ttgcaacaat gtccattcga agatcacgtc aagttggtca acgaagttac   240
cgaattcgct aagacttgtg ttgctgacga atctgctgaa aactgtgaca agtccttgca   300
caccttgttc ggtgataagt gtgtgtactgt tgctaccttg agagaaacct acggtgaaat   360
ggctgactgt tgtgctaagc aagaaccaga aagaaacgaa tgtttcttgc aacacaagga   420
cgacaaccca aacttgccaa gattggttag accagaagtt gacgtcatgt gtactgcttt   480
ccacgacaac gaagaaacct tcttgaagaa gtacttgtac gaaattgcta agacaccc     540 atacttctac gctccagaat tgttgttctt cgctaagaga tacaaggctg ctttcaccga   600
atgttgtcaa gctgctgata aggctgcttg tttgttgcca agttggatg aattgagaga    660 cgaaggtaag gcttcttccg ctaagcaaag attgaagtgt gcttccttgc aaaagttcgg   720
```

```
tgaaagagct ttcaaggctt gggctgtcgc tagattgtct caaagattcc caaaggctga    780
attcgctgaa gtttctaagt tggttactga cttgactaag gttcacactg aatgttgtca    840
cggtgacttg ttggaatgtg ctgatgacag agctgacttg gctaagtaca tctgtgaaaa    900
ccaagactct atctcttcca agttgaagga atgttgtgaa aagccattgt tggaaaagtc    960
tcactgtatt gctgaagttg aaaacgatga aatgccagct gacttgccat ctttggctgc   1020
tgacttcgtt gaatctaagg acgtttgtaa gaactacgct gaagctaagg acgtcttctt   1080
gggtatgttc ttgtacgaat acgctagaag acacccagac tactccgttg tcttgttgtt   1140
gagattggct aagacctacg aaactacctt ggaaaagtgt tgtgctgctg ctgacccaca   1200
cgaatgttac gctaaggttt tcgatgaatt caagccattg gtcgaagaac cacaaaactt   1260
gatcaagcaa aactgtgaat tgttcgaaca attgggtgaa tacaagttcc aaaacgcttt   1320
gttggttaga tacactaaga aggtcccaca agtctccacc ccaactttgg ttgaagtctc   1380
tagaaacttg ggtaaggtcg gttctaagtg ttgtaagcac ccagaagcta agagaatgcc   1440
atgtgctgaa gattacttgt ccgtcgtttt gaaccaattg tgtgttttgc acgaaaagac   1500
cccagtctct gatagagtca ccaagtgttg tactgaatct ttggttaaca gaagaccatg   1560
tttctctgct ttggaagtcg acgaaactta cgttccaaag gaattcaacg ctgaaacttt   1620
caccttccac gctgatatct gtaccttgtc cgaaaaggaa agacaaatta agaagcaaac   1680
tgctttggtt gaattggtca agcacaagcc aaaggctact aaggaacaat tgaaggctgt   1740
catggatgat ttcgctgctt tcgttgaaaa gtgttgtaag gctgatgata aggaaacttg   1800
tttcgctgaa gaaggtaaga agttggtcgc tgcttcccaa gctgctttgg gtttgtaata   1860
agctt                                                                 1865
```

GENE AND POLYPEPTIDE SEQUENCES

CROSS-REFERENCE TO RELATED APPLICATIONS

This application is a National Stage application based on International Application No. PCT/GB2003/003273, filed Jul. 23, 2003, which claims priority to Great Britain Application No. GB0217033.0, filed Jul. 22, 2002, the disclosures of which are incorporated herein by reference.

The present invention relates to polypeptide and polynucleotide sequences for secreting proteins from host cells.

Numerous natural or artificial polypeptide signal sequences (also called secretion pre regions) have been used or developed for secreting desired peptides, polypeptides and proteins (these terms are used interchangeably from hereon in) from host cells. The signal sequence directs the nascent protein towards the machinery of the cell that exports proteins from the cell into the surrounding medium or, in some cases, into the periplasmic space. The signal sequence is usually, although not necessarily, located at the N-terminus of the primary translation product and is generally, although not necessarily, cleaved off the desired protein during the secretion process, to yield the "mature" protein.

In the case of some desired proteins the entity that is initially secreted, after the removal of the signal sequence, includes additional amino acids at its N-terminus called a "pro" sequence, the intermediate entity being called a "pro-protein". These pro sequences may assist the final protein to fold and become functional, and are usually then cleaved off. In other instances, the pro region simply provides a cleavage site for an enzyme to cleave off the pre-pro region and is not known to have another function.

The pro sequence can be removed either during the secretion of the desired protein from the cell or after export from the cell into the surrounding medium or periplasmic space.

Polypeptide sequences which direct the secretion of proteins, whether they resemble signal (i.e. pre) sequences or pre-pro secretion sequences, are sometimes also referred to as leader sequences. The secretion of proteins is a dynamic process involving translation, translocation and post-translational processing, and one or more of these steps may not necessarily be completed before another is either initiated or completed.

For production of proteins in eukaryotic species such as the yeasts *Saccharomyces cerevisiae* and *Pichia pastoris*, known leader sequences include those from the *S. cerevisiae* acid phosphatase protein (Pho5p) (see EP 366 400), the invertase-protein (Suc2p) (see Smith et al. (1985) *Science*, 229, 1219-1224) and heat-shock protein-150 (Hsp150p) (see WO 95/33833). Additionally, leader sequences from the *S. cerevisiae* mating factor alpha-1 protein (MFα-1) and from the human lysozyme and human serum albumin (HSA) protein have been used, the latter having been used especially, although not exclusively, for secreting human albumin. WO 90/01063 discloses a fusion of the MFα-1 and HSA leader sequences, which advantageously reduces the production of a contaminating fragment of human albumin relative to the use of the MFα-1 leader sequence.

Unexpectedly, we have found that the yield of secreted protein can be increased by the introduction of an amino acid sequence motif, preferably by modification of leader sequences. The modifications are effective whether made to the complete native albumin leader sequence, variants thereof, or to other leader sequences that employ the relevant part of the human albumin leader sequence, such as the fusion of MFα-1 and HSA leader sequences as disclosed in WO 90/01063. In the latter case, if albumin is the protein secreted, the albumin thus produced retains the advantageous feature of reduced contaminating fragment, whilst still increasing the yield.

Although conservative modifications of the fused leader sequence of WO 90/01063 were disclosed in general terms in WO 90/01063 (for example, see page 8 of WO 90/01063), this resulted in a class of some $8 \times 10^{12}$ polypeptides being defined. Polynucleotide coding sequences were set out for the exemplified leader sequence, according to the degeneracy of the genetic code. This also represents a large number of possibilities. There is no appreciation in WO 90/01063 that the specific class of modified leader sequences provided by the present invention would have advantageous properties for expression of secreted protein.

In a first aspect of the present invention there is provided a polypeptide comprising (i) a leader sequence, the leader sequence comprising (a) a secretion pre sequence and (b) the following motif:

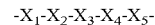

where $X_1$ is phenylalanine, tryptophan, or tyrosine, $X_2$ is isoleucine, leucine, valine, alanine or methionine, $X_3$ is leucine, valine, alanine or methionine, $X_4$ is serine or threonine and $X_5$ is isoleucine, valine, alanine or methionine; and (ii) a desired protein, heterologous to the leader sequence.

In other words, the polypeptide includes a sequence according to SEQ ID NO 1—

```
                                          SEQ ID No 1
N-(Phe/Trp/Tyr)-(Ile/Leu/Val/Ala/Met)-(Leu/Val/
Ala/Met)-(Ser/Thr)-(Ile/Val/Ala/Met)-C
```

In a preferred embodiment of the first aspect of the present invention, $X_1$ is phenylalanine. Thus a preferred polypeptide includes the sequence of SEQ ID NO 2—

```
                                          SEQ ID No 2
N-Phe-(Ile/Leu/Val/Ala/Met)-(Leu/Val/Ala/Met)-
(Ser/Thr)-(Ile/Val/Ala/Met)-C
```

In another preferred embodiment of the first aspect of the present invention, $X_2$ is isoleucine. Thus another preferred polypeptide includes the sequence of SEQ ID NO 3—

```
                                          SEQ ID No 3
N-(Phe/Trp/Tyr)-Ile-(Leu/Val/Ala/Met)-(Ser/Thr)-
(Ile/Val/Ala/Met)-C
```

In another preferred embodiment of the first aspect of the present invention, $X_3$ is valine. Thus another preferred polypeptide includes the sequence of SEQ ID NO 4—

```
                                          SEQ ID No 4
N-(Phe/Trp/Tyr)-(Ile/Leu/Val/Ala/Met)-Val-(Ser/
Thr)-(Ile/Val/Ala/Met)-C
```

In another preferred polypeptide $X_4$ is serine and so includes the sequence of SEQ ID NO 5—

```
                                          SEQ ID No 5
N-(Phe/Trp/Tyr)-(Ile/Leu/Val/Ala/Met)-(Leu/Val/
Ala/Met)-Ser-(Ile/Val/Ala/Met)-C
```

In another preferred embodiment of the first aspect of the present invention, $X_4$ is threonine. Thus another preferred polypeptide includes the sequence of SEQ ID NO 29—

```
                                          SEQ ID No 29
N-(Phe/Trp/Tyr)-(Ile/Leu/Val/Ala/Met)-(Leu/Val/
Ala/Met)-Thr-(Ile/Val/Ala/Met)-C
```

In another preferred embodiment of the first aspect of the present invention, $X_5$ is isoleucine. Thus another preferred polypeptide includes the sequence of SEQ ID NO 6—

```
                                           SEQ ID No 6
N-(Phe/Trp/Tyr)-(Ile/Leu/Val/Ala/Met)-(Leu/Val/
Ala/Met)-(Ser/Thr)-Ile-C
```

More preferably at least 2, even more preferably at least 3, yet more preferably at least 4 of $X_1$, $X_2$, $X_3$, $X_4$ and $X_5$ are as defined in the preferred embodiments above.

The motif may be inserted into the leader sequence (i.e. as an addition), or can be included as a substitute for 1, 2, 3, 4, 5 or more contiguous amino acids within the leader sequence.

In one preferred embodiment, the motif is included in the leader, sequence as a substitution for naturally occurring amino acids. In other words, the amino acids of the motif are included in the place of five contiguous amino acids that were, or would have been, present in the leader sequence prior to its optimisation according to the present invention. The reader will appreciate that the phrase "naturally occurring" when used in this context, is not intended to limit the invention to the optimisation of naturally occurring leader sequences. On the contrary, this invention is also applicable to the optimisation of artificial leader sequences, such as the HSA/MFα-1 leader sequence fusion the optimisation of which is exemplified herein.

It is preferable that, where the motif is included in the leader sequence as a substitution then $X_4$ is the naturally occurring amino acid, or a variant thereof. In other words, preferably only $X_1$, $X_2$, $X_3$ and $X_5$ are substituted, whilst $X_4$ is maintained unchanged, or simply changed to a variant, preferably as a conservative substitution as defined below, of the natural amino acid at that position.

In a particularly preferred embodiment of the first aspect of the present invention, $X_1$ is phenylalanine, $X_2$ is isoleucine, $X_3$ is valine, $X_4$ is serine and $X_5$ is isoleucine. Thus in a particularly preferred embodiment of the first aspect of the invention, there is provided a polypeptide which includes the sequence of SEQ ID No 7—

```
      N-Phe-Ile-Val-Ser-Ile-C           SEQ ID No 7
```

In the above schemes, "N" and "C" denote the orientation of the polypeptide sequence, and are not intended to be limited in their interpretation to the actual termini; in other words, the polypeptide sequence may be joined (e.g. fused, conjugated or ligated), to one or more other polypeptide sequences at either the N-, or C- ends, or most usually at both ends.

A polypeptide according to the first aspect of the invention comprises the sequence of a mature desired protein, heterologous to the leader sequence. A mature desired protein sequence is the primary amino acid sequence that will be present in the expression product following post-translational processing by the expression system in which the polypeptide of the invention is expressed. The desired protein is preferably suitable for secretion from a cell in which the polypeptide of the invention is expressed.

The desired protein is heterologous to the leader sequence. In other words, the polypeptide of the first aspect of the present invention does not include naturally occurring proteins that have, in their leader sequences, the motif -$X_1$-$X_2$-$X_3$-$X_4$-$X_5$- as defined above. In a preferred embodiment, the polypeptide of the first aspect of the present invention does not include any naturally occurring protein that has the motif -$X_1$-$X_2$-$X_3$-$X_4$-$X_5$- as defined above at any position. In this context, the term "naturally occurring" refers to proteins encoded by naturally occurring organisms that have not been modified by recombinant technology, site-directed mutagenesis or equivalent artificial techniques that requires human intervention.

The desired protein may comprise any sequence, be it natural protein (including a zymogen), polypeptide or peptide, or a variant, or a fragment (which may, for example, be a domain) of a natural protein, polypeptide or peptide; or a totally synthetic protein, polypeptide or peptide; or a single or multiple fusion of different proteins, polypeptides or peptides (natural or synthetic). Such proteins can be taken, but not exclusively, from the lists provided in WO 01/79258, WO 01/79271, WO 01/79442, WO 01/79443, WO 01/79444 and WO 01/79480, or a variant or fragment thereof; the disclosures of which are incorporated herein by reference. Although these patent applications present the list of proteins in the context of fusion partners for albumin, the present invention is not so limited and, for the purposes of the present invention, any of the proteins listed therein may be presented alone or as fusion partners for albumin, the Fc region of immunoglobulin, transferrin or any other protein as a desired polypeptide.

Preferred examples of a desired protein for expression by the present invention includes albumin, transferrin, lactoferrin, endostatin, angiostatin, collagens, immunoglobulins, Fab' fragments, F(ab')2, ScAb, ScFv, interferons, IL10, IL11, IL2, interferon α species and sub-species, interferon β species and sub-species, interferon γ species and sub-species, IL1-receptor antagonist, EPO, TPO, prosaptide, cyanovirin-N, 5-helix, T20 peptide, T1249 peptide, HIV gp41, HIV gp120, fibrinogen, urokinase, prourolinase, tPA (tissue plasminogen activator), hirudin, platelet derived growth factor, parathyroid hormone, proinsulin, insulin, insulin-like growth factor, calcitonin, growth hormone, transforming growth factor β, tumour necrosis factor, G-CSF, GM-CSF, M-CSF, coagulation factors in both pre and active forms, including but not limited to plasminogen, fibrinogen, thrombin, pre-thrombin, pro-thrombin, von Willebrand's factor, $α_1$-antitrypsin, plasminogen activators, Factor VII, Factor VIII, Factor IX, Factor X and Factor XIII, nerve growth factor, LACI (lipoprotein associated coagulation inhibitor, also known as tissue factor pathway inhibitor or extrinsic pathway inhibitor), platelet-derived endothelial cell growth factor (PD-ECGF), glucose oxidase, serum cholinesterase, aprotinin, amyloid precursor, inter-alpha trypsin inhibitor, antithrombin III, apolipoprotein species, Protein C, Protein S, a variant or fragment of any of the above.

A "variant", in the context of a desired protein, refers to a protein wherein at one or more positions there have been amino acid insertions, deletions, or substitutions, either conservative or non-conservative, provided that such changes result in a protein whose basic properties, for example enzymatic activity or receptor binding (type of and specific activity), thermostability, activity in a certain pH-range (pH-stability) have not significantly been changed. "Significantly" in this context means that one skilled in the art would say that the properties of the variant may still be different but would not be unobvious over the ones of the original protein.

By "conservative substitutions" is intended combinations such as Val, Ile, Leu, Ala, Met; Asp, Glu; Asn, Gln; Ser, Thr, Gly, Ala; Lys, Arg, His; and Phe, Tyr, Trp. Preferred conservative substitutions include Gly, Ala; Val, Ile, Leu; Asp, Glu; Asn, Gln; Ser, Thr, Lys, Arg; and Phe, Tyr.

A "variant" typically has at least 25%, at least 50%, at least 60% or at least 70%, preferably at least 80%, more preferably at least 90%, even more, preferably at least 95%, yet more preferably at least 99%, most preferably at least 99.5% sequence identity to the polypeptide from which it is derived.

The percent sequence identity between two polypeptides may be determined using suitable computer programs, for example the GAP program of the University of Wisconsin Genetic Computing Group and it will be appreciated that percent identity is calculated in relation to polypeptides whose sequence has been aligned optimally.

The alignment may alternatively be carried out using the Clustal W program (Thompson et al., (1994) *Nucleic Acids Res.*, 22(22), 4673-80). The parameters used may be as follows:

Fast pairwise alignment parameters: K-tuple (word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Such variants may be natural or made using the methods of protein engineering and site-directed mutagenesis as are well known in the art.

A "fragment", in the context of a desired proteins, refers to a protein wherein at one or more positions there have been deletions. Thus the fragment may comprise at most 5, 10, 20, 30, 40 or 50% of the complete sequence of the full mature polypeptide. Typically a fragment comprises up to 60%, more typically up to 70%, preferably up to 80%, more preferably up to 90%, even more preferably up to 95%, yet more preferably up to 99% of the complete sequence of the full desired protein. Particularly preferred fragments of a desired protein comprise one or more whole domains of the desired protein. For example, the desired protein may be albumin. Albumin has three domains. A particularly preferred fragment of albumin may contain one or two domains and will thus typically comprise at least 33% or at least 66% of the complete sequence of albumin.

Albumin and transferrin, or variants or fragments thereof, are particularly preferred as a desired protein, especially when they are of human origin, i.e. they have same sequence as that found in the naturally produced human protein.

The term "human albumin" is used herein to denote material which is indistinguishable from human serum albumin or which is a variant or fragment thereof. By "variant" we include insertions, deletions and substitutions, either conservative or non-conservative, where such changes do not substantially alter the oncotic, useful ligand-binding or immunogenic properties of albumin. For example we include naturally-occurring polymorphic variants of human albumin or human albumin analogues disclosed in EP-A-322 094. Generally, variants or fragments of human albumin will have at least 10% (preferably at least 50%, 80%, 90% or 95%) of human serum albumin's ligand binding activity (for example bilirubin-binding) and at least 50% (preferably at least 80%, 90% or 95%) of human serum albumin's oncotic activity, weight for weight. Oncotic activity, also known as colloid osmotic pressure, of albumin, albumin variants or fragments of albumin may be determined by the method described by Hoefs, J. C. (1992) *Hepatology* 16:396-403. Bilirubin binding may be measured by fluorescence enhancement at 527 nm relative to HSA. Bilirubin (1.0 mg) is dissolved in 50 μL of 1M NaOH and diluted to 1.0 mL with demineralised water. The bilirubin stock is diluted in 100 mM Tris-HCl pH8.5, 1 mM EDTA to give 0.6 nmol of bilirubin mL$^{-1}$ in a fluorometer cuvette. Fluorescence is measured by excitation at 448 nm and emission at 527 nm (10 nm slit widths) during titration with HSA over a range of HSA:bilirubin ratios from 0 to 5 mol:mol.

In a preferred embodiment, the desired protein may be transferrin. This includes members of the transferrin family (Testa, *Proteins of iron metabolism*, CRC Press, 2002; Harris & Aisen, *Iron carriers and iron proteins*, Vol. 5, Physical Bioinorganic Chemistry, VCH, 1991) and their derivatives, such as transferrin, mutant transferrins (Mason et al, 1993, *Biochemistry*, 32, 5472; Mason et al, 1998, *Biochem. J.*, 330 (1), 35), truncated transferrins, transferrin lobes (Mason et al, 1996, *Protein Expr. Purif.*, 8, 119; Mason et al, 1991, *Protein Expr. Purif*, 2, 214), lactoferrin, mutant lactoferrins, truncated lactoferrins, lactoferrin lobes or fusions of any of the above to other peptides, polypeptides or proteins (Shin et al, 1995, *Proc. Natl. Acad. Sci. USA*, 92, 2820; Ali et al, 1999, *J. Biol. Chem.*, 274, 24066; Mason et al, 2002, *Biochemistry*, 41, 9448). The transferrin may be human transferrin.

The term "human transferrin" is used herein to denote material which is indistinguishable from transferrin derived from a human or which is a variant or fragment thereof. A "variant" includes insertions, deletions and substitutions, either conservative or non-conservative, where such changes do not substantially alter the useful ligand-binding or immunogenic properties of transferrin. For example we include naturally-occurring polymorphic variants of human transferrin or human transferrin analogues. Generally, variants or fragments of human transferrin will have at least 50% (preferably at least 80%, 90% or 95%) of human transferrin's ligand binding activity (for example iron-binding), weight for weight. The iron binding activity of transferrin or a test sample can be determined spectrophotometrically by 470 nm:280 nm absorbance ratios for the proteins in their iron-free and fully iron-loaded states. Reagents should be iron-free unless stated otherwise. Iron can be removed from transferrin or the test sample by dialysis against 0.1M citrate, 0.1M acetate, 10 mM EDTA pH4.5. Protein should be at approximately 20 mg/mL in 100 mM HEPES, 10 mM NaHCO$_3$ pH8.0. Measure the 470 nm:280 nm absorbance ratio of apo-transferrin (Calbiochem, CN Biosciences, Nottingham, UK) diluted in water so that absorbance at 280 nm can be accurately determined spectrophotometrically (0% iron binding). Prepare 20 mM iron-nitrilotriacetate (FeNTA) solution by dissolving 191 mg nitrotriacetic acid in 2 mL 1M NaOH, then add 2 mL 0.5M ferric chloride. Dilute to 50 mL with deionised water. Fully load apo-transferrin with iron (100% iron binding) by adding a sufficient excess of freshly prepared 20 mM FeNTA, then dialyse the holo-transferrin preparation completely against 100 mM HEPES, mM NaHCO$_3$ pH8.0 to remove remaining FeNTA before measuring the absorbance ratio at 470 nm:280 nm. Repeat the procedure using test sample, which should initially be free from iron, and compare final ratios to the control.

Additionally, single or multiple heterologous fusions of any of the above; or single or multiple heterologous fusions to albumin, transferrin or immunoglobins or a variant or fragment of any of these may be used. Such fusions include albumin N-terminal fusions, albumin C-terminal fusions and co-N-terminal and C-terminal albumin fusions as exemplified by WO 01/79271, and transferrin N-terminal fusions, transferrin C-terminal fusions, and co-N-terminal and C-terminal transferrin fusions.

In a preferred embodiment, a polypeptide according to a first aspect of the invention comprises a secretion pre sequence that includes at least a part of the $X_1$-$X_5$ pentapeptide motif as defined above. In other words, the region of the leader sequence that acts to effect secretion of the mature desired polypeptide contains, 1, 2, 3, 4, or 5 of the amino acids of the $X_1$-$X_5$ pentapeptide motif. Where the secretion pre sequence region contains less than 5 amino acids of the $X_1$-$X_5$ pentapeptide motif, those amino acids of the motif that are contained in the pre sequence are located at one of the borders of the pre sequence region, such that they are adjacent to the remaining amino acids of the $X_1$-$X_5$ pentapeptide motif.

In a more preferred embodiment a polypeptide according to a first aspect of the present invention comprises a leader sequence characterised in that it includes a secretion pre sequence that includes the motif as defined above by the first aspect of the present invention. The leader sequence is usually, although not necessarily, located at the N-terminus of the primary translation product and is generally, although not necessarily, cleaved off the protein during the secretion process, to yield the mature "desired" protein.

A secretion leader sequence is usually, although not necessarily, an N-terminal sequence of amino acids that causes the polypeptide of which it forms part to be secreted from a host cell in which it is produced. Secretion is defined by the co-translational of post-translation translocation of a protein from the cytoplasmic compartment across a phospholipid bilayer, typically, but not exclusively the endoplasmic reticulum of eukaryotic organisms or the plasma membrane of prokaryotic organisms. The secreted protein may be retained within the confines of the cell (typically, but not exclusively, within the endoplasmic reticulum, Golgi apparatus, vacuole, lysosome or periplasmic space) or it may be secreted from the cell into the culture medium. A sequence acts as a secretion leader sequence if, in comparison to an equivalent polypeptide without the secretion pre sequence, it causes more of that polypeptide to be secreted from the host cell in which it is produced. Generally speaking, a polypeptide with a leader sequence will be secreted whereas a polypeptide without a leader sequence will not. However, the present invention contemplates circumstances wherein different leader sequences will have different levels of efficiency. Thus a leader sequence may cause at least 10%, 20%, 30 or 40% or 50%, typically at least 60% or 70%, preferably at least 80%, more preferably at least 90%, even more preferably at least 95%, yet more preferably at least 98%, most preferably at least 99% of the mature protein produced by the cell to be secreted from the cell. Secretion of a mature polypeptide from a cell can be determined, for example, by providing a host cell with appropriate DNA constructs and measuring the amount of the mature protein (for example, human albumin) that is secreted, compared with any mature protein that is produced intracellularly.

A preferred secretion leader sequence will provide for the above mentioned levels of secretion when the host cell is a yeast cell (eg. *Saccharomyces cerevisiae* or *Pichia pastoris*). Secretion of a mature polypeptide from a yeast host cell can be determined, for example, by methods such as those set out in the examples below.

Accordingly, secretion can be measured by comparing the level of secretion of a protein comprising a test leader sequence to the level of secretion of a protein comprising a control leader sequence. In order to determine whether a given sequence (the "test sequence") is able to achieve a given level of secretion, a first protocol may be used in which a 'starter' plasmid, typically a yeast disintegration vector of the type described in EP 0 286 422, having the LEU2 gene and a polynucleotide encoding rHA with a modified leader sequence as defined by SEQ ID NO:26 operably linked to functional yeast regulatory regions, such as a PRB1 promoter and an ADH1 terminator as described below, is modified to include a polynucleotide sequence that encodes the test sequence in place of an equivalent region of the leader sequence, thereby to provide a test plasmid. As a first control, the unmodified 'starter' plasmid encoding the leader sequence described in WO 90/01063 is used. *Saccharomyces cerevisiae* strain AH22 cir$^0$ (Hinnen et al, 1978, *Proc. Natl. Acad. Sci. USA,* 75(4), 1929-33; Mead et al, 1986, *Mol. Gen. Genet.,* 205, 417), His4 reverted, is used as a test host. A HIS4 revertant (i.e. His+) of AH22 (leu2, his4, can1) can be obtained by culturing sufficient AH22 cells on BMMD agar, supplemented with 0.002% (w/v) leucine, until colonies appear. The colonies are tested to confirm that that are Leu– and His+ (i.e. AH22 His+ (leu2, can1)) by plating onto BMMD agar, supplemented with 0.002% (w/v) leucine (plate 1), BMMD agar, supplemented with 0.002% (w/v) leucine and, supplemented with 0.002% (w/v) histidine (plate 2), and BMMD agar (plate 3). AH22 His+ (leu2, can1) isolates will grow on plate 1 and plate 2, but will not grow on plate 3. The test host is transformed to leucine prototrophy with the test and control plasmids. Transformants are patched out onto Buffered Minimal Medium (BMM, described by Kerry-Williams, S. M. et al. (1998) Yeast 14, 161-169) containing 2% (w/v) glucose (BMMD) and incubated at 30° C. until grown sufficiently for further analysis. Transformants are cultivated in high cell density fermentation according to a fill & draw procedure, in a medium and using control parameters as described for the fed-batch procedure in WO 96/37515: upon completion of the feed phase of the fed-batch culture procedure, 90% of the culture volume is removed from the fermenter vessel Batch medium is added to the remaining 10% volume of the culture (maintaining pH control) prior to the initiation of feed addition, using the medium and control parameters described in WO 96/37515. The procedure of fill & draw can be repeated for an unlimited number of cycles. The human albumin productivity ($Y_{P/S}$) of the transformants containing test and control plasmids are assessed by scanning densitometry of SDS-PAGE of cell free whole culture. $Y_{P/S}$ represents the ratio of human albumin protein (mg) per gram of sucrose added to the culture during fermentation.

A leader sequence according to the present invention may obtain a level of secretion, as determined by $Y_{P/S}$ as measured by the above first protocol, that is at least 10%, 20%, 30%, 40%, 50%, 60%, 70%, 80%, 90%, 100%, 110%, 120%, 130%, 140%, 150%, 160%, 170%, 180%, 190%, 200%, 210%, 220%, 230%, 240%, 250%, 260%, 270%, 280%, 290%, 300%, 310%, 320%, 330%, 340%, 350%, 360%, 370%, 380%, 390%, 400%, 410%, 420%, 430%, 440%, 450%, 460%, 470%, 480%, 490% or 500% higher than the level of secretion obtained by the first control when the test and first control transformants are cultured for comparable lengths of time with comparable fermenter configurations. Thus a leader sequence according to the present invention may demonstrate a level of secretion that is up to 400%, 450%, 500%, 550%, 600%, 650%, 700%, 750%, or more higher than the first control. It is particularly preferred that a leader sequence according to the present invention can obtain a level of secretion at least 400%, such as 408%, or at least 440%, such as 442%, higher than the level of secretion obtained by the first control.

As an alternative to the first protocol, a second protocol may be used to determine whether a given sequence (the "test sequence") is able to achieve a given level of secretion. The second protocol is essentially the same as the first protocol.

However, the second protocol utilises a 'starter' plasmid as defined above with the exception that, in place of SEQ ID NO:26 the plasmid has the polynucleotide sequence defined by SEQ ID NO:22, which also encodes a leader sequence having the amino acid sequence described in WO 90/01063 linked to a polynucleotide encoding rHA (the "second starter" plasmid). A test plasmid is produced by modifying the second starter plasmid to include a polynucleotide sequence that encodes the test sequence in place of an equivalent region of the leader sequence of the second starter plasmid. As a second control, the unmodified second starter plasmid is used. Transformants comprising the test and second control plasmids are prepared as described above in the first protocol and cultivated in a high cell density fermentation according to a fed-batch procedure in a medium and using control parameters as described in WO 96/37515. $Y_{P/S}$ is assessed as described above.

A leader sequence according to the present invention may obtain a level of secretion, as determined by $Y_{P/S}$ as measured by the above second protocol, that is at least 1%, 2%, 3%, 4%, 5%, 6%, 7%, 8%, 9%, 10%, 11%, 12%, 13%, 14%, 15%, 16%, 17%, 18%, 19% or 20% higher than the level of secretion obtained by the second control when the test and second control transformants are cultured for comparable lengths of time with comparable fermenter configurations. Thus a leader sequence according to the present invention may demonstrate a level of secretion that is up to 20%, 30%, 40%, 50%, 60%, 70%, 80%, 90%, 100% or more higher than the second control. It is particularly preferred that a leader sequence according to the present invention can obtain a level of secretion at least 5%, such as 6%, or at least 10%, such as 12%, 13%, 14%, 15% or 16% higher than the level of secretion obtained by the second control.

In one embodiment, a leader sequence according to the present invention will obtain a level of secretion as defined above in respect of the first protocol. In another embodiment, a leader sequence according to the present invention will obtain a level of secretion as defined above in respect of the second protocol. In a particularly preferred embodiment, a leader sequence according to the present invention will obtain a level of secretion as defined above in respect of both the first and second protocols.

Solubilised proteins from the cell biomass and secreted proteins in the culture supernatant can be analysed by:
1. Gel permeation high pressure liquid chromatography.
2. Densitometry of SDS-PAGE
3. Rocket immunoelectrophoresis The amount of the desired protein, secreted and intracellular, can be quantified relative to a standard curve of the desired protein and normalised to the amount of biomass as known by those skilled in the art.

Usually it is preferable if the leader sequence is derived from the immature version of the mature protein to which it is, or is intended to be, attached. Thus, for example, where the mature protein is albumin, it is preferred to use sequences comprising the naturally occurring albumin secretion pre sequence, or pro sequence or pre-pro sequence. However, the leader sequence may alternatively be derived from a source other than that of the mature protein.

Thus in one preferred embodiment, the leader sequence of a polypeptide of the first aspect of the present invention comprises a secretion pre sequence derived from an albumin secretion pre sequence, or variant thereof.

A "variant" of an albumin pre sequence, as used above, refers to an albumin pre sequence wherein at one or more positions, other than at those defined by $X_1$, $X_2$, $X_3$, $X_4$ or $X_5$ above, there have been amino acid insertions, deletions, or substitutions, either conservative (as described above) or non-conservative, provided that such changes still allow the peptide to act as a pre sequence.

Preferably, a "variant" of an albumin pre sequence has, other than the residues defined as $X_1$-$X_5$ above, at least 2, at least 3 or at least 4, preferably at least 5, more preferably at least 6, even more preferably at least 7, yet more preferably at least 8, most preferably at least 9 identical amino acids to a naturally occurring albumin pre sequence, most preferably the albumin pre sequence of FIG. 1.

Even more preferably, where the secretion pre sequence is derived from an albumin secretion pre sequence, a polypeptide according to the first aspect of the present invention has $X_1$, $X_2$, $X_3$, $X_4$ and $X_5$ at positions −20, −19, −18, −17 and −16, respectively, in place of the naturally occurring amino acids at those positions, wherein the numbering is such that the −1 residue is the C-terminal amino acid of the native albumin secretion pro sequence and where $X_1$, $X_2$, $X_3$, $X_4$ and $X_5$ are amino acids as defined above For example, when the above mentioned numbering is applied to the sequence of the human albumin secretion pre sequence (as disclosed, for example in WO 90/01063), the following is obtained:

```
N -  Met Lys Trp Val Ser Phe Ile Ser Leu Leu
     -24 -23 -22 -21 -20 -19 -18 -17 -16 -15

Phe Leu Phe Ser Ser Ala Tyr Ser - C
     -14 -13 -12 -11 -10  -9  -8  -7
```

In a particularly preferred embodiment the secretion pre sequence used is derived from the sequence of the human albumin secretion pre sequence.

Thus, for example, the $X_1$-$X_5$ pentapeptide may be fused at its N-terminal end, directly or indirectly, to the C-terminal end of the following sequence SEQ ID NO 8—

```
       N-Met-Lys-Trp-Val-C                SEQ ID No 8
``` or a conservatively substituted variant thereof, namely—

```
N-Met-(Lys/Arg/His)-(Phe/Trp/Tyr)-       SEQ ID No. 33
(Ile/Leu/Val/Ala/Met)-C
```

Additionally or alternatively it may be fused at its C-terminal end, directly or indirectly, to the N-terminal end of at least one of the following sequences—

```
N-Leu-Phe-Leu-Phe-Ser-Ser-Ala-Tyr-Ser-C  SEQ ID No 9
``` or a conservatively substituted variant thereof, namely—

```
                                         SEQ ID No. 10
N-(Ile/Leu/Val/Ala/Met)-(Phe/Trp/Tyr)-(Ile/Leu/
Val/Ala/Met)-(Phe/Trp/Tyr)-(Ser/Thr/Gly/Tyr/Ala)-
(Ser/Thr/Gly/Tyr/Ala)-(Ile/Leu/Val/Ala/Met)-(Phe/
Trp/Tyr)-(Ser/Thr/Gly/Tyr/Ala)-C
``` or

```
                                         SEQ ID No 11
N-Leu-Phe-Leu-Phe-Ser-Ser-Ala-Tyr-Ser-Arg-Ser-Leu-
Asp-Lys-Arg-C
``` or

```
                                         SEQ ID No. 30
N-Leu-Phe-Leu-Phe-Ser-Ser-Ala-Tyr-Ser-Arg-Gly-Val-
Phe-Arg-Arg-C
```

The sequence given in SEQ ID No 9 represents the final nine amino acids of the natural human albumin pre sequence. In the case of SEQ ID No 11, this is fused to the final six amino acids of one of the taco principal fused leader sequences of WO 90/01063 and, in the case of SEQ ID No. 30, SEQ ID No. 9 is fused to the final six amino acids of the natural human albumin pro sequence.

Preferably, in each case, $X^1$ is F, $X^2$ is I, $X^3$ is V, $X^4$ is S or T and $X^5$ is I.

In a preferred embodiment, the pentapeptide is fused at its N-terminal to the C-terminal of sequence of SEQ ID NO 8 or a conservatively substituted variant thereof and is fused at its C-terminal to the N-terminal of the sequence of SEQ ID NO 9, a conservatively substituted variant thereof, SEQ ID No. 10, 11 or 30, thereby to form, for example, one of the following sequences—

```
                                              SEQ ID No 12
N-Met-Lys-Trp-Val-X1-X2-X3-X4-X5-Leu-Phe-Leu-Phe-
Ser-Ser-Ala-Tyr-Ser-C
``` or

```
                                              SEQ ID No 13
N-Met-Lys-Trp-Val-X1-X2-X3-X4-X5-(Ile/Leu/Val/Ala/
Met)-(Phe/Trp/Tyr)-(Ile/Leu/Val/Ala/Met)-(Phe/
Trp/Tyr)-(Ser/Thr/Gly/Tyr/Ala)-(Ser/Thr/Gly/Tyr/
Ala)-(Ile/Leu/Val/Ala/Met)-(Phe/Trp/Tyr)-(Ser/
Thr/Gly/Tyr/Ala)-C
``` or

```
                                              SEQ ID No 14
N-Met-Lys-Trp-Val-X1-X2-X3-X4-X5-Leu-Phe-Leu-Phe-
Ser-Ser-Ala-Tyr-Ser-Arg-Ser-Leu-Asp-Lys-Arg-C

SEQ ID No 31
N-Met-Lys-Trp-Val-X1-X2-X3-X4-X5-Leu-Phe-Leu-Phe-
Ser-Ser-Ala-Tyr-Ser-Arg-Gly-Val-Phe-Arg-Arg-C
``` wherein $X_1$-$X_5$ are as defined above, or a conservatively substituted variant thereof, as defined above.

An especially preferred embodiment has, as the secretion pre sequence, the sequence of SEQ ID NO 28—

```
                                              SEQ ID No 28
N-Met-Lys-Trp-Val-Phe-Ile-Val-Ser-Ile-Leu-Phe-Leu-
Phe-Ser-Ser-Ala-Tyr-Ser-C
``` i.e. the pre sequence is derived from the human serum albumin secretion pre sequence, $X_1$, $X_2$, $X_3$, $X_4$ and $X_5$ are at positions −20, −19, −18, −17 and −16, and $X_1$, $X_2$, $X_3$, $X_4$ and $X_5$ are as defined by SEQ ID No.7.

As is apparent from above, a secretion pre sequence as defined above, such as the sequences of SEQ ID Nos 12 or 28, may be combined with secretion pro sequences to form functional pre-pro secretion sequences. In a preferred embodiment, a pre sequence motif is fused by a peptide bond at its C-terminal end to the N-terminal amino acid of a secretion pro sequence motif, thereby to form a pre-pro sequence motif. It may be preferable to use a pro sequence derived from the immature version of the mature protein to which the leader sequence is, or is intended to be, attached. It may also be preferable to use the pro sequence that is associated in nature with the unmodified pre sequence or a pro sequence, or part thereof, from an related leader.

Preferably, the pro sequence terminates at its C-terminus in a dibasic pair of amino acids, i.e. each is Lys or Arg.

Typically the secretion pro sequence motif is an albumin secretion pro sequence or variant thereof, such a variant including the dibasic pair of amino acids and having only conservative substitutions at the other positions, usually a human albumin secretion pro sequence, i.e. having the sequence N-Arg-Gly-Val-Phe-Arg-Arg-C or variant thereof. In another preferred embodiment the pro sequence comprises the sequence of the whole or part of the yeast MFα-1 secretion pro sequence, i.e. N-Ser-Leu-Asp-Lys-Arg-C or variant thereof as defined for the albumin pro sequence.

In comparison with the corresponding parts of the leader defined in WO 90/01063 and the human albumin leader, a polypeptide of the present invention has at least four amino acid changes namely Ser-20Phe or Trp or Tyr; Phe-19Ile or Leu or Val or Ala or Met; Ile-18Leu or Val or Ala or Met; and Leu-16Ile or Val or Ala or Met, where the notation means that, taking the first-named mutation as an example, the serine residue at position −20 (i.e. minus twenty relative to the N-terminus of the mature protein that is to be secreted using the leader sequence) is changed to a phenylalanine residue. This is exemplified in FIG. 1.

One preferred pre-pro sequence comprises the sequence:

MKWVFIVSILFLFSSAYSRY$^1$Y$^2$Y$^3$Y$^4$Y$^5$ wherein $Y^1$ is Gly or Ser, $Y^2$ is Val or Leu, $Y^3$ is Phe or Asp, $Y^4$ is Arg or Lys and $Y^5$ is Arg or Lys.

In a preferred embodiment, $Y^1$ is Gly, $Y^2$ is Val and $Y^3$ is Phe. In another preferred embodiment $Y^1$ is Ser, $Y^2$ is Leu and $Y^3$ is Asp.

Typically $Y^4$ is Arg and $Y^5$ is Arg. Alternatively it is preferred if $Y^4$ is Lys and $Y^5$ is Arg. Another preferred alternative is where $Y^4$ is Lys and $Y^5$ is Lys. $Y^4$ may also be Arg where $Y^5$ is Lys.

An especially preferred embodiment has, as the secretion prepro sequence, the sequence of SEQ ID NO 32

```
                                              SEQ ID No 32
N-Met-Lys-Trp-Val-Phe-Ile-Val-Ser-Ile-Leu-Phe-Leu-
Phe-Ser-Ser-Ala-Tyr-Ser-Arg-Ser-Leu-Asp-Lys-Arg-C
```

A second aspect of the invention provides an isolated polynucleotide having a sequence that encodes the motif as defined by the first aspect of the invention.

As used herein, the term "isolated" includes the meaning that the polynucleotide, where it is a DNA molecule, is in isolation from at least most of the chromosome on which it is naturally found and, where it is an RNA molecule, is in isolation from an intact cell in which it is naturally transcribed. In other words, the polynucleotide is not claimed in a form in which it has previously existed, such as in nature. Thus, a polynucleotide according to the second aspect of the invention includes a polynucleotide that has been cloned into a bacterial or fungal vector, such as a plasmid, or into a viral vector, such as a bacteriophage. Preferably such clones are in isolation from clones constituting a DNA library of the relevant chromosome.

The linear amino acid sequence can be reverse translated into a DNA sequence using the degenerate standard genetic code (FIG. 2) in which most amino acids are encoded by more than one trinucleotide codon.

For example, a DNA sequence encoding the peptide defined as SEQ ID 1 would be deduced to be:

```
                                              SEQ ID No 15
5'-(TTY/TGG/TAY)-(ATH/TTR or CTN/GTN/GCN/ATG)-(TTR
or CTN/GTN/GCN/ATG)-(AGY or TCN/ACN)-(ATH or
CTN/GTN/GCN/ATG)-3'
``` where "3'" and "5'" denote the orientation of the polynucleotide sequence, rather than the actual termini; in other words, the polynucleotide sequence may be joined (e.g. fused or ligated) to other polynucleotide sequences at either end or both ends, and wherein Y, R, H and N are as defined in FIG. 2.

Using the same conversion procedure the DNA sequence:

```
5'-TTY-ATH-GTN-(TCN or AGY)-ATH-3'    SEQ ID No 16
``` would be deduced to encode the polypeptide of SEQ ID No 7.

In the case of a polynucleotide sequence comprising a sequence that encodes a naturally occurring mature protein, such a human albumin, this can be either the naturally occurring coding sequence, such as the human albumin gene sequence, or a complementary DNA sequence (cDNA) or a cDNA containing one or more introns.

Further sequence modifications may also be introduced, for example into the coding region. A desirable way to modify the DNA encoding the polypeptide of the invention is to use the polymerase chain reaction as disclosed by Saiki et al (1988) *Science* 239, 487-491. In this method the DNA to be enzymatically amplified is flanked by two specific oligonucleotide primers which themselves become incorporated into the amplified DNA. The said specific primers may contain restriction endonuclease recognition sites which can be used for cloning into expression vectors using methods known in the art.

The polynucleotide encoding a leader sequence of the invention is most conveniently made by chemical synthesis of an oligonucleotide, followed by ligation to the other elements of the genetic construct, by methods that are well known in this art and described in more detail below.

Where it is desirable to modify the polynucleotide that encodes mature albumin, this may be most conveniently achieved by site-directed mutagenesis or PCR mutagenesis, starting from the natural cDNA sequence, or from assembling synthetic oligonucleotides. Again, such techniques are standard in this art and are in any case set out in more detail below.

Modification to the coding sequence can be advantageous because, within a particular organism, the polynucleotide sequences encoding some highly expressed proteins favour some codons over others for a particular amino acid; this is called codon bias. In a preferred embodiment of a second aspect of the invention the standard genetic code can be reduced to the preferred codons for the host organism of choice. In an especially preferred embodiment of the second aspect of the invention the standard genetic code can be reduced to the preferred codons of yeast. (See Table 4 of Sharp and Crowe (1991) Yeast 7, 657-678.) Advantageously this list of preferred yeast codons is modified by inclusion of the asparagine codon 5'-GAT-3' (FIG. 3).

Using the peptide sequence of SEQ ID No 1 as an example, the codon biased DNA sequence encoding this peptide in yeast may be deduced to be:

```
                                              SEQ ID No 17
5'-(TTC/TGG/TAC)-(ATY/TTG/GTY/GCT/ATG)-(TTG/GTY/
GCT/ATG)-(TCY/ACY)-(ATY/GTY/GCT/ATG)-5'
```

Using the same conversion procedure the codon-biased degenerate DNA sequence:

```
5'-TTC-ATY-GTY-TCY-ATY-3'    SEQ ID No 18
``` would be deduced for the especially preferred polypeptide motif having the sequence of SEQ ID No 7, although the most preferred codon-biased DNA sequence encoding a polypeptide motif having the sequence of SEQ ID No 7 is—

```
TTCATCGTCTCCATT    SEQ ID No. 34
```

Using the genetic code given in FIG. 2 or the preferred codon bias tables available for the intended host or the preferred codon bias given in FIG. 3, the same conversion procedure can be used to convert any desired amino acid sequence into a partially redundant polynucleotide sequence. The amino acid sequences, which can be converted into a DNA sequence by this method can be taken from, but not limited to, polypeptides according to the first aspect of the invention. For example, the sequence of a coding region for mature human albumin can be derived in this way. EP 308 381 discloses a partially yeast-codon-optimised coding sequence for human albumin. SEQ ID No. 20 herein is further such sequence. Advantageously, where the DNA sequence redundancy permits, restriction sites can be introduced at domain and sub-domain boundaries, without perturbing the encoded amino acid sequence (or the codon bias if FIG. 3 is used).

The remaining DNA sequence redundancies can be resolved and the number of occurrences of alternative codons equalised for each amino acid with redundant DNA sequences. Advantageously, DNA sequences representing possible transcription terminator sequences can be removed or reduced where possible by utilising the DNA sequence redundancy of the degenerate codons. Finally the balance of alternative codons for amino acids with redundant DNA sequences can be re-equalised but without conflicting with the previous modifications A polynucleotide according to the second aspect of the invention can be directly or indirectly fused to one or more other nucleotide sequences at its 5' and/or 3' ends, for example to form a complete gene or expression cassette. Thus, the expression cassette will desirably also contain sites for transcription initiation and termination, and in the transcribed region, a ribosome binding site for translation initiation. (Hastings et al, WO 98/16643, published 23 Apr. 1998.)

Accordingly, the second aspect of the present invention includes a polynucleotide comprising a DNA sequence that is a contiguous or non-contiguous fusion of a DNA encoding a heterologous protein with either a DNA sequence encoding a polypeptide according to the first aspect of the present invention, particularly wherein the desired-protein is albumin, or a variant or fragment thereof. In this context, the term "heterologous protein" means that it is not the same as the "desired protein", i.e. does not form a homodimer.

Accordingly, the polynucleotide may be directly or indirectly fused to a promoter (an expression control element formed by a DNA sequence that permits binding of RNA polymerase and transcription to occur) at its 5' end and/or to other regulatory sequences, such as, at its 3' end, translation termination sequences. Thus a polynucleotide may be operably linked to one or more regulatory regions, usually transcription regulatory regions. By "operably linked" is meant that the regulatory region is linked in such a way that it is able to exert an effect on the polynucleotide sequence. The choice of which regulatory region to use will be partially dependant upon the expected host (i.e. the intended expression system) and the selection, of the preferred sequence will be known to those skilled in the art Many expression systems are known, including systems employing: bacteria (eg. *Bacillus subtilis* or *Escherichia coli*) transformed with, for example, recombinant bacteriophage, plasmid or cosmid DNA expression vectors; yeasts (eg. *Saccharomyces cerevisiae* or *Pichia pastoris*) transformed with, for example, yeast expression vectors; insect cell systems transformed with, for example, viral expression vectors (eg.

baculovirus); plant cell systems transfected with, for example viral or bacterial expression vectors; animal cell systems, either in cell culture, transgenic or as gene therapy, transfected with, for example, adenovirus expression vectors. The host cell is preferably a yeast (and most preferably a *Saccharomyces* species such as *S. cerevisiae* or a *Pichia* species such as *P. pastoris*).

Accordingly, a third aspect of the present invention provides a host cell transformed with a polynucleotide according to the second aspect of the present invention. The host cell can be either prokaryotic or eukaryotic. Bacterial cells are preferred prokaryotic host cells, particularly if they can secrete proteins, as can some species of *Bacillus* and *Escherichia*. Preferred is eukaryotic host cells include plants, fungi, yeast and animal cells, preferably vertebrate cells, more preferably mammalian cells, such as those from a mouse, rat, cow, sheep, goat, pig, buffalo, yak, horse or other domesticated animal, monkey or human. Suitable human cells include cells from a human fibroblastic cell line. Thus a host cell may be a transgenic cell of a mammal in situ, and may thus be the result of a gene therapy approach or of the production of a transgenic individual. In the latter case it is preferred that the individual is a non-human mammal.

Exemplary genera of bacterial hosts include *E. coli* and *Bacillus subtilis*.

Exemplary genera of plant hosts include spermatophytes, pteridophytes (e.g. ferns, clubmosses, horsetails), bryophytes (e.g. liverworts and mosses), and algae. Typically the plant host cell will be derived from a multicellular plant, usually a spermatophyte, such as a gymnosperm or an angiosperm. Suitable gymnosperms include conifers (e.g. pines, larches, firs, spruces and cedars), cycads, yews and ginkos. More typically the plant host cell is the cell of an angiosperm, which may be a monocotyledonous or dicotyledonous plant, preferably a crop plant. Preferred monocotyledonous plants include maize, wheat, barley, sorghum, onion, oats, orchard grass and other *Pooideae*. Preferred dicotyledonous crop plants include tomato, potato, sugarbeet, cassaya, cruciferous crops (including oilseeds rape), linseed, tobacco, sunflower, fibre crops such as cotton, and leguminous plants such as peas, beans, especially soybean, and alfalfa. The host cell may thus be an autonomous cell, for example the cell of a unicellular plant or a cell maintained in cell culture, or it may be a cell in situ in a multicellular plant. Accordingly the present invention contemplates the production of whole transgenic plants, which preferably retain a stable and heritable transgenic phenotype.

Exemplary genera of fungal hosts include *Aspergillus* (e.g. *A. niger* and *A. oryzae*), *Streptomyces*, *Penicillium* and yeasts. Exemplary genera of yeast contemplated to be useful in the practice of the present invention are *Pichia* (*Hansenula*), *Saccharomyces*, *Kluyveromyces*, *Candida*, *Torulopsis*, *Torulaspora*, *Schizosaccharomyces*, *Citeromyces*, *Pachysolen*, *Debaromyces*, *Metschunikowia*, *Rhodosporidium*, *Leucosporidium*, *Botryoascus*, *Sporidiobolus*, *Endomycopsis*, and the like. Preferred genera are those selected from the group consisting of *Pichia* (*Hansenula*), *Saccharomyces*, *Kluyveromyces* and *Yarrowia*. Examples of *Saccharomyces* spp. are *S. cerevisiae*, *S. italicus* and *S. rouxii*. Examples of *Kluyveromyces* spp. are *K. fragilis* and *K. lactis*. Examples of *Pichia* (*Hansenula*) are *P. pastoris*, *P. anomala* and *P. capsulata*. *Y. ipolytica* is an example of a suitable *Yarrowia* species. Yeast host cells include YPH499, YPH500 and YPH501 which are generally available from Stratagene Cloning Systems, La Jolla, Calif. 92037, USA.

Preferred mammalian host cells include Chinese hamster ovary (CHO) cells available from the ATCC as CCL61, NIH Swiss mouse embryo cells NIH/3T3 available from the ATCC as CRL 1658, and monkey kidney-derived COS-1 cells available from the ATCC as CRL 1650. Preferred insect cells are Sf9 cells which can be transfected with baculovirus expression vectors.

As discussed above, the choice of polynucleotide regulatory region will be partly dependent on the nature of the intended host.

Promoters suitable for use in bacterial host cells include the *E. coli* lacI and lacZ promoters, the T3 and T7 promoters, the gpt promoter, the phage λ PR and PL promoters, the phoA promoter and the tip promoter. Promoter sequences compatible with exemplary bacterial hosts are typically provided in plasmid vectors containing convenient restriction sites for insertion of a DNA segment of the present invention.

Eukaryotic promoters include the CMV immediate early promoter, the HSV thymidine kinase promoter, the early and late SV40 promoters and the promoters of retroviral LTRs. Other suitable promoters will be known to those skilled in the art.

Suitable promoters for *S. cerevisiae* include those associated with the PGK1 gene, GAL1 or GAL10 genes, CYC1, PHO5, TRP1, ADH1, ADH2, the genes for glyceraldehyde-3-phosphate dehydrogenase, hexokinase, pyruvate decarboxylase, phosphofructokinase, triose phosphate isomerase, phosphoglucose isomerase, glucokinase, α-mating factor pheromone, α-mating factor pheromone, the PRB1 promoter, the GPD1 promoter, and hybrid promoters involving hybrids of parts of 5' regulatory regions with parts of 5' regulatory regions of other promoters or with upstream activation sites (e.g. the promoter of EP-A-258 067).

Convenient regulatable promoters for use in *Schizosaccharomyces pombe*, another suitable host cell, are the thiamine-repressible promoter from the nmt gene as described by Maundrell (1990) *J. Biol. Chem.* 265, 10857-10864 and the glucose-repressible fbp1 gene promoter as described by Hoffman & Winston (1990) *Genetics* 124, 807-816.

Suitable promoters, transformation protocols and culture conditions for *Pichia* can be found in U.S. Pat. No. 5,986,062 (incorporated herein by reference). For example, preparation of an HSA-producing host (or an HSA-producing strain) may be effected using a process in which a recombinant plasmid is introduced into chromosome (JP-A-3-72889 corresponding to EP-A-399455), a process in which HSA is expressed in yeast (JP-A-60-41487 corresponding to EP-A-123544, JP-A-63-39576 corresponding to EP-A-248657 and JP-A-63-74493 corresponding to EP-A-251744) and a process in which HSA is expressed in *Pichia* (JP-A-2-104290 corresponding to EP-A-344459). Culturing of an HSA-producing host (an HSA production process) may be carried out using known processes, such as those referred to in U.S. Pat. No. 5,986,062, for example in accordance with a process disclosed in JP-A-3-83595 or JP-A-4-293495 (corresponding to EP-A-504823). The medium for culturing a transformed host may be prepared in accordance with U.S. Pat. No. 5,986,062 and culturing of a host may be carried out preferably at 15 to 43° C. (more preferably 20 to 30° C.) for 1 to 1,000 hours, by means of static or shaking culturing or batch, semi-batch or continuous culturing under agitation and aeration in accordance with the disclosures of U.S. Pat. No. 5,986,062.

Suitable transcription termination signals are well known in the art. Where the host cell is eukaryotic, the transcription termination signal is preferably derived from the 3' flanking sequence of a eukaryotic gene, which contains proper signals for transcription termination and polyadenylation. Suitable 3' flanking sequences may, for example, be those of the gene naturally linked to the expression control sequence used, i.e. may correspond to the promoter. Alternatively, they may be different. In that case, and where the host is a yeast, preferably *S. cerevisiae*, then the termination signal of the *S. cerevisiae* ADH1 gene is preferred.

Thus a polynucleotide according to the second aspect of the present invention can be developed for any desired host by using methods such as those described above.

A DNA sequence encoding mature human albumin can be developed from DNA fusions between the native gene, cDNA or a cDNA containing one or more introns, as described above and a codon biased human albumin DNA is sequence derived by the method described above.

SEQ IQ No 19 is a polynucleotide sequence that comprises 22 nucleotides 5' to the translation initiation site, a preferred polynucleotide coding sequence for the secretion leader sequence SEQ ID No. 32 and a mature human albumin coding region SEQ ID No 20. The coding sequence ends with a translation stop codon. Typically, this is TGA, TAG or TAA, although TAA is the most efficient in yeast. Preferably, further translation stop codons (preferably each is TAA), usually one or two, are included, preferably adjacent each other or with no more than 3 base pairs between each pair of stop codons. SEQ IQ No 19 is flanked at both ends by appropriate cloning sites.

The polynucleotide of the second aspect of the invention may also be joined to a wide variety of other DNA sequences for introduction into an appropriate host. The companion sequence(s) will depend upon the nature of the host, the manner of the introduction of the polynucleotide into the host, and whether episomal maintenance or integration is desired. For example, the vectors can include a prokaryotic replicon, such as the Col E1 ori for propagation in a prokaryote, even if the vector is to be used for expression in other, non-prokaryotic cell types.

Generally, a polynucleotide according to the second aspect of the invention is inserted into an expression vector, such as a plasmid, in proper orientation and correct reading frame for expression.

Thus, the polynucleotide may be used in accordance with known techniques, appropriately modified in view of the teachings contained herein, to construct an expression vector, including, but not limited to integration vectors, centromeric vectors and episomal vectors.

Thus in one embodiment of the second aspect of the invention, the polynucleotide is a vector.

Typical prokaryotic vector plasmids are: pUC18, pUC19, pBR322 and pBR329 available from Biorad Laboratories (Richmond, Calif., USA); pTrc99A, pKK223-3, pKK233-3, pDR540 and pRIT5 available from Pharmacia (Piscataway, N.J., USA); pBS vectors, Phagescript vectors, Bluescript vectors, pNH8A, pNH16A, pNH18A, pNH46A available from Stratagene Cloning Systems (La Jolla, Calif. 92037, USA).

A typical mammalian cell vector plasmid is pSVL available from Pharmacia (Piscataway, N.J., USA). This vector uses the SV40 late promoter to drive expression of cloned genes, the highest level of expression being found in T antigen-producing cells, such as COS-1 cells. An example of an inducible mammalian expression vector is pMSG, also available from Pharmacia (Piscataway, N.J., USA). This vector uses the glucocorticoid-inducible promoter of the mouse mammary tumour virus long terminal repeat to drive expression of the cloned gene.

Useful yeast episomal plasmid vectors are pRS403-406 and pRS413-416 and are generally available from Stratagene Cloning Systems (La Jolla, Calif. 92037, USA), YEp24 (Botstein, D., et al. (1979) Gene 8, 17-24), and YEplac122, YEplac195 and YEplac181 (Gietz, R. D. and Sugino. A. (1988) Gene 74, 527-534). Other yeast plasmids are described in WO 90/01063 and EP 424 117, as well as the "disintegration vectors of EP-A-286 424. Plasmids pRS403, pRS404, pRS405 and pRS406 are Yeast Integrating plasmids (YIps) and incorporate the yeast selectable markers HIS3, TRP1, LEU2 and URA3, as are YIplac204, YIplac211 and YIplac128 (Gietz, R. D. and Sugino. A. (1988) Gene 74, 527-534). Plasmids pRS413-416 are Yeast Centromere plasmids (YCps) as are YCplac22, YCplac33 and YCplac111 (Gietz, R. D. and Sugino. A. (1988) Gene 74, 527-534).

Methods well known to those skilled in the art can be used to construct expression vectors containing the coding sequence and, for example appropriate transcriptional or translational controls. One such method involves ligation via cohesive ends. Compatible cohesive ends can be generated on the DNA fragment and vector by the action of suitable restriction enzymes. These ends will rapidly anneal through complementary base pairing and remaining nicks can be closed by the action of DNA ligase.

A further method uses synthetic double stranded oligonucleotide linkers and adaptors. DNA fragments with blunt ends are generated by bacteriophage T4 DNA polymerase or *E. coli* DNA polymerase I which remove protruding 3' termini and fill in recessed 3' ends. Synthetic linkers and pieces of blunt-ended double-stranded DNA which contain recognition sequences for defined restriction enzymes, can be ligated to blunt-ended DNA fragments by T4 DNA ligase. They are subsequently digested with appropriate restriction enzymes to create cohesive ends and ligated to an expression vector with compatible termini. Adaptors are also chemically synthesised DNA fragments which contain one blunt end used for ligation but which also possess one preformed cohesive end. Alternatively a DNA fragment or DNA fragments can be ligated together by the action of DNA ligase in the presence or absence of one or more synthetic double stranded oligonucleotides optionally containing cohesive ends.

Synthetic linkers containing a variety of restriction endonuclease sites are commercially available from a number of sources including Sigma-Genosys Ltd, London Road, Pampisford, Cambridge, United Kingdom.

Vectors of the invention thus produced may be used to transform an appropriate host cell for the expression and production of a polypeptide comprising a sequence as defined in the first aspect of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Gooddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al., U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natl. Acad. Sci. USA* 69, 2110 and Sambrook et al (2001) *Molecular Cloning, A Laboratory Manual*, 3rd Ed. Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. Methods for the transformation of *S. cerevisiae* are taught generally in EP 251 744, EP 258 067 and WO 90/01063, all of which are incorporated herein by reference. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming cells and is well known in the art for transforming yeast cell, bacterial cells and vertebrate cells. Methods for transformation of yeast by electroporation are disclosed in Becker & Guarente (1990) *Methods Enzymol.* 194, 182.

Physical methods may be used for introducing DNA into animal and plant cells. For example, microinjection uses a very fine pipette to inject DNA molecules directly into the nucleus of the cells to be transformed. Another example involves bombardment of the cells with high-velocity microprojectiles, usually particles of gold or tungsten that have been coated with DNA.

Plants may be transformed in a number of art-recognised ways. Those skilled in the art will appreciate that the choice of method might depend on the type of plant targeted for transformation. Examples of suitable methods of transforming plant cells include microinjection (Crossway et al., *BioTechniques* 4:320-334 (1986)), electroporation (Riggs et al., *Proc. Natl. Acad. Sci. USA* 83:5602-5606 (1986), *Agrobacterium*-mediated transformation (Hinchee et al, *Biotechnology* 6:915-921 (1988); see also, Ishida et al., *Nature Biotechnology* 14:745-750 (1996) for maize transformation), direct gene transfer (Paszkowski et al., *EMBO J.* 3:2717-2722 (1984); Hayashimoto et al., *Plant Physiol.* 93:857-863 (1990) (rice)), and ballistic particle acceleration using devices available from Agracetus, Inc., Madison, Wis. and Dupont, Inc., Wilmington, Del. (see, for example, Sanford et al., U.S. Pat. No. 4,945,050; and McCabe et al., *Biotechnology* 6:923-926 (1988)). See also, Weissinger et al., *Annual Rev. Genet.* 22:421-477 (1988); Sanford et al., *Particulate Science and Technology* 5:27-37 91987) (onion); Svab et al., *Proc. Natl. Acad. Sci. USA* 87:8526-8530 (1990) (tobacco chloroplast); Christou et al., *Plant Physiol.* 87:671-674 (1988) (soybean); McCabe et al., *Bio/Technology* 6:923-926 (1988) (soybean); Klein et al., *Proc. Natl. Acad. Sci. USA,* 85:4305-4309 (1988) (maize); Klein et al., *Bio/Technology* 6:559-563 (1988) (maize); Klein et al., *Plant Physiol.* 91:440-444 (1988) (maize); Fromm et al., *Bio/Technology* 8:833-839 (1990); and Gordon-Kamm et al., *Plant Cell* 2: 603-618 (1990) (maize); Koziel et al., *Biotechnology* 11:194-200 (1993) (maize); Shimamoto et al., *Nature* 338:274-277 (1989) (rice); Christou et al., *Biotechnology* 9:957-962 (1991) (rice); Datta et al., *Bio/Technology* 8:736-740 (1990) (rice); European Patent Application EP-A-332 581 (orchardgrass and other *Pooideae*); Vasil et al., *Biotechnology* 11:1553-1558 (1993) (wheat); Weeks et al., *Plant Physiol.* 102:1077-1084 (1993) (wheat); Wan et al., *Plant Physiol.* 104:37-48 (1994) (barley); Jahne et al., *Theor. Appl. Genet.* 89:525-533 (1994) (barley); Umbeck et al., *Bio/Technology* 5:263-266 (1987) (cotton); Casas et al., *Proc. Natl. Acad. Sci. USA* 90:11212-11216 (1993) (sorghum); Somers et al., *Bio/Technology* 10:1589-1594 (1992) (oat); Torbert et al., *Plant Cell Reports* 14:635-640 (1995) (oat); Weeks et al., *Plant Physiol.* 102.1077-1084 (1993) (wheat); Chang et al., WO 94/13822 (wheat) and Nehra et al., *The Plant Journal* 5:285-297 (1994) (wheat). *Agrobacterium*-mediated transformation is generally ineffective for monocotyledonous plants for which the other methods mentioned above are preferred.

Generally, the vector will transform not all of the hosts and it will therefore be necessary to select for transformed host cells. One selection technique involves incorporating into the expression vector a DNA sequence marker, with any necessary control elements, that codes for a selectable trait in the transformed cell. These markers include dihydrofolate reductase, G418 or neomycin resistance for eukaryotic cell culture, and tetracyclin, kanamycin or ampicillin resistance genes for culturing in *E. coli* and other bacteria. Alternatively, the gene for such selectable trait can be on another vector, which is used to co-transform the desired host cell.

The marker gene can be used to identify transformants but it is desirable to determine which of the cells contain recombinant DNA molecules and which contain self-ligated vector molecules. This can be achieved by using a cloning vector where insertion of a DNA fragment destroys the integrity of one of the genes present on the molecule. Recombinants can therefore be identified because of loss of function of that gene.

Another method of identifying successfully transformed cells involves growing the cells resulting from the introduction of an expression construct of the present invention to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the mature protein in the supernatant of a culture of a transformed cell can be detected using antibodies.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

Accordingly, in a fourth aspect of the present invention there is provided a cell culture comprising a cell according to the third aspect of the invention and culture medium. Typically the culture medium will contains mature polypeptide that results from the expression of a polypeptide according to the first aspect of the present invention within the expression system and, usually, by further translational processing, such as the removal of the pre and/or pro sequences.

Methods for culturing prokaryotic host cells, such as *E. coli*, and eukaryotic host cells, such as mammalian cells are well known in the art. Methods for culturing yeast are generally taught in EP 330 451 and EP 361 991.

Allowing host cells that have been transformed by the recombinant DNA of the invention to be cultured for a sufficient time and under appropriate conditions known to those skilled in the art in view of the teachings disclosed herein permits the expression of the polypeptide according to the first aspect of the present invention. The thus produced polypeptide may be further processed by the host cell, such that the pre and/or pro sequences are removed. Accordingly the "mature" desired protein may differ from the protein as originally translated.

Thus the invention also provides, as a fifth aspect, a process for producing a mature desired protein as defined above. The process comprises the step of culturing a cell according to the third aspect of the invention in a culture medium wherein the cell, as a result of the expression of a polypeptide as defined in the first aspect of the invention, secretes a mature desired protein, where it accumulates either in the periplasmic space, the culture medium or both, but preferably into the culture medium. The culture medium, which contains the secreted desired protein, may then be separated from the cell(s) in the cell culture. Secreted proteins associated with the cell wall can generally be disassociated therefrom using lytic enzymes under osmotic supporting (e.g. sorbitol) conditions (which gently release the secreted protein selectively). See Elango et al., *J. Biol. Chem.* 257: 1398-1400 (1982). Examples of lytic enzymes suitable for this purpose include lyticase, Zymolyase-60,000, and Glusulase, all of which are commercially available, for example, the case of the latter two, from Seikagaku Kogyo or Kirin Brewery, and from Boehringer Mannheim, respectively.

Preferably, following the isolation of the culture medium, the mature desired protein is separated from the medium. Even more preferably the thus obtained mature desired protein is further purified.

The desired mature protein may be extracted from the culture medium by many methods known in the art. For example purification techniques for the recovery of recombinantly expressed albumin have been disclosed in: WO 92/04367, removal of matrix-derived dye; EP 464 590, removal of yeast-derived colorants; EP 319 067, alkaline precipitation and subsequent application of the albumin to a lipophilic phase; and WO 96/37515, U.S. Pat. No. 5,728,553 and WO 00/44772, which describe complete purification processes; all of which are incorporated herein by reference. Proteins other than albumin may be purified from the culture medium by any technique that has been found to be useful for purifying such proteins, since the modified leader sequence of the invention will not affect the mature protein per se.

Such well-known methods include ammonium sulphate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

The resulting protein may be used for any of its known utilities, which, in the case of albumin, include i.v. administration to patients to treat severe burns, shock and blood loss, supplementing culture media, and as an excipient in formulations of other proteins.

Although it is possible for a therapeutically useful desired protein obtained by a process of the of the invention to be administered alone, it is preferable to present it as a pharmaceutical formulation, together with one or more acceptable carriers or diluents. The carrier(s) or diluent(s) must be "acceptable" in the sense of being compatible with the desired protein and not deleterious to the recipients thereof. Typically, the carriers or diluents will be water or saline which will be sterile and pyrogen free.

Thus, a sixth aspect of the present invention provides a process wherein a desired protein, obtained by a process according to the fifth aspect of the invention, is formulated with a therapeutically acceptable carrier or diluent thereby to produce a therapeutic product suitable for administration to a human or an animal.

The therapeutic product may conveniently be presented in unit dosage form and may be prepared by any of the methods well known in the art of pharmacy. Preferred unit dosage products are those containing a daily dose or unit, daily sub-dose or an appropriate fraction thereof, of an active ingredient.

It should be understood that in addition to the ingredients particularly mentioned above the therapeutic product may include other agents conventional in the art having regard to the type of product in question.

The invention will now be described in more detail by reference to the following non-limiting Figures and Examples wherein:

FIG. 1 shows a comparison of a natural HSA leader (having pre and pro regions) (top line) with a fused HSA/MFα-1 leader sequence as disclosed in WO 90/01063 (second line) and a preferred modified leader sequence of the present invention (third line).

FIG. 2 shows the standard genetic code.

FIG. 3 shows a modified list of preferred *S. cerevisiae* codons.

FIG. 15 shows plasmid maps of pAYE638 and pAYE642.

Figure 20:
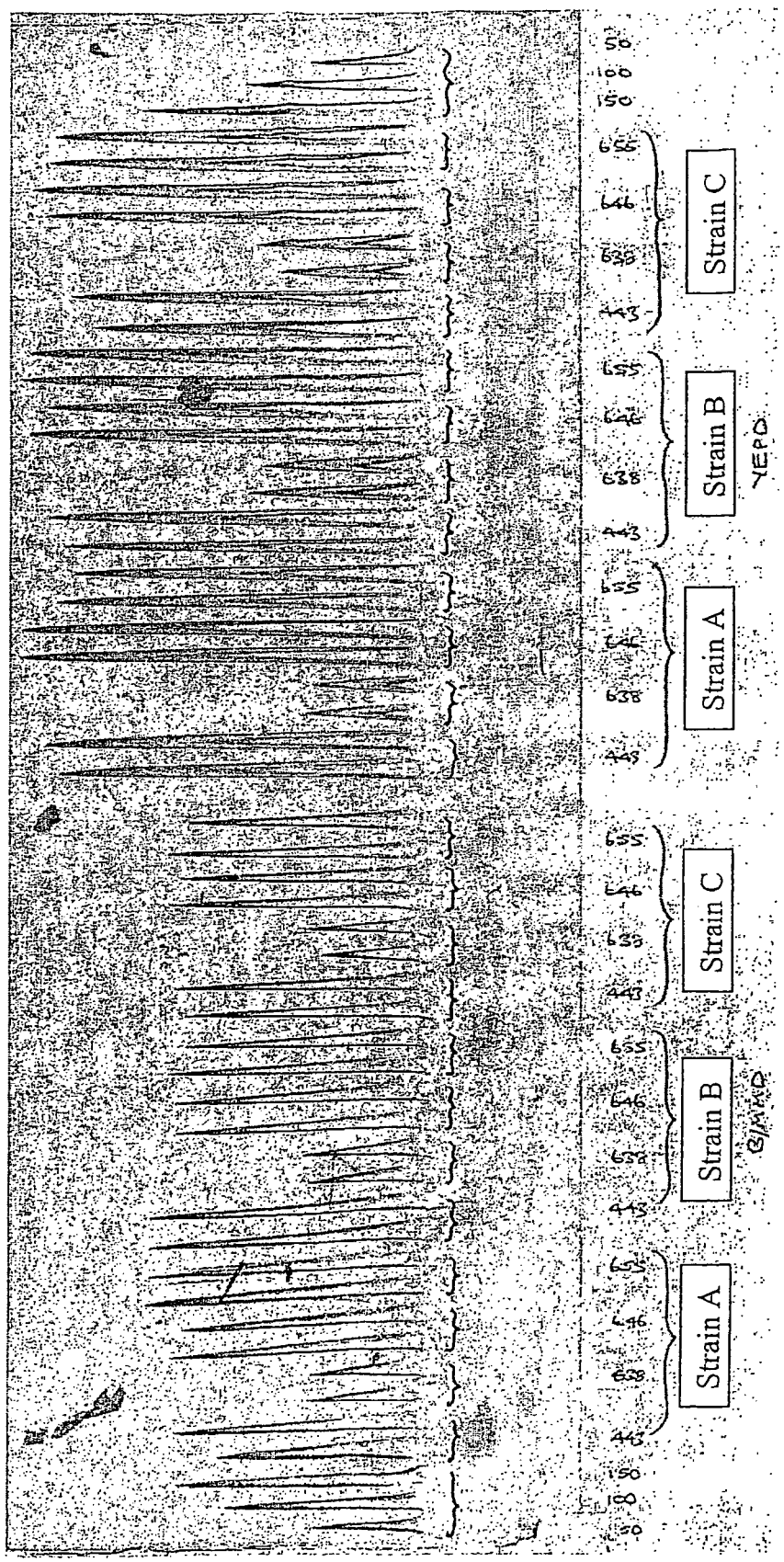

FIG. 20 shows an analysis of rHA productivity by rocket immunoelectrophoresis. Yeast were cultured in YEP, 2% (w/v) sucrose or B/MM) 2% (w/v) sucrose for 72 hr, 200 rpm at 30° C. Quantitation was performed by reference to HSA standards (mg·L$^{-1}$).

FIG. 21 shows the albumin-productivity in high cell density fermentation. *Means that the human albumin level was too low to quantitate.

FIG. 22 summarises the characteristics of the constructs used in the examples.

EXAMPLE 1

The *Saccharomyces cerevisiae* PRB1 promoter was isolated from yeast genomic DNA by PCR using two single stranded oligonucleotides PRBJM1 and PRBJM2:

```
                                          SEQ ID NO: 35
PRBJM1
5'-GCATGCGGCCGCCCGTAATGCGGTATCGTGAAAGCG-3'

SEQ ID NO: 36
PRBJM2
5'GCATAAGCTTACCCACTTCATCTTTGCTTGTTTAG-3'
```

Figure 4:
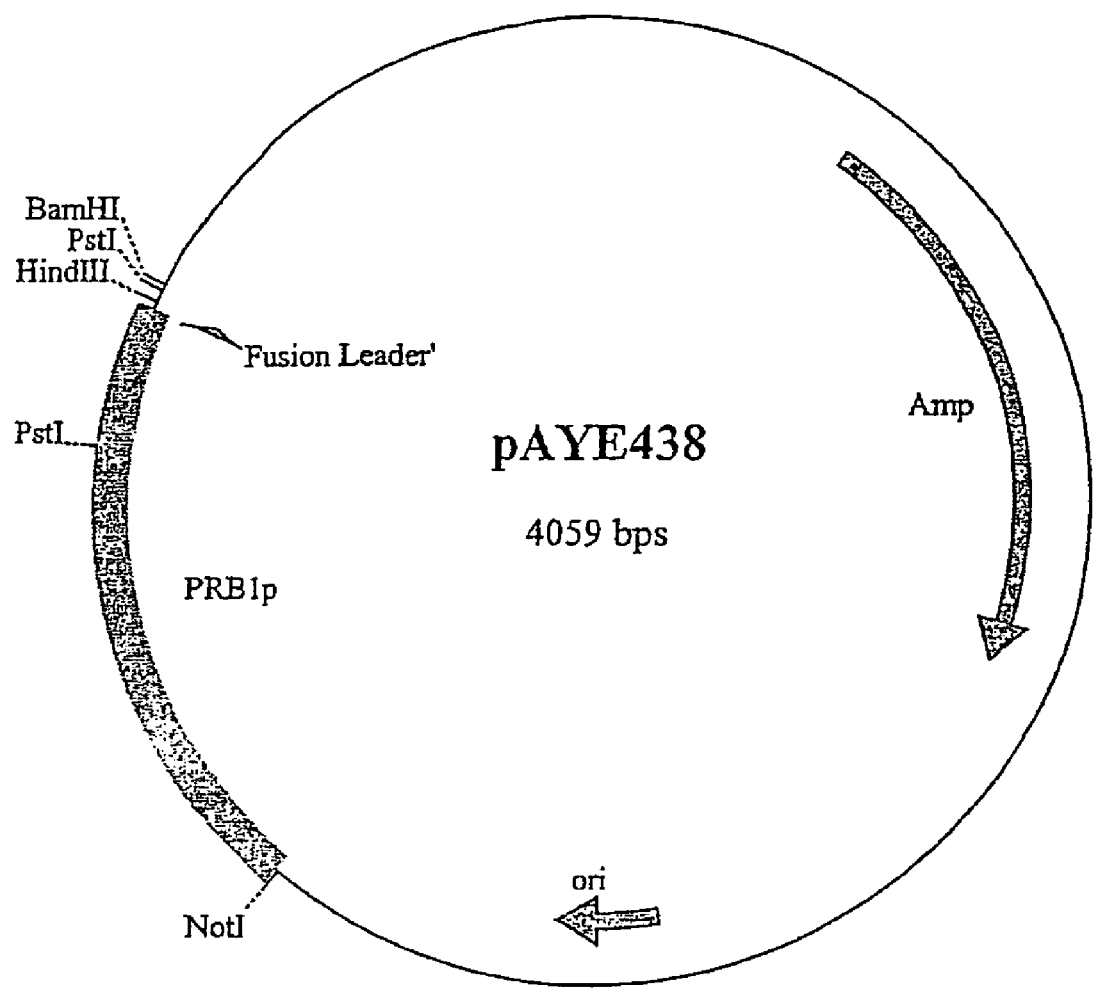
FIG. 4 shows a plasmid map of pAYE438.
Figure 5:
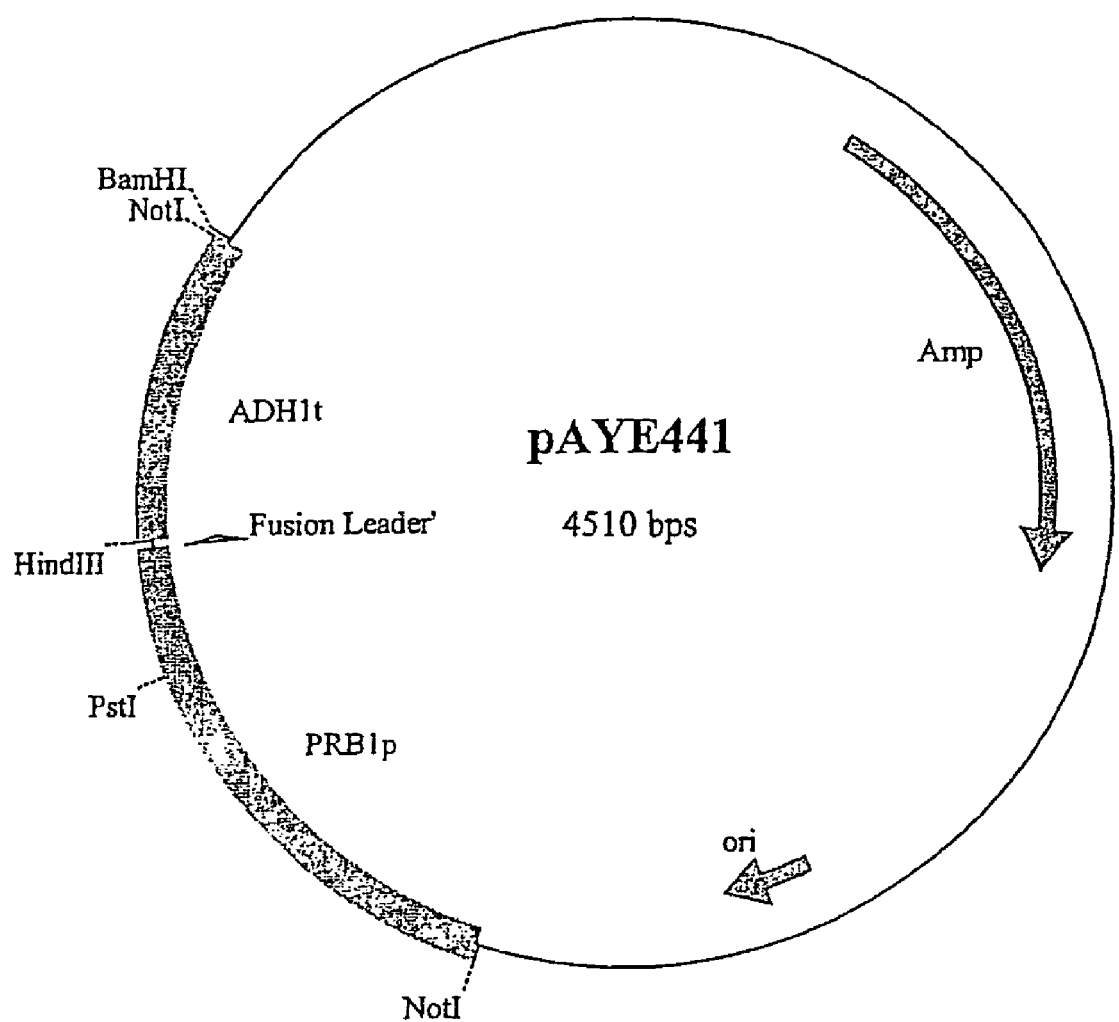
FIG. 5 shows a plasmid map of pAYE441.
Figure 6:
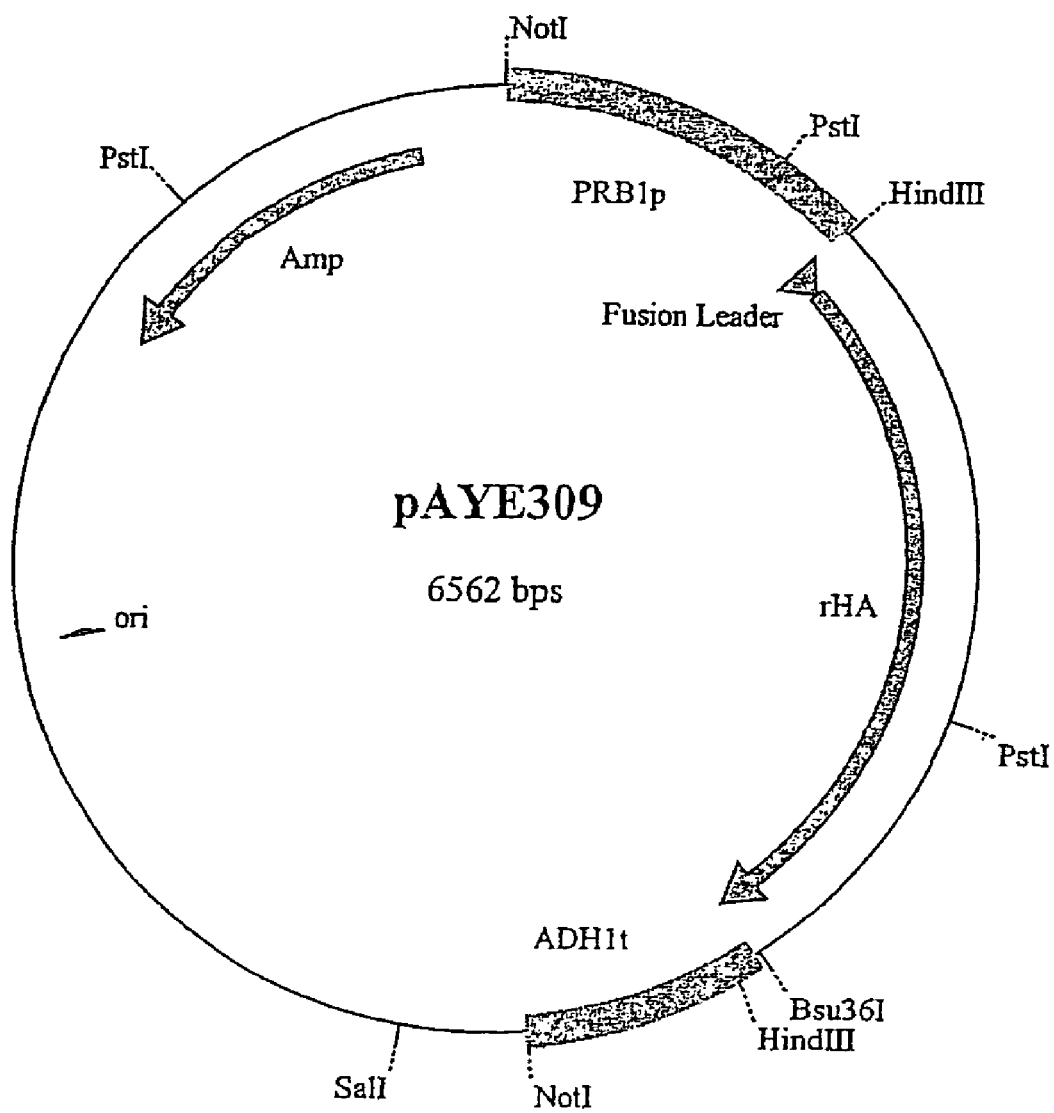
FIG. 6 shows a plasmid map of pAYE309.

The PCR conditions 40 cycles of 94° C. for 30 seconds, 50° C. for 40 seconds, 72° C. for 120 seconds, followed by 72° C. for 600 seconds, followed by a 4° C. hold. The 0.85 kb DNA fragment was digested with both NotI and HindIII and ligated into pBST+, described in WO 97/24445, similarly digested with NotI and HindIII, to create plasmid pAYE438 (FIG. 4). Plasmid pAYE438 was digested with HindIII and BamHI and ligated with the 0.48 kb HindIII/BamHI ADH1 terminator DNA fragment from pAYE440 previously disclosed in WO 00/44772, so as to create plasmid pAYE441 (FIG. 5). Plasmid pAYE441 was linearised at the unique HindIII site and ligated with the 1.8 kb HindIII/Bsu36I fragment from pAYE309 (FIG. 6) previously disclosed (Sleep, D. et al. (1991) Bio/

Technology 9, 183-187 and EP-A-0 431 880 and the double stranded oligonucleotide linker

Figure 7:
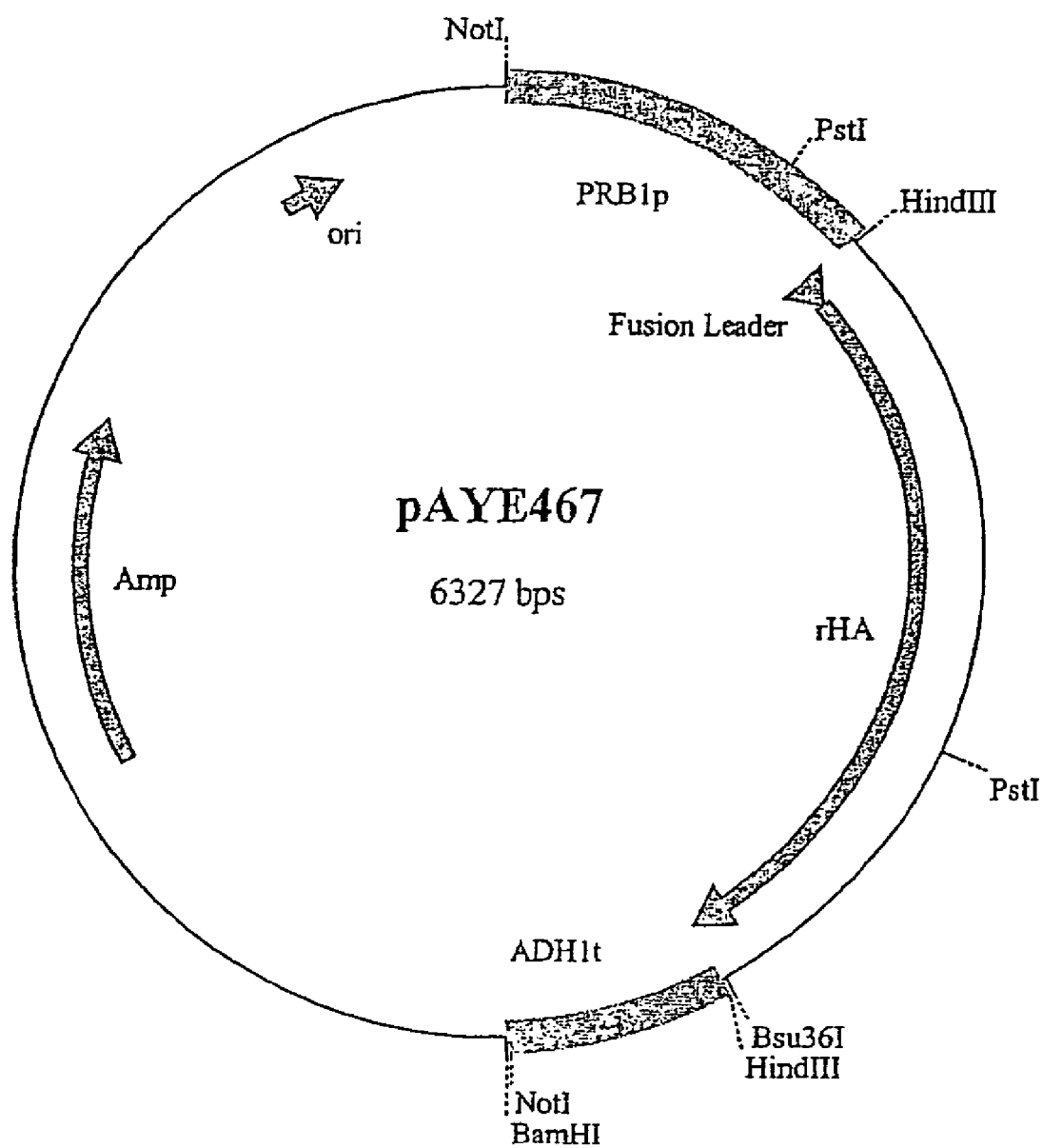
FIG. 7 shows a plasmid map of pAYE467.
Figure 8:
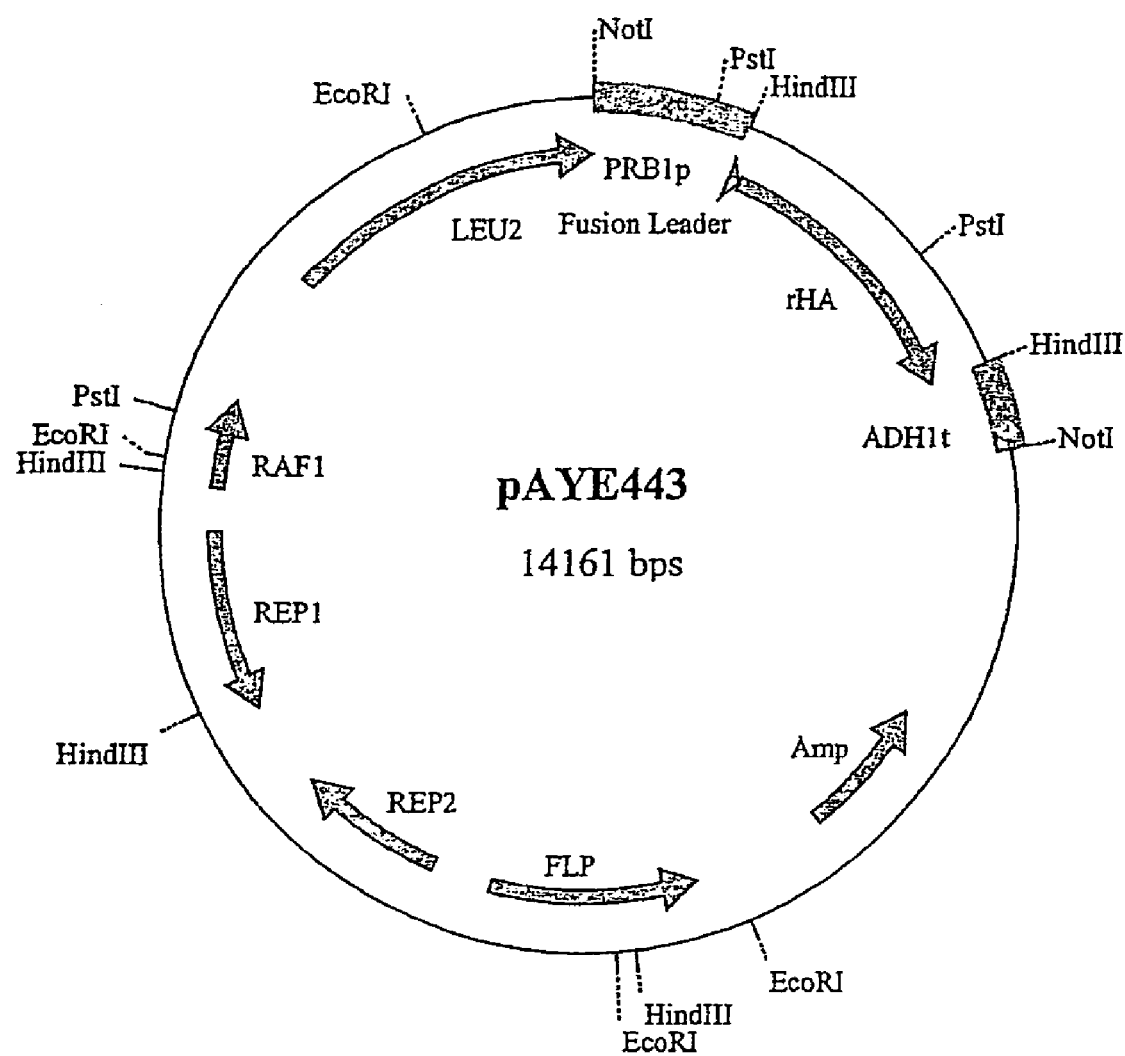
FIG. 8 shows a plasmid map of pAYE443.

```
        5'-TTAGGCTTATA-3'           SEQ ID NO: 37
            3'-CCGAATATTCGA-5'      SEQ ID NO: 38
``` so as to create pAYE467 (FIG. 7). The 3.2 kb NotI, expression cassette from pAYE467 was ligated into NotI linearised pSAC35 (Sleep et al. (1991), *Bio/technology* 9: 183-187), which had been previously treated with calf intestinal phosphatase (CIP) to create plasmid pAYE443 (FIG. 8). SEQ IQ No 22 shows a polynucleotide sequence that comprises the coding region of the HSA/MFα-1 fusion leader sequence and the mature human albumin coding region to be found within the DNA sequence of both pAYE467 and pAYE443. The polynucleotide sequence encoding the HSA/MFα-1 fusion leader sequence was modified by site directed mutagenesis with a single stranded oligonucleotide called CPK1 with the DNA sequence:

```
                                        SEQ ID No 23
5'-CT AAA GAG AAA AAG AAT GGA GAC GAT GAA TAC CCA
                         Ile⁻¹⁶ Val⁻¹⁸ Ile⁻¹⁹Phe⁻²⁰
CTT CAT CTT TGC-3'
```

Site directed mutagenesis (SDM) was performed according to standard, protocols (Botstein and Shortle, "Strategies and Applications of In Vitro Mutagenesis," *Science*, 229: 193-1210 (1985) incorporated herein by reference) although or other suitable techniques could also be used. The nucleotide sequence of CPK1 was designed to modify the amino acid sequence of the HSA/MFα-1 fusion leader sequence to introduce the following mutations Thr-20Phe, Phe-19Ile, Ile-18Val and Leu-16Ile, where the numbering (−20 etc) is such that the −1 residue is the C-terminal amino acid of HSA/MFα-1 fusion leader sequence.

Figure 9:
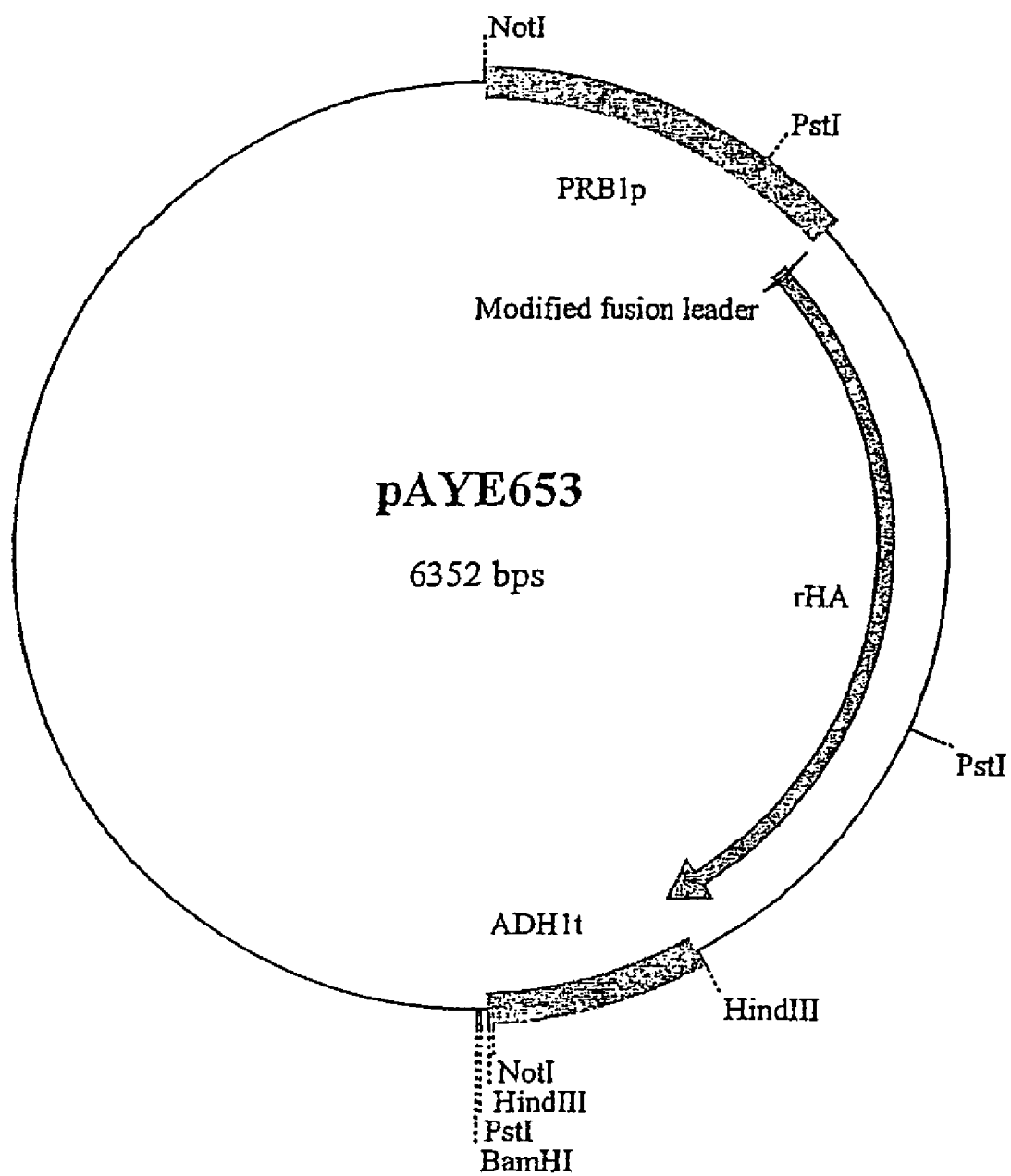
FIG. 9 shows a plasmid map of pAYE653.

The DNA sequence of the mutagenised plasmid was confirmed by dideoxynucleotide sequencing which confirmed that the polynucleotide sequence had been mutagenised to the desired sequence and that no other DNA sequence alterations had been introduced. The new plasmid was named pAYE653 (FIG. 9). SEQ IQ No 24 shows a polynucleotide sequence that comprises the coding region of the modified HSA/MFα-1 fusion leader sequence and SEQ IQ No 25 shows a polynucleotide sequence that comprises the coding region of the modified HSA/MFα-1 fusion leader sequence and the mature human albumin coding region to be found within the polynucleotide sequence of pAYE653.

Figure 10:
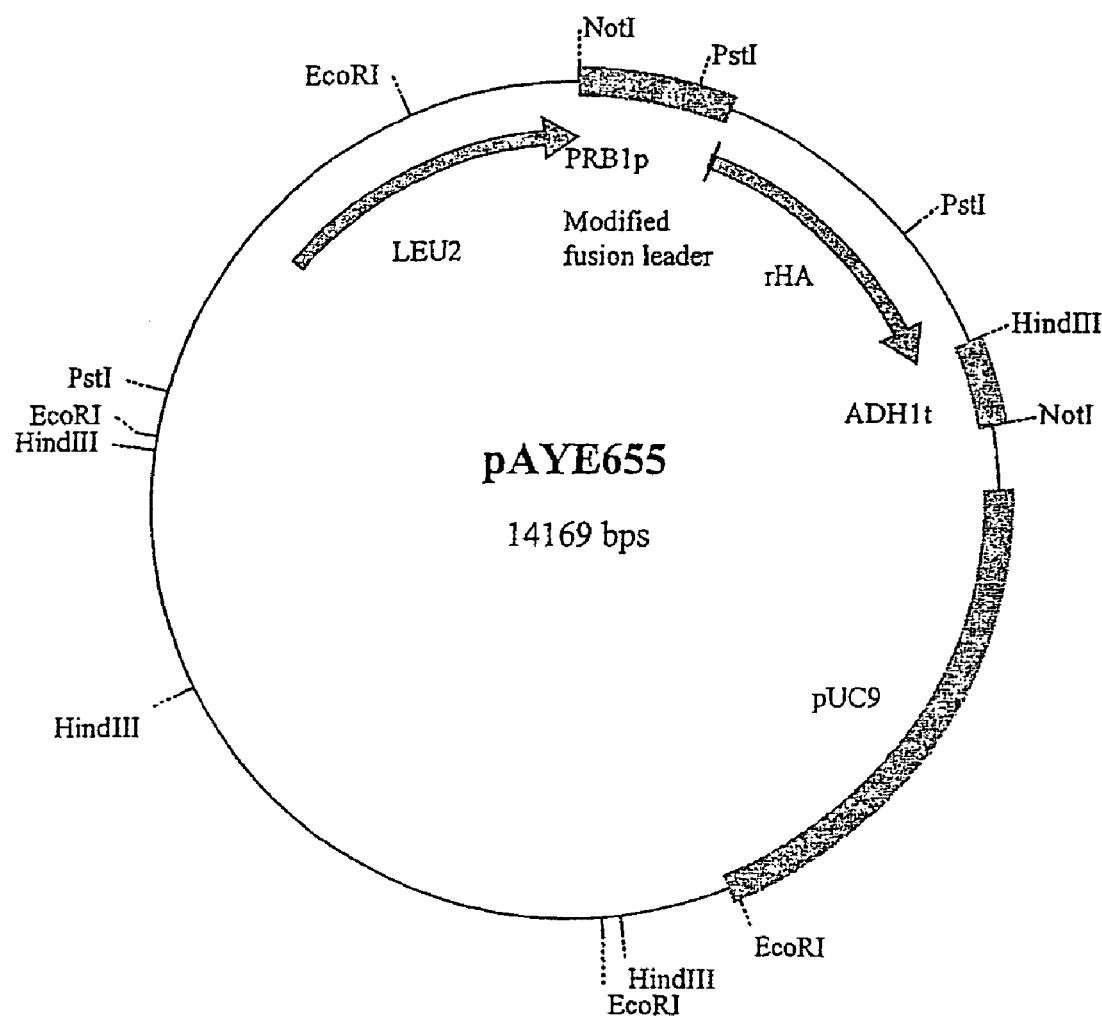
FIG. 10 shows a plasmid map of pAYE655.

The NotI human albumin expression cassette was isolated from pAYE653 and ligated into the unique NotI site of plasmid pSAC35 to generate plasmids pAYE655 (FIG. 10).

EXAMPLE 2

SEQ ID No 19 shows a DNA sequence that comprises: a non-coding region that includes a 5' UTR from the *Saccharomyces cerevisiae* PRB1 promoter; a polynucleotide region encoding the modified HSA/MFα-1 fusion leader sequence of the invention; a codon optimised coding region for mature human albumin and translation termination sites.

As a control with which to compare the effects of the sequence modifications provided to the leader sequence in SEQ ID No 19, SEQ ID No 40 shows a DNA sequence that is essentially the same as SEQ ID No 19, except that, instead of the 15 polynucleotide region representing the second aspect of the invention, the DNA sequence of SEQ ID No 40 comprises an 15 polynucleotide region encoding the 5 amino acids of an unmodified HSA/MFα-1 fusion leader sequence, namely SFISL.

Both DNA sequences were synthesised by Genosys, Inc (Cambridge, UK) from overlapping single-stranded oligonucleotides.

Figure 11:
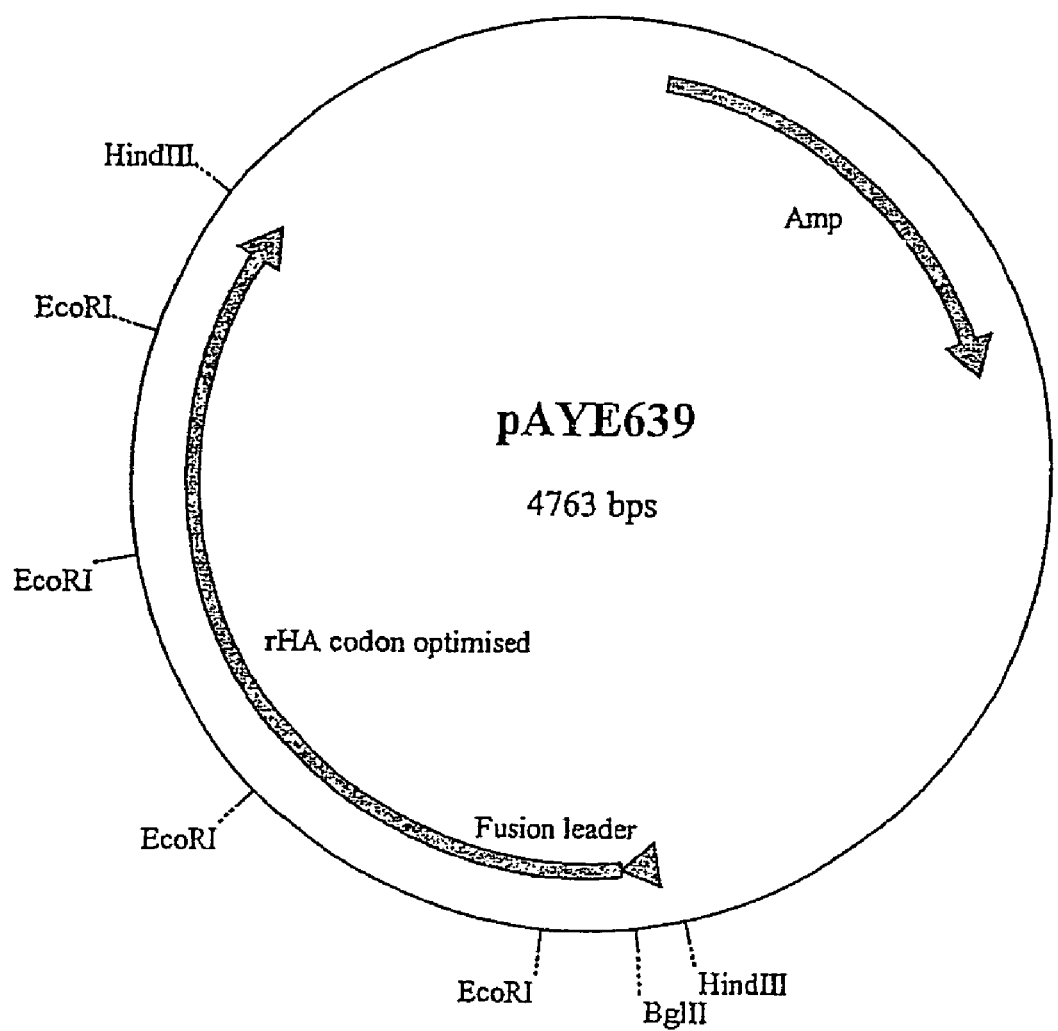
FIG. 11 shows a plasmid map of pAYE639.

SEQ ID No 40 was synthesised as a 1.865 kb SacI-HindIII DNA fragment cloned into the SacI-HindIII sites of plasmid pBSSK- (Stratagene Europe, P.O. Box 12085, Amsterdam, The Netherlands), as plasmid pAYE639 (FIG. 11).

The *Saccharomyces cerevisiae* PRA1 promoter was isolated from yeast genomic DNA by PCR using two single stranded oligonucleotides PRBJM1 and PRBJM3:

```
                                        SEQ ID NO: 39
PRBJM3
5'-GTTAGAATTAGGTTAAGCTTGTTTTTTTATTGGCGATGAA-3'
```

Figure 12:
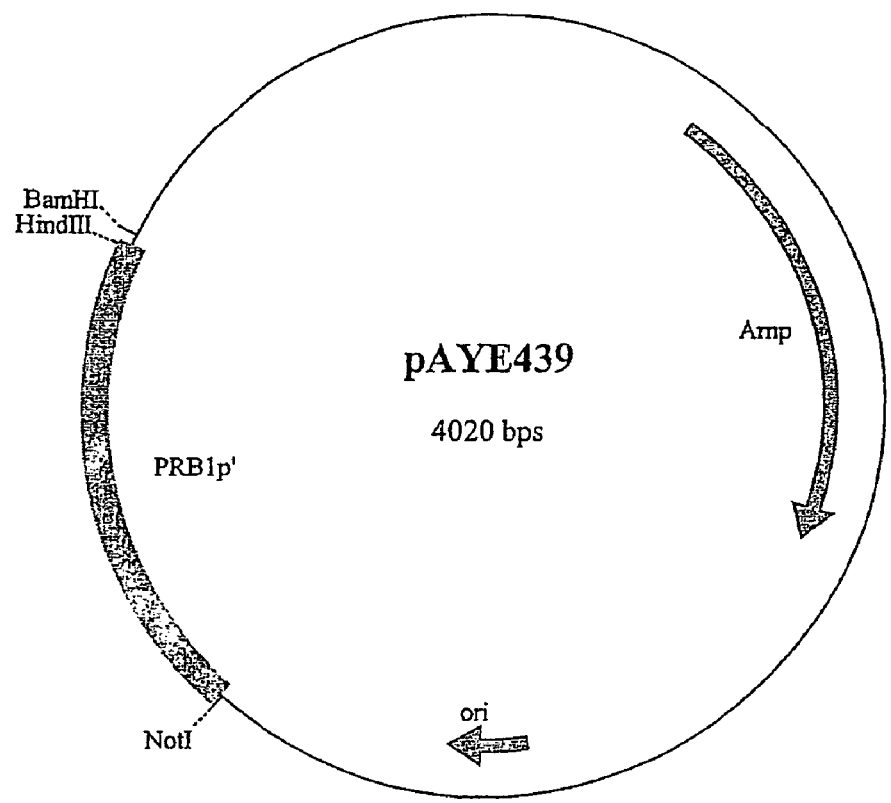
FIG. 12 shows a plasmid map of pAYE439.
Figure 13:
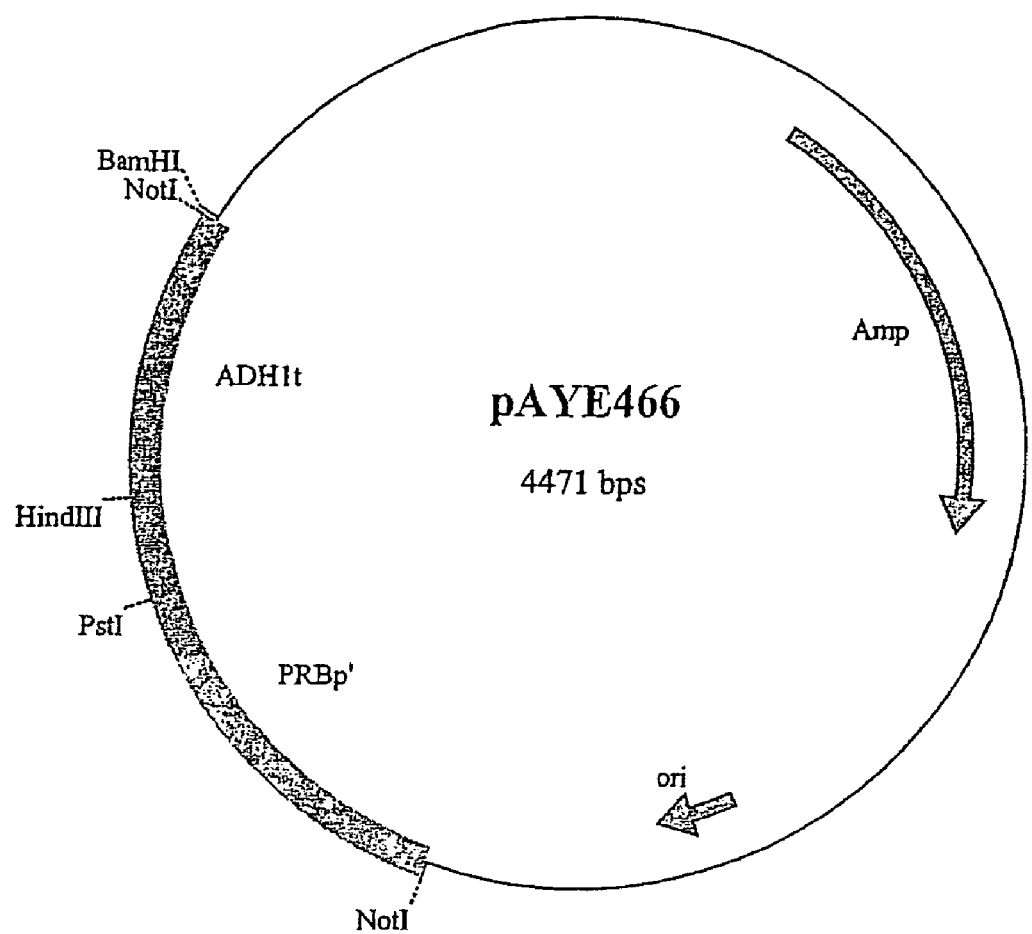
FIG. 13 shows a plasmid map of pAYE466.

The PCR conditions 40 cycles of 94° C. for 30 seconds, 50° C. for 40 seconds, 72° C. for 120 seconds, followed by 72° C. for 600 seconds, followed by a 4° C. hold. The 0.81 kb DNA fragment was digested with both NotI and HindIII and ligated into pBST+, described in WO 97/24445, similarly digested with NotI and HindIII, to create plasmid pAYE439 (FIG. 12). Plasmid pAYE439 was digested with HindIII and BamHI and ligated with the 0.48 kb HindIII/BamHI ADH1 terminator DNA fragment from pAYE440 previously disclosed in WO 00/44772, so as to create plasmid pAYE466 (FIG. 13).

Figure 14:
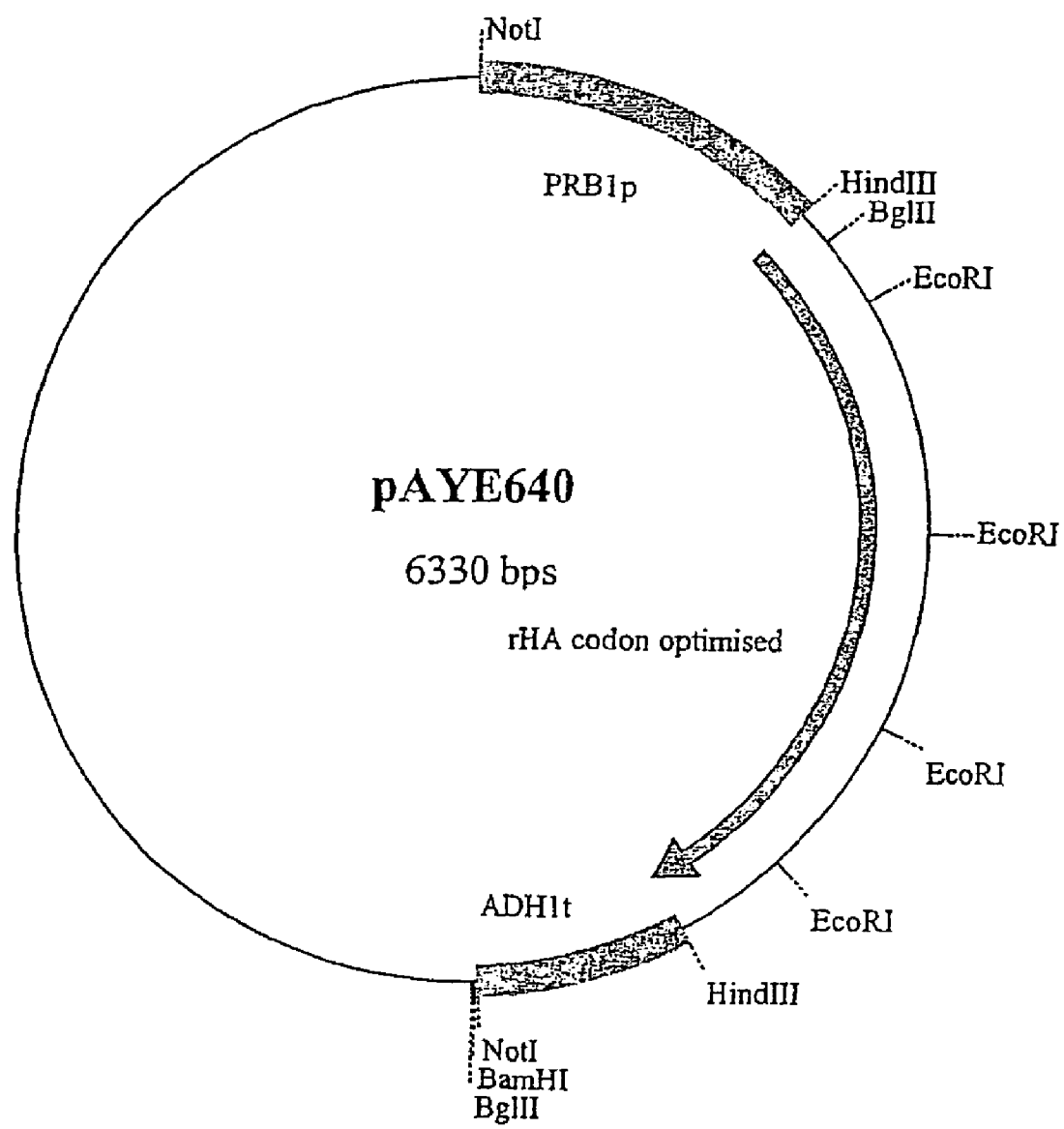
FIG. 14 shows a plasmid map of pAYE640.

A 1.865 kb HindIII DNA fragment of SEQ ID No 40 was cloned into the unique HindIII site of plasmid pAYE466 to create plasmid pAYE640, which was shown to contain the 1.865 kb HindIII DNA fragment of SEQ ID No 40 between the PRB1 promoter and the ADH1 terminator in the correct orientation for expression from the PRB1 promoter (FIG. 14).

Plasmid pAYE640 was digested to completion with NotI/PvuI and the NotI 3.2 kb, PRB1 promoter/HindIII DNA fragment of SEQ ID No 40 gene/ADH1 terminator expression cassette was purified. A NotI/PvuI double digest of pAYE640 was preferable to a single NotI digestion because the expression cassette (3.2 kb) and pBST+ plasmid backbone (3.15 kb) were similar in size. The 3.2 kb NotI, expression cassette from pAYE640 was ligated into NotI linearised pSAC35 (Sleep et al. (1991), *Bio/technology* 9: 183-187), which had been previously treated with calf intestinal phosphatase (CIP) to create plasmid pAYE638 (FIG. 15). Plasmid pAYE638 was shown to contain the NotI HSA expression cassette inserted into the NotI site of pSAC35 and orientated so that the expression of the HSA gene was away from the LEU2 auxotrophic marker and toward the 2 μm origin of replication. Plasmid pAYE642 contained the same HSA expression cassette but arranged in the opposite orientation (FIG. 15).

Figure 16:
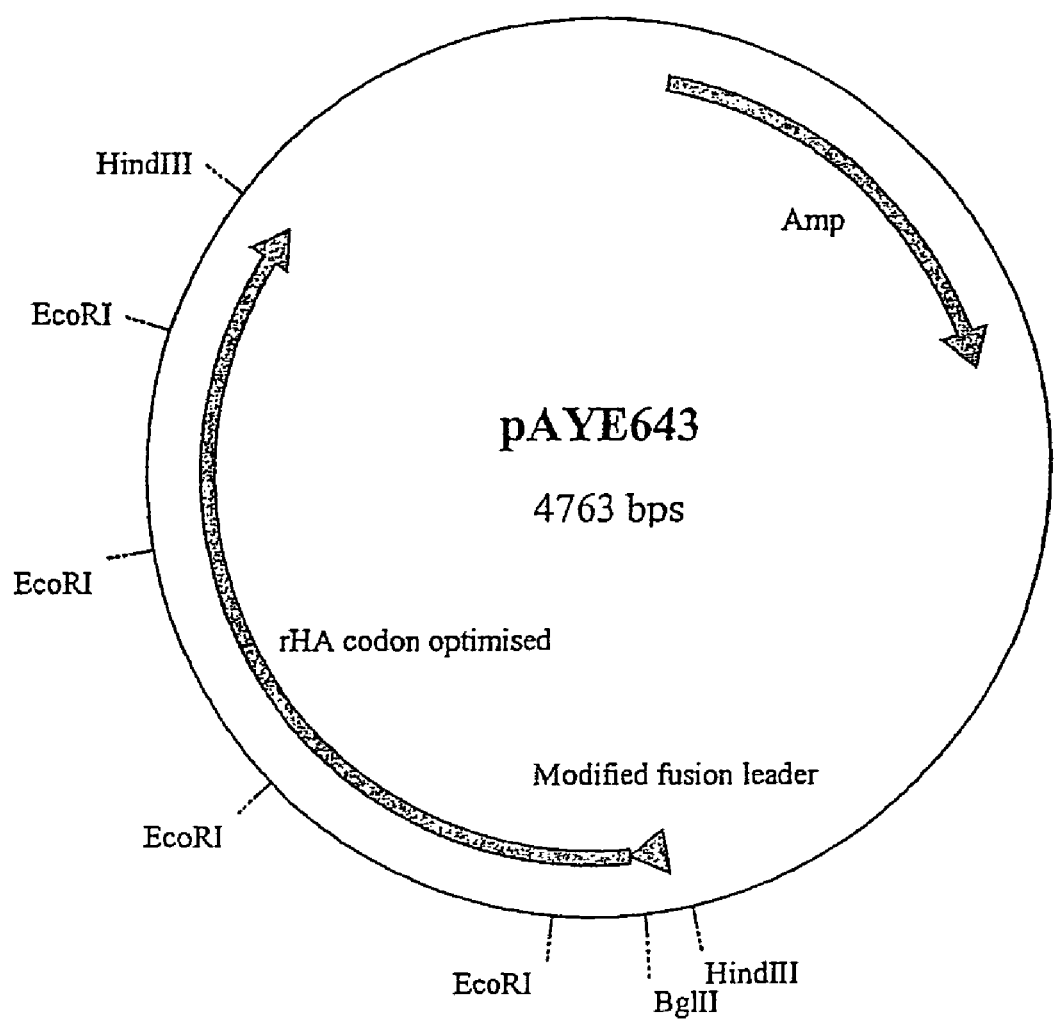
FIG. 16 shows a plasmid map of pAYE643.
Figure 17:
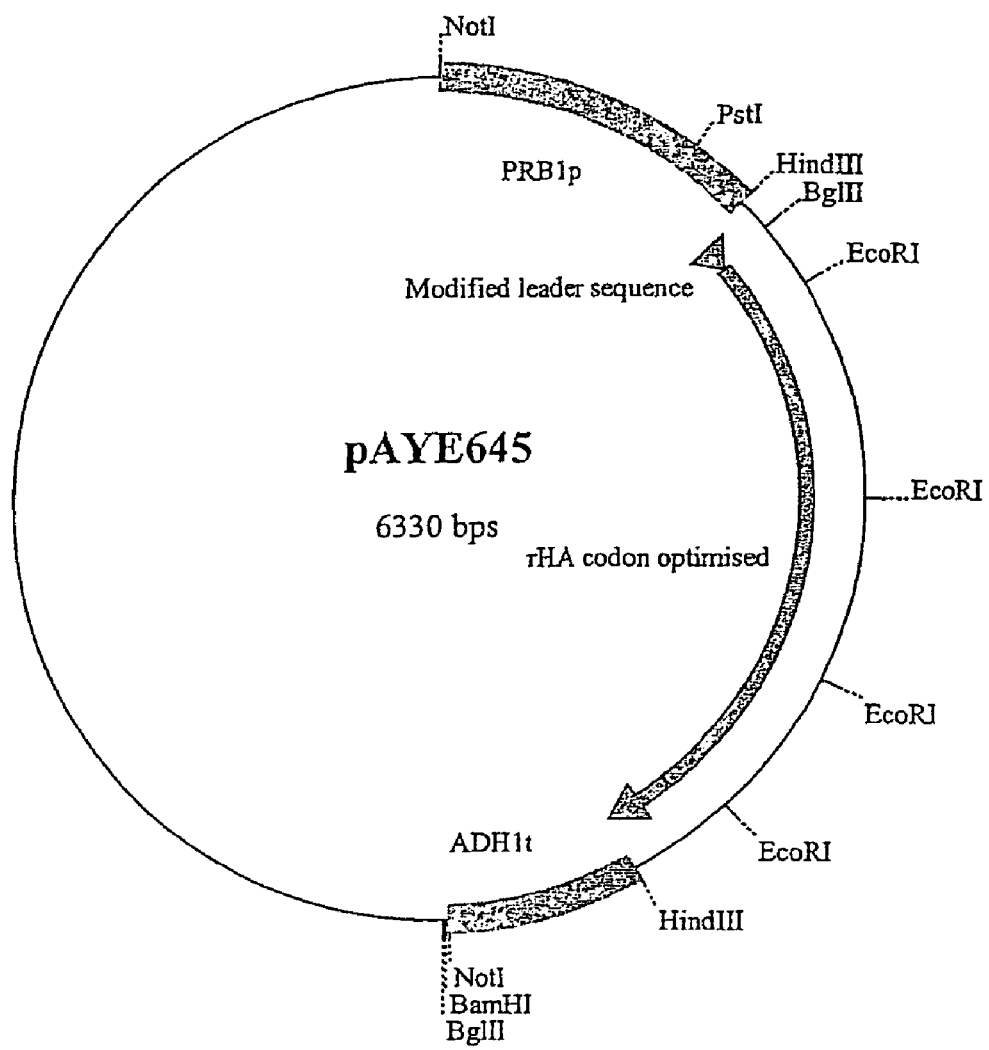
FIG. 17 shows a plasmid map of pAYE645.
Figure 18:
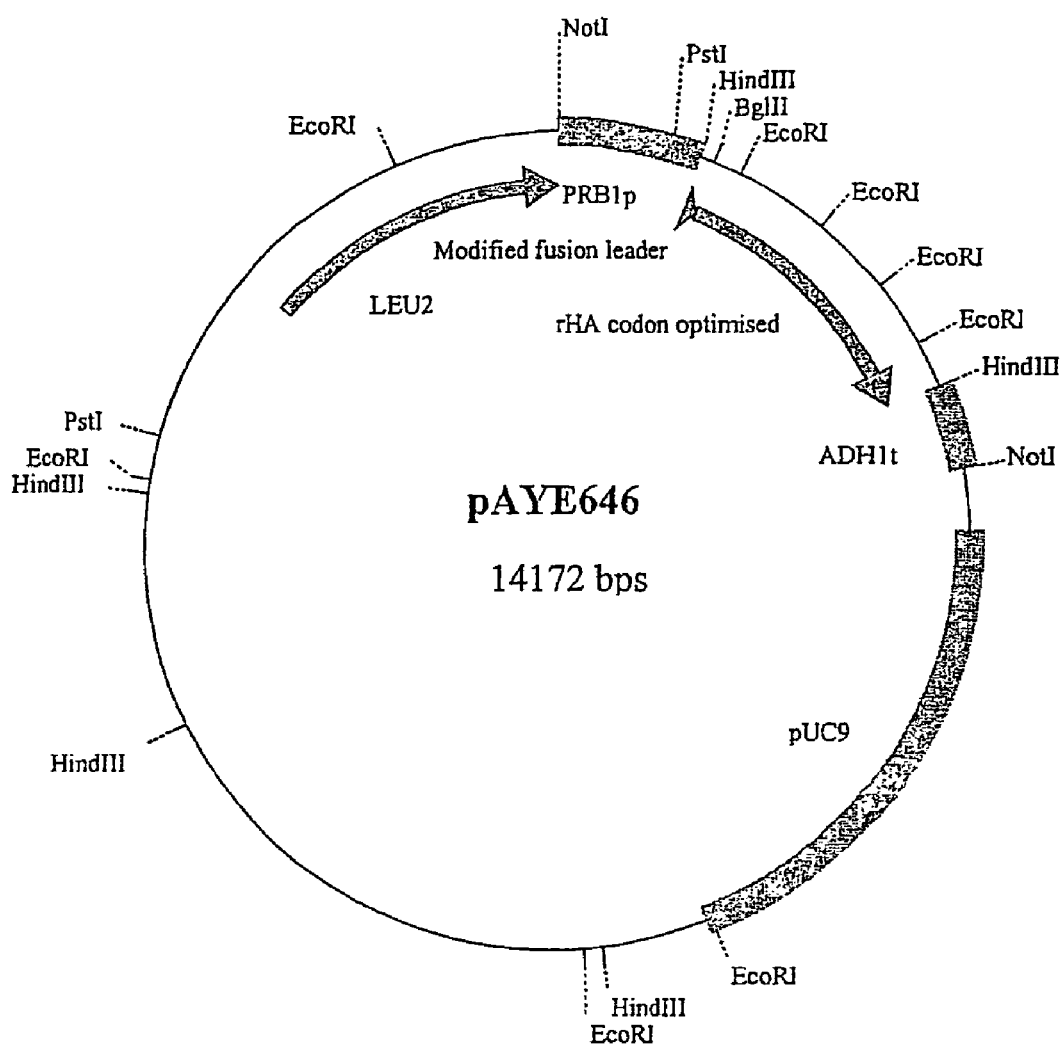
FIG. 18 shows a plasmid map of pAYE646.
Figure 19:
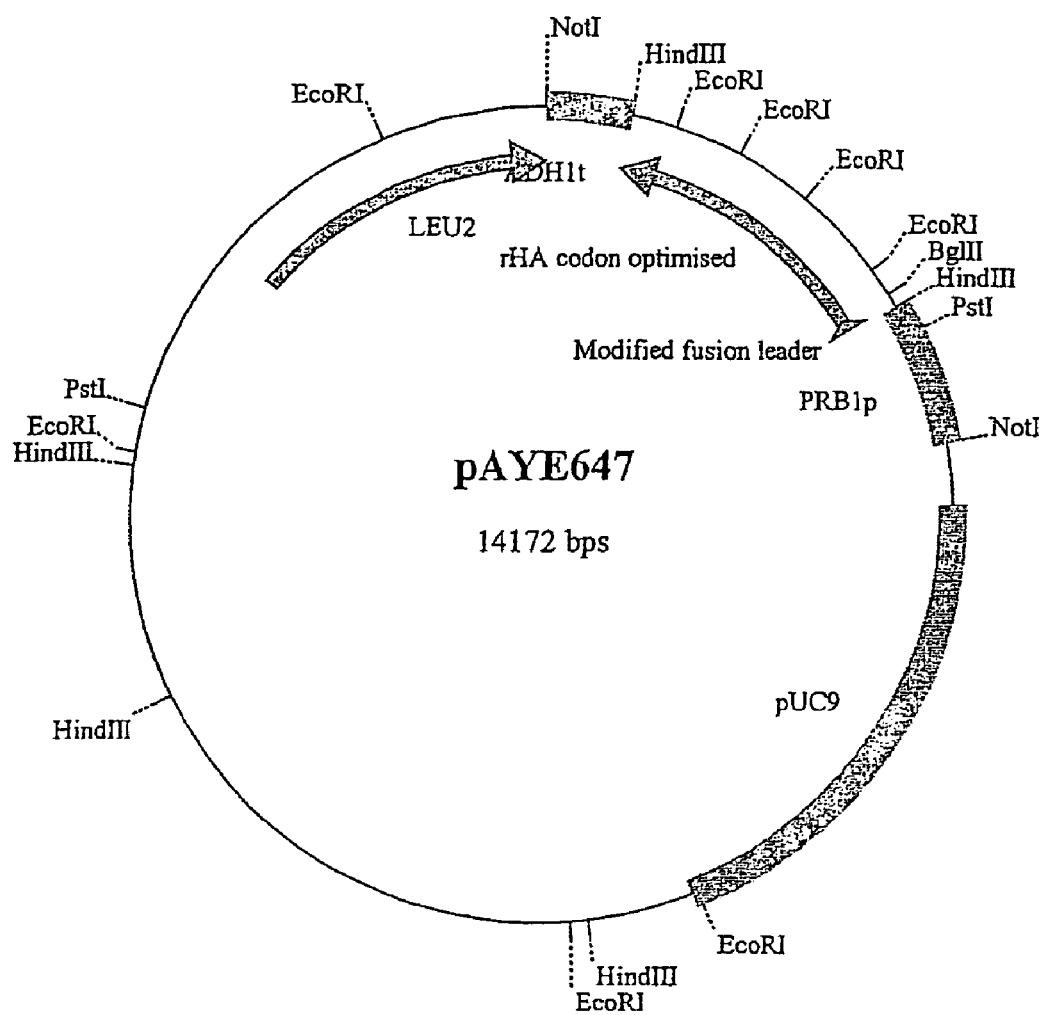
FIG. 19 shows a plasmid map of pAYE647.

SEQ ID No 19 was synthesised as a 1.865 kb SacI-HindIII DNA fragment cloned into pBSSK- (Stratagene Europe, P.O. Box 12085, Amsterdam, The Netherlands), as plasmid pAYE643 (FIG. 16). The DNA sequence which encodes for an HSA/MFα-1 fusion leader sequence-albumin fusion within pAYE643 is given in SEQ ID No 27. The 1.865 kb HindIII fragment of SEQ ID No 19 was isolated from pAYE643 and ligated into the unique HindIII site of pAYE466 to create plasmid pAYE645 (FIG. 17). The NotI PRB1 rHA expression cassette was isolated from pAYE645 by digestion with NotI/PvuI, and ligated into the unique NotI site of pSAC35 to generate plasmids pAYE646 (FIG. 18) and pAYE647 (FIG. 19). The NotI expression cassette within plasmid pAYE646 was orientated in the same direction as plasmid pAYE638 and pAYE443, while the NotI expression cassette within plasmid pAYE647 was orientated in the opposite orientation and was the same as plasmid pAYE642.

EXAMPLE 3

Three different yeast strains, A, B and C, were transformed to leucine prototrophy with plasmids pAYE443, pAYE638, pAYE646 and pAYE655. The transformants were patched out onto Buffered Minimal Medium (BMM, described by Kerry-Williams, S. M. et al. (1998) Yeast 14, 161-169) containing 2% (w/v) glucose (BMMD) and incubated at 30° C. until grown sufficiently for further analysis. The human albumin productivity of the transformants was analysed from 10 mL YEP (1% (w/v) yeast extract; 2% (w/v) bacto peptone) containing 2% (w/v) glucose (YEPD) and BMMD shake flask culture (30° C., 200 rpm, 72 hr) by rocket immunoelectrophoresis of cell free culture supernatant (FIG. 20).

The results showed that the human albumin productivity of all three strains transformed with pAYE638 was approximately 4-5 fold lower than that observed in the same strain transformed with pAYE443 (which both contained the HSA/MFα-1 fusion leader sequence, but encoded by different polynucleotide sequences) in both rich and defined media. Unexpectedly, the human albumin productivity of all three strains transformed with pAYE646 or pAYE655 was significantly higher than that observed with pAYE638 and similar or slightly greater than that observed for the same strains transformed with pAYE443.

EXAMPLE 4

Yeast strain C [pAYE443], strain C [pAYE655], strain C [pAYE638] and strain C [pAYE646], and strain B [pAYE443] and strain B [pAYE646] were cultivated in high cell density fermentation in both fed-batch and fill & draw procedures. The fed-batch procedure used a medium and control parameters as described in WO 96/37515. The fill & draw procedure used the fed-batch procedure as described above, but additionally included the steps that: upon completion of the feed phase of the fed-batch culture procedure, 90% of the culture volume was removed from the fermenter vessel; and batch medium was added to the remaining 10% volume of the culture (maintaining pH control) prior to the initiation of feed addition, using the medium and control parameters described in WO 96/37515. The human albumin productivity ($Y_{P/S}$) and human albumin concentration (g/L) were assessed by scanning densitometry of SDS-PAGE of cell free whole culture. The biomass yield ($Y_{X/S}$) was also calculated from gravimetric determinations. The results (FIG. 21) indicated that, as seen previously in Example 3, the human albumin productivity ($Y_{P/S}$) and human, albumin concentration (g/L) of yeast strains containing the human albumin expression plasmid pAYE638 (native polypeptide sequence but yeast-biased codons) had significantly lower productivity than the same strains containing the human albumin expression plasmid pAYE443 (native polypeptide sequence and natural codon bias for leader and mature albumin) even though the amino acid sequences of both the HSA/MFα-1 fusion leader sequence and the mature human albumin were identical.

When the strain C fermentations were run in fed-batch mode a 16% and 12% increase in human albumin productivity ($Y_{P/S}$) relative to that of Strain C [pAYE443] was observed when Strain C [pAYE655] and Strain C [pAYE646] (human albumin expression plasmids incorporating a modified leader sequence in accordance with the present invention) were each cultured for a comparable length of time, respectively. When the strain B fermentations were run in fed-batch mode a 24% increase in human albumin productivity ($Y_{P/S}$) relative to that of Strain B [pAYE443] was observed when Strain B [pAYE646] (the human albumin expression plasmid incorporating a modified leader sequence in accordance with the present invention) was cultured for a comparable length of time.

When the strain C fermentations were run in fill and draw mode a 13% and 6% increase in human albumin productivity ($Y_{P/S}$) relative to that of Strain C [pAYE443] was observed when Strain C [pAYE655] and Strain C [pAYE646] (the human albumin expression plasmids incorporating modified leader sequence in accordance with the present invention) were each cultured for a comparable length of time, respectively. This increased to 442% and 408% relative to that of Strain C [pAYE638] when Strain C [pAYE655] and Strain C [pAYE646] (the human albumin expression plasmids incorporating a modified leader sequence in accordance with the present invention) were each cultured for a comparable length of time, respectively.

SUMMARY

Plasmids pAYE443 and pAYE638 both encode human albumin having a leader sequence derived from HSA/MFα-1 fusion leader sequence, but the former uses the natural codon bias of the native polynucleotide sequences, while the latter uses a polynucleotide sequence which is fully codon optimised for yeast expression. Expression of human albumin obtained from pAYE638 is 4-5 fold lower than that obtained using pAYE443. A polynucleotide sequence encoding a modified leader sequence in accordance with the present invention has been substituted into the polynucleotide sequence encoding the HSA/MFα-1 fusion leader sequence of both pAYE443 and pAYE638 to create the human albumin expression plasmids pAYE665 and pAYE646, respectively. The introduction of the polypeptide sequence according to the present invention led to a significant improvement in production of the desired polypeptide.

The invention claimed is:

1. A non-naturally occurring polypeptide comprising:
(i) a leader sequence, the leader sequence comprising:
  (a) an albumin secretion pre sequence or albumin secretion pre sequence having at least 90% sequence identity to SEQ ID NO:28, and
  (b) the following motif:

-X₁-X₂-X₃-X₄-X₅- where X$_1$ is phenylalanine, tryptophan, or tyrosine, X$_2$ is isoleucine, leucine, valine, alanine or methionine, X$_3$ is leucine, valine, alanine or methionine, X$_4$ is serine or threonine and X$_5$ is isoleucine, valine, alanine or methionine; and
(ii) a sequence of a mature desired protein.

2. The polypeptide according to claim 1, wherein X$_1$ is phenylalanine.

3. The polypeptide according to claim 1, wherein X$_2$ is isoleucine.

4. The polypeptide according to claim 1, wherein X$_3$ is valine.

5. The polypeptide according to claim 1, wherein amino acids of the motif are included in the polypeptide as substitutions for naturally occurring amino acids.

6. The polypeptide according to claim 1, wherein X$_5$ is isoleucine.

7. The polypeptide according to claim 1, wherein the motif comprises the amino acid sequence of SEQ ID NO: 7.

8. The polypeptide according to claim 1, wherein the albumin secretion pre sequence is a variant having at least 9 identical amino acids to the albumin secretion pre sequence, wherein the at least 9 identical amino acids are not part of the motif.

9. The polypeptide according to claim 8, wherein X$_1$, X$_2$, X$_3$, X$_4$ and X$_5$ are at positions −20, −19, −18, −17 and −16, respectively, in place of the naturally occurring amino acids at those positions, wherein the numbering is such that the −1 residue is the C-terminal amino acid of the native albumin secretion pro sequence, and wherein X$_1$ is phenylalanine, tryptophan, or tyrosine, X$_2$ is isoleucine, leucine, valine, alanine or methionine, X$_3$ is leucine, valine, alanine or methionine, X$_4$ is serine or threonine and X$_5$ is isoleucine, valine, alanine or methionine.

10. The polypeptide according to claim 1 wherein the albumin secretion pre sequence or variant thereof is a human albumin secretion pre sequence.

11. The polypeptide according to claim 10 comprising the secretion pre sequence of SEQ ID NO: 28.

12. The polypeptide according to claim 1 wherein the leader sequence comprises a secretion pro sequence.

13. The polypeptide according to claim 12 wherein the secretion pro sequence is fused by a peptide bond at its C-terminal end to the N-terminal amino acid of a secretion pro sequence.

14. The polypeptide according to claim 13 wherein the secretion pro sequence is an albumin secretion pro sequence.

15. The polypeptide according to claim 14 wherein the albumin secretion pro sequence is human serum albumin secretion pro sequence.

16. The polypeptide according to claim 15 wherein the secretion pro sequence motif is the yeast MF-1 secretion pro sequence.

17. The polypeptide according to claim 12 comprising the sequence:

MKWVFIVSILFLFSSAYSRY$^1$Y$^2$Y$^3$Y$^4$Y$^5$ wherein Y$^1$ is Gly or Ser, Y$^2$ is Val or Leu, Y$^3$ is Phe or Asp, Y$^4$ is Arg or Lys and Y$^5$ is Arg or Lys.

18. The polypeptide according to claim 17, wherein Y$^1$ is Gly, Y$^2$ is Val and Y$^3$ is Phe; or Y$^1$ is Ser, Y$^2$ is Leu and Y$^3$ is Asp.

19. The polypeptide according to claim 17, wherein Y$^4$ is Arg and Y$^5$ is Arg; Y$^4$ is Lys and Y$^5$ is Arg; Y$^4$ is Lys and Y$^5$ is Lys; or Y$^4$ is Arg and Y$^5$ is Lys.

20. The polypeptide according to claim 1, wherein the sequence of the desired protein is fused at its N-terminal end to the C-terminal amino acid of the leader sequence.

21. The polypeptide according to claim 1, wherein the sequence of the desired protein is fused at its N-terminal end to the C-terminal amino acid of the leader sequence.

22. The polypeptide according to claim 1, wherein the mature desired protein is albumin.

23. The polypeptide according to claim 22, wherein the albumin is human albumin.

24. The polypeptide according to claim 1, wherein the mature desired protein is transferrin.

25. The polypeptide according to claim 24 wherein the transferring is human transferrin.

26. An isolated polynucleotide comprising a sequence that encodes the motif defined by claim 1.

27. The polynucleotide according to claim 26, comprising the sequence of SEQ ID NO: 15.

28. The polynucleotide according to claim 26 comprising the sequence of SEQ ID NO: 16.

29. The polynucleotide according to claim 26 comprising the sequence of SEQ ID NO: 17.

30. The polynucleotide according to claim 26 comprising the sequence of SEQ ID NO: 18.

31. The polynucleotide according to claim 26 comprising the sequence of SEQ ID NO: 34.

32. The polynucleotide according to claim 30 comprising the sequence of SEQ ID NO: 24.

33. The polynucleotide according to claim 32 comprising the sequence of SEQ ID NO: 25.

34. The polynucleotide according to claim 30 comprising the sequence of SEQ ID NO: 27.

35. The polynucleotide according to claim 34 comprising the sequence of SEQ ID NO: 21.

36. A polynucleotide comprising the sequence of SEQ ID NO: 21.

37. The polynucleotide according to claim 33, wherein the polynucleotide comprises a DNA sequence being a contiguous or non-contiguous fusion of a DNA sequence encoding a heterologous protein with either the DNA sequence SEQ ID NO: 25 or the DNA sequence SEQ ID NO: 21.

38. The polynucleotide which is the complementary strand of a polynucleotide according to claim 26.

39. The polynucleotide according to claim 26 comprising an operably linked transcription regulatory region.

40. The polynucleotide according to claim 39, wherein the transcription regulatory region comprises a transcription promoter.

41. A self-replicable polynucleotide sequence comprising a polynucleotide according to claim 26.

42. A cell comprising a polynucleotide according to claim 26.

43. The cell according to claim 42 which is a eukaryotic cell.

44. The cell according to claim 43 which is a fungal cell.

45. The cell according to claim 44 which is an *Aspergillus* cell.

46. The cell according to claim 44 which is a yeast cell.

47. The cell according to claim 46 which is a *Saccharomyces, Kluyveromyces, Schizosaccharomyces* or *Pichia* cell.

48. A cell culture comprising a cell according to claim 42 and culture medium.

49. The cell culture according to claim 48~ wherein the medium contains a mature desired protein.

50. A process for producing a mature desired protein, comprising (1) culturing a cell according to claim 42 in a culture medium wherein the cell, secretes a mature desired protein into the culture medium, and (2) separating the culture medium, containing the secreted mature protein, from the cell.

51. The process according to claim 50 comprising the step of separating the mature desired protein from the medium.

52. The process according to claim 51 comprising the step of formulating the separated mature desired protein with a therapeutically acceptable carrier or diluents thereby to produce a therapeutic product suitable for administration to a human or an animal.

53. A polynucleotide according to any one of claim 35, wherein the polynucleotide comprises a DNA sequence being a contiguous or non-contiguous fusion DNA sequence comprising SEQ ID NO: 25 or SEQ ID NO: 21.

54. The polynucleotide according to any one of claim 36, wherein the polynucleotide comprises a DNA sequence being a contiguous or non-contiguous fusion of a DNA sequence comprising SEQ ID NO: 25 or SEQ ID NO: 21.

55. The process according to claim 51 comprising the step of purifying the mature desired protein.

56. The process according to claim 55 comprising the step of formulating the separated and purified mature desired protein with a therapeutically acceptable carrier or diluent.

57. A non-naturally occurring leader sequence for directing the secretion of proteins, said leader sequence comprising:
(a) an albumin secretion pre sequence or albumin secretion pre sequence having at least 90% sequence identity to SEQ ID NO:28, and
(b) the following motif:

-X$_1$-X$_2$-X$_3$-X$_4$-X$_5$- where X$_1$ is phenylalanine, tryptophan, or tyrosine, X$_2$ is isoleucine, leucine, valine, alanine or methionine, X$_3$ is leucine, valine, alanine or methionine, X$_4$ is serine or threonine and X$_5$ is isoleucine, valine, alanine or methionine.

58. The leader sequence according to claim 57 comprising the secretion pre sequence of SEQ ID NO: 28.

59. The polypeptide in accordance with claim 1, wherein the albumin secretion pre sequence comprises SEQ ID NO:28.

60. The polypeptide in accordance with claim 1, wherein the albumin secretion pre sequence consists of SEQ ID NO:28.

61. The polypeptide in accordance with claim 1, wherein the albumin secretion pre sequence has at least 96% sequence identity to SEQ ID NO:28.

62. The polypeptide in accordance with claim 1, wherein the albumin secretion pre sequence has at least 97% sequence identity to SEQ ID NO:28.

63. The polypeptide in accordance with claim 1, wherein the albumin secretion pre sequence has at least 98% sequence identity to SEQ ID NO:28.

64. The polypeptide in accordance with claim 1, wherein the albumin secretion pre sequence has at least 99% sequence identity to SEQ ID NO:28.

65. The polypeptide in accordance with claim 1, wherein the mature desired protein is heterologous to the leader sequence.

66. The polypeptide in accordance with claim 1, wherein the motif is disposed within the albumin secretion pre sequence, and wherein the motif comprises the amino acid sequence of SEQ ID NO: 7.

67. The leader sequence in accordance with claim 57, wherein the albumin secretion pre sequence comprises SEQ ID NO:28.

68. The leader sequence in accordance with claim 57, wherein the albumin secretion pre sequence consists of SEQ ID NO:28.

69. The leader sequence in accordance with claim 57, wherein the albumin secretion pre sequence has at least 90% sequence identity to SEQ ID NO:28.

70. The leader sequence in accordance with claim 57, wherein the albumin secretion pre sequence has at least 95% sequence identity to SEQ ID NO:28.

71. The leader sequence in accordance with claim 57, wherein the albumin secretion pre sequence has at least 96% sequence identity to SEQ ID NO:28.

72. The leader sequence in accordance with claim 57, wherein the albumin secretion pre sequence has at least 97% sequence identity to SEQ ID NO:28.

73. The leader sequence in accordance with claim 57, wherein the albumin secretion pre sequence has at least 98% sequence identity to SEQ ID NO:28.

74. The leader sequence in accordance with claim 57, wherein the albumin secretion pre sequence has at least 99% sequence identity to SEQ ID NO:28.

75. The leader sequence in accordance with claim 57, wherein the motif is disposed within the albumin secretion pre sequence, and wherein the motif comprises the amino acid sequence of SEQ ID NO: 7.

\* \* \* \* \*